US008926945B2

(12) United States Patent
Port et al.

(10) Patent No.: US 8,926,945 B2
(45) Date of Patent: *Jan. 6, 2015

(54) COMPOUNDS COMPRISING A BIOLOGICAL TARGET RECOGNIZING PART, COUPLED TO A SIGNAL PART CAPABLE OF COMPLEXING GALLIUM

(75) Inventors: Marc Port, Deuil la Barre (FR); Claire Corot, Lyons (FR); Thierry Gautheret, Bois-le-Roi (FR)

(73) Assignee: Guerbet, Villepinte (FR)

( * ) Notice: Subject to any disclaimer, the term of this patent is extended or adjusted under 35 U.S.C. 154(b) by 1467 days.

This patent is subject to a terminal disclaimer.

(21) Appl. No.: 12/083,269

(22) PCT Filed: Oct. 9, 2006

(86) PCT No.: PCT/EP2006/067211
§ 371 (c)(1),
(2), (4) Date: Apr. 7, 2008

(87) PCT Pub. No.: WO2007/042504
PCT Pub. Date: Apr. 19, 2007

(65) Prior Publication Data
US 2011/0092806 A1 Apr. 21, 2011

(30) Foreign Application Priority Data

Oct. 7, 2005 (FR) ..................................... 05 10289
Apr. 5, 2006 (FR) ..................................... 06 02975

(51) Int. Cl.
| A61K 51/00 | (2006.01) |
| A61M 36/14 | (2006.01) |
| A61K 51/04 | (2006.01) |
| C07D 471/08 | (2006.01) |
| A61K 49/08 | (2006.01) |
| A61K 49/14 | (2006.01) |
| A61K 49/10 | (2006.01) |
| A61K 51/08 | (2006.01) |

(52) U.S. Cl.
CPC ............. *A61K 49/10* (2013.01); *A61K 51/0497* (2013.01); *C07D 471/08* (2013.01); *A61K 49/085* (2013.01); *A61K 49/14* (2013.01); *A61K 51/088* (2013.01)
USPC .......... 424/1.69; 424/1.11; 424/1.65; 424/9.1

(58) Field of Classification Search
CPC ..... A61K 49/06; A61K 49/085; A61K 49/00; A61K 49/0002; A61K 49/001; A61K 49/0013; A61K 49/0017; A61K 49/0021; A61K 49/0036; A61K 49/0039; A61K 49/08; A61K 49/10; A61K 49/101; A61K 49/12; A61K 49/14; A61K 51/00; A61K 51/0459; A61K 51/0497; A61K 51/08; A61K 51/088; C07F 9/6524; C07F 9/6544; C07D 213/02; C07D 213/00; C07D 213/12; C07D 213/16; C07D 257/02; C07D 487/00; C07D 487/02; C07D 239/95; C07D 471/08
USPC ........... 424/1.11, 1.45, 1.49, 1.53, 1.65, 1.69, 424/1.73, 9.1, 9.2, 9.3, 9.4, 9.5, 9.36, 9.361, 424/9.362, 9.363, 9.365; 540/450, 451, 540/454, 456, 460, 467, 470, 473, 474; 206/223, 569, 570
See application file for complete search history.

(56) References Cited

U.S. PATENT DOCUMENTS

| 4,017,596 A | * | 4/1977 | Loberg et al. ................ 424/1.65 |
| 5,079,346 A | * | 1/1992 | Kung .............................. 534/10 |
| 5,334,371 A | * | 8/1994 | Gries et al. ................... 424/9.34 |
| 5,403,572 A | | 4/1995 | Gries et al. |
| 5,707,605 A | | 1/1998 | Meade et al. |
| 5,712,389 A | | 1/1998 | Meyer et al. |
| 5,919,432 A | | 7/1999 | Meyer et al. |
| 6,071,490 A | | 6/2000 | Griffiths et al. |
| 6,261,535 B1 | | 7/2001 | Thorpe et al. |
| 6,264,914 B1 | | 7/2001 | Klaveness et al. |
| 6,372,194 B1 | | 4/2002 | Akaike et al. |
| 6,391,280 B1 | | 5/2002 | Hiatt et al. |
| 6,410,695 B1 | | 6/2002 | Sinn et al. |
| 6,440,956 B1 | * | 8/2002 | Port .............................. 514/186 |
| 6,489,333 B2 | | 12/2002 | Pitts et al. |
| 6,491,893 B1 | | 12/2002 | Babich |
| 6,511,648 B2 | | 1/2003 | Harris et al. |
| 6,524,554 B1 | | 2/2003 | Edwards et al. |
| 6,534,038 B2 | | 3/2003 | Liu |

(Continued)

FOREIGN PATENT DOCUMENTS

| EP | 0 352 218 A2 | 1/1990 |
| EP | 0 425 212 A2 | 5/1991 |

(Continued)

OTHER PUBLICATIONS

Moerlein, S.M. et al., "A Gallium-68 Labeled Chemotactic Peptide Analogue for Imaging Focal Sites of Bacterial Infection by PET." Symposium Abstracts, Paper 19, pp. 426-427. XP008010914. (1992).

Nakamoto, Yuji et al. "Effects of Nonionic Intravenous Contrast Agents at PET/CT Imaging: Phantom and Canine Studies" Radiology, vol. 227, No. 3, Jun. 2003 pp. 817-824. XP002413062.

Froidevaux, S. et al. "A Gallium-Labeled DOTA-α-Melanocyte-Stimulating Hormone Analog for PET Imaging of Melanoma Metastases" The Journal of Nuclear Medicine, vol. 45, No. 1, Jan. 2004, pp. 116-123. XP 002364150.

(Continued)

*Primary Examiner* — D L Jones
(74) *Attorney, Agent, or Firm* — Birch, Stewart, Kolasch & Birch, LLP

(57) ABSTRACT

The invention concerns compounds comprising a biological target recognizing part, coupled to a signal part capable of complexing gallium. The invention also concerns methods for obtaining said compounds, screening methods capable of selecting such compounds for chemical synthesis thereof and their diagnostic applications, in particular in PET, PET/IRM, PET CT imaging.

13 Claims, No Drawings

(56) References Cited

U.S. PATENT DOCUMENTS

| | | |
|---|---|---|
| 6,537,520 B1 | 3/2003 | Rajopadhye et al. |
| 6,827,927 B1 | 12/2004 | Rousseaux et al. |
| 2002/0106325 A1 | 8/2002 | Carpenter |
| 2002/0128553 A1 | 9/2002 | Mishani et al. |
| 2003/0082106 A1 | 5/2003 | Nivorozhkin et al. |
| 2003/0152513 A1 | 8/2003 | Blankenberg et al. |
| 2004/0210041 A1 | 10/2004 | Arbogast et al. |
| 2005/0048000 A1 | 3/2005 | Gervais et al. |
| 2005/0191238 A1 | 9/2005 | Casebier et al. |
| 2005/0201943 A1 | 9/2005 | Nivorozhkin et al. |
| 2006/0233704 A1 | 10/2006 | Maecke et al. |
| 2007/0098643 A1 | 5/2007 | Nachman et al. |
| 2007/0258905 A1 | 11/2007 | Aime et al. |

FOREIGN PATENT DOCUMENTS

| | | |
|---|---|---|
| EP | 0 438 206 A1 | 7/1991 |
| EP | 0 661 279 A1 | 7/1995 |
| EP | 1 121 377 | 4/2000 |
| JP | 10-501528 A | 2/1998 |
| JP | 2004-509152 A | 3/2004 |
| WO | WO-93/19787 A | 10/1993 |
| WO | WO 94/00489 | 1/1994 |
| WO | WO-94/04485 A | 3/1994 |
| WO | WO-94/04488 A | 3/1994 |
| WO | WO 94/05269 | 3/1994 |
| WO | WO 95/32741 A1 | 12/1995 |
| WO | WO 96/36367 | 11/1996 |
| WO | WO-98/39288 A | 9/1998 |
| WO | WO 99/40947 | 8/1999 |
| WO | WO 99/54317 | 10/1999 |
| WO | WO 00/21980 | 4/2000 |
| WO | WO 00/61195 | 10/2000 |
| WO | WO-00/71526 A1 | 11/2000 |
| WO | WO 01/00637 A1 | 1/2001 |
| WO | WO 01/09188 A1 | 2/2001 |
| WO | WO 01/10450 A1 | 2/2001 |
| WO | WO-01/52900 A2 | 7/2001 |
| WO | WO 01/60416 A2 | 8/2001 |
| WO | WO 01/77102 A1 | 10/2001 |
| WO | WO 01/77122 A1 | 10/2001 |
| WO | WO 01/77145 A2 | 10/2001 |
| WO | WO 01/97850 A2 | 12/2001 |
| WO | WO 01/97861 A2 | 12/2001 |
| WO | WO 01/98294 A2 | 12/2001 |
| WO | WO 02/26776 A2 | 4/2002 |
| WO | WO 02/28441 A2 | 4/2002 |
| WO | WO 02/32292 A2 | 4/2002 |
| WO | WO 02/38546 A1 | 5/2002 |
| WO | WO-02/40060 A | 5/2002 |
| WO | WO 0244156 A2 | 6/2002 |
| WO | WO 02/053192 A1 | 7/2002 |
| WO | WO 02/054088 A2 | 7/2002 |
| WO | WO 02/056670 A2 | 7/2002 |
| WO | WO 02/059110 A1 | 8/2002 |
| WO | WO 02/062810 A2 | 8/2002 |
| WO | WO 02/066512 A1 | 8/2002 |
| WO | WO 02/081497 A2 | 10/2002 |
| WO | WO 02/085908 A1 | 10/2002 |
| WO | WO 02/094873 A2 | 11/2002 |
| WO | WO 03/006059 A1 | 1/2003 |
| WO | WO-03/008390 A1 | 1/2003 |
| WO | WO 03/011115 A2 | 2/2003 |
| WO | WO-03/013346 A | 2/2003 |
| WO | WO 03/014145 A2 | 2/2003 |
| WO | WO 03/018640 A2 | 3/2003 |
| WO | WO 03/020701 A2 | 3/2003 |
| WO | WO-03/059397 A | 7/2003 |
| WO | WO-03/074523 A2 | 9/2003 |
| WO | WO 03/077727 A2 | 9/2003 |
| WO | WO 03/078569 A2 | 9/2003 |
| WO | WO 03/086475 A1 | 10/2003 |
| WO | WO 03/086476 A1 | 10/2003 |
| WO | WO 2004/058275 A2 | 7/2004 |
| WO | WO 2004/069365 A1 | 8/2004 |
| WO | WO 2004/089425 A1 | 10/2004 |
| WO | WO-2004/089517 A | 10/2004 |
| WO | WO-2004/089517 A1 * | 10/2004 |
| WO | WO 2004/112839 A2 | 12/2004 |
| WO | WO-2004/112840 A | 12/2004 |
| WO | WO-2004/112840 A2 | 12/2004 |
| WO | WO 2005/002293 A2 | 1/2005 |
| WO | WO 2005/009393 A2 | 2/2005 |
| WO | WO 2005/012335 A1 | 2/2005 |
| WO | WO 2005/019247 A2 | 3/2005 |
| WO | WO 2005/023314 A1 | 3/2005 |
| WO | WO 2005/042033 A1 | 5/2005 |
| WO | WO 2005/044312 A1 | 5/2005 |
| WO | WO 2005/044313 A2 | 5/2005 |
| WO | WO 2005/046563 A2 | 5/2005 |
| WO | WO 2005/049095 A2 | 6/2005 |
| WO | WO 2005/049096 A2 | 6/2005 |
| WO | WO 2005/079886 A2 | 9/2005 |
| WO | WO 2005/082425 A1 | 9/2005 |
| WO | WO 2005/082889 A1 | 9/2005 |
| WO | WO 2005/084168 A2 | 9/2005 |
| WO | WO-2006/002873 A2 | 1/2006 |
| WO | WO 2006/071754 A2 | 7/2006 |
| WO | WO-2006/090232 A | 8/2006 |
| WO | WO 2006/095234 A2 | 9/2006 |
| WO | WO-2006/100305 A | 9/2006 |
| WO | WO 2007/042504 A2 | 4/2007 |
| WO | WO 2010/092114 A1 | 8/2010 |

OTHER PUBLICATIONS

Henze M et al., "PET imaging of Somatostatin Receptors Using [$^{68}$GA]DOTA-D-Phe$^1$-Octreotide: First Results in Patients with Meningiomas" Journal of Nuclear Medicine, vol. 42, No. 7, Jul. 2001, pp. 1053-1056.

Velikyan I et al., "Preparation and Evaluation of $^{68}$Ga-DoOTA-hEGF for Visualization of EGFR Expression in Malignant Tumors" Journal of Nuclear Medicine, Society of Nuclear Medicine, vol. 46, No. 11, Nov. 2005, pp. 1881-1888.

Hoffend J et al.,"Gallium-68-DOTA-albumin as a PET blood-pool marker: experimental evaluation in vivo" Nuclear Medicine and Biology, vol. 32, 2005, pp. 287-292.

Henze M et al., Journal of Nuclear Medicine, vol. 42, No. 7, Jul. 2001, pp. 1053-1056.

Velikyan I et al., Journal of Nuclear Medicine, Society of Nuclear Medicine, vol. 46, No. 11, Nov. 2005, pp. 1881-1888.

Hoffend J et al., Nuclear Medicine and Biology, vol. 32, 2005, pp. 287-292.

Favoni et al., "The Role of Polypeptide Growth Factors in Human Carcinomas: New Targets for a Novel Pharmacological Approach", Pharmacological Reviews, vol. 52, No. 2 (2000) pp. 179-206.

Kling et al., "Design and Synthesis of 1,5- and 2,5-Substituted Tetrahydrobenzazepinones as Novel Potent and Selective Integrin αvβ3 Antagonists", Bioorganic & Medicinal Chemistry, vol. 11 (2003) pp. 1319-1341.

Krause, "Liver-Specific X-Ray Contrast Agents", Topics in Current Chemistry, vol. 222 (1992) pp. 173-199.

Liu et al., "Fundamentals of Receptor-Based Diagnostic Metalloradiopharmaceuticals", Topics in Current Chemistry, vol. 222 (1992) pp. 259-278.

Luyt et al., "A Trithiolate Tripodal Bifunctional Ligand for the Radiolabeling of Peptides with Gallium (III)", Bioconjugate Chem., vol. 13 (2002) pp. 1140-1145.

Mathias et al., "Indium-111-DTPA-Folate as a Potential Folate-Receptor-Targeted Radiopharmaceutical", J. of Nuclear Medicine, vol. 39 (1996) pp. 1579-1585.

Morikawa et al., "Treatment of Focal Cerebral lschemia with Synthetic Oligopeptide Corresponding to Lectin Domain of Selectin", Stroke, vol. 27 (1996) pp. 951-956.

Siegel et al., "Evaluation of 111In-DTPA-Folate as a Receptor-Targeted Diagnostic Agent for Ovarian Cancer: Initial Clinical Results", J. of Nuclear Medicine, vol. 44, No. 5 (2003) pp. 700-707.

Zheng et al., "Multimodal Contrast Agent for Combined Computed Tomography and Magnetic Resonance Imaging Applications", Investigative Raiology, vol. 41, No. 3 (2006) pp. 339-348.

(56) References Cited

OTHER PUBLICATIONS

J. Schuhmacher et al., GRP Receptor-Targeted PET of a Rat Pancreas Carcinoma Xenograft in Nude Mine with a 68GA-Labeled Bombesin (6-14) Analog, The Journal of Nuclear Medicine, 2005, vol. 46 No. 4, pp. 691-699.

J.P. Andre, "1,4,7-Triazacyclononane-1-succinic acid-4,7-diacetic acid (NODASA): a new bifunctional chelator for radio gallium-labeling of biomolecules", Chemical Communications, 1998, No. 12, pp. 1301-1302.

K.P. Eisenwiener et al., NODAGATOC, a New Chelator-Coupled Somatostatin Analogue Labeled with 67/68Ga and [111In] for SPECT, PET, and Targeted Therapeutic Applications of Somatostatin Receptor (hsst2) Expressing Tumors, Bioconjugate Chemistry, 2002, vol. 13, No. 3, pp. 530-541.

\* cited by examiner

COMPOUNDS COMPRISING A BIOLOGICAL TARGET RECOGNIZING PART, COUPLED TO A SIGNAL PART CAPABLE OF COMPLEXING GALLIUM

The invention relates to compounds comprising a portion for recognition of a biological target, coupled to a signal portion capable of complexing gallium. The invention also relates to processes for obtaining these compounds, and to screening processes capable of selecting such compounds for their chemical synthesis and their diagnostic uses.

Compounds denoted specific vectorized compounds for molecular imaging in nuclear medicine are already known.

Numerous compounds comprising a biovector coupled to a radionuclide are thus known. Depending on the nature of the biovector and of the radionuclide, the biovector is coupled to the radionuclide either directly, or by means of a chelate which complexes the radionuclide. According to the decay spectrum of the radionuclides, they can be used for PET imaging or for SPECT imaging.

PET imaging (emission of positrons giving rise to an emission of photons detected by a PET scanner) using the F18 radionuclide is particularly used for the metabolic monitoring of tumour zones using FDG (fluorodeoxyglucose). A major drawback of the use of the common isotopes such as F18 in PET is the need for a cyclotron which produces the isotope, in general in the vicinity of the site where the product is administered to the patient, given the lifetime of the isotopes, which poses considerable problems in terms of cost and logistics.

Numerous compounds using technicium and indium have been described for their use in SPECT imaging (photon emission, with use of radionuclides emitting an energy of the order of 100 to 200 keV, in particular). However, SPECT gives a poorer spatial resolution than PET and can involve visualization of the patient 2 to 3 days after the administration of the product due to the lifetime of certain isotopes such as In111.

The choice between PET and SPECT depends in particular on the diagnostic indication.

The applicant has particularly focused on the use, in PET imaging, of gallium Ga68 since this isotope is produced, not by a cyclotron, but by a generator (germanium Ge68/gallium Ga68), an apparatus which is much less complex and expensive than the cyclotron.

Specific compounds using Ga68 have been described, in particular Ga68/S3N (tetradentate amine trithiolate chelating agent), and DOTATOC (DOTA-DPhel-Tyr3-octreotide, the biovector being a somatostatin analogue). It is recalled that, due to the 3+ oxidation state of Ga68, the latter is typically coupled to various chelates, including in particular derivatives of DOTA, DTPA or NOTA. Two preparation processes are possible:
- the biovector is coupled to the chelate and then the compound formed is complexed with the Ga68 produced by the generator;
- the chelate is complexed with the Ga68 produced by the generator, and then the complex formed is coupled to the biovector.

The lifetime of Ga68 is 68 minutes, which makes its use in clinical PET possible, but, as for F18 (the half-life of which is 121 minutes), it requires a short time for preparing the product incorporating the Ga68, preferably less than approximately 40 minutes. A preparation process with microwaves, intended to reduce the time for preparing compounds with Ga68, has been described in WO 2004/089425.

There remains the need to obtain new compounds using Ga68 that are particularly effective, in particular for certain diagnostic indications not covered to date with this isotope, and the preparation of which is sufficiently rapid and simple for common and economical clinical use.

The applicant has succeeded in obtaining advantageous novel compounds and, according to one aspect, the invention relates to a method for selecting compounds that are effective in PET imaging of gallium Ga68, comprising:
- the selection of biovectors B having an at least micromolar, preferably nanomolar, affinity from a base of active pharmacological molecules;
- the selection of chelates Ch having, with gallium $^{68}Ga^{3+}$, a log K affinity constant of at least 10, and preferably of at least 20, of at least 25, of at least 30 or of at least 35, from a library of linear or macrocyclic chelates;
- the selection of chemical linkers L for the coupling of at least one biovector with at least one chelate (denoted Ch in the application);
- the synthesis of the compounds (B-L-Ch);
- the synthesis of the compounds (B-L-Ch-Ga68) by complexation of the compound (B-L-Ch) with the Ga68;
- PET imaging of the compound (B-L-Ch-Ga68).

The expression "biovector derived from a base of active pharmacological molecules" is intended to mean any molecule (denoted biovector) having a known activity for targeting a pathological and/or diagnostic zone of interest, in particular molecules derived from chemical libraries, and in particular any biovector or category of biovectors mentioned in the present application.

According to one embodiment, the base or chemical library is a library of biovectors used for SPECT imaging.

According to one embodiment, the base or chemical library is a library of biovectors used for PET imaging with F18.

The invention also relates to any vectorized product that can be used in PET imaging with gallium Ga68, obtained by the above selection process.

The invention also relates to a process for preparing compounds that are effective in PET imaging of gallium Ga68 with or without microwaves, comprising:
- the synthesis of a compound (B-Ch) by coupling a biovector to a linear or macrocyclic chelate;
- the complexation of the compound (B-Ch) with gallium Ga68 in less than 20 minutes.

In the case of the process without microwaves, the yield will be advantageously greater than 30% and the purity greater than 50%.

The invention also relates to compounds intended for PET imaging with gallium 68, comprising a biovector B and a chelate Ch capable of complexing Ga68, advantageously linked by a linker L, the linker comprising at least one portion for masking the chelate in vivo, in particular a hydrophilic group. Advantageously, this masking portion is chosen so as not to impair the biovector's affinity with its biological target.

The invention also relates to compounds intended for PET imaging with gallium 68, comprising a biovector B and a chelate Ch capable of complexing Ga68, advantageously linked by a linker L, the chelate also comprising a portion for recognition of a biological target that improves the biodistribution of the compound, said recognition portion being different than the biovector.

Advantageously, the present invention relates to

The applicant has targeted several major lines of improvement.

According to one aspect, the applicant has studied products of which the gallium-complexing chelate does not impair the specificity of recognition of the biological target by the biovector of the product. The applicant has thus studied several pathways of chemical synthesis and several types of chelates that do not impair this recognition.

According to another aspect, the applicant has studied products whose targeting specificity is particularly high. The applicant has thus studied several pathways of chemical synthesis and several types of biovectors that improve the specificity of the product. The applicant has thus sought biovectors with high specificity, in particular known biovectors of the therapeutic field, preferably having an at least micromolar, in particular nanomolar, affinity but which are not yet used in the diagnostic field. The applicant has also studied the possibilities of associating several biovectors, with one another or by means of the chelate(s) of the product:
- the biovectors are coupled to one another by a chemical linker group, at least one biovector being coupled to at least one chelate;
- the compound comprises a chelate described as central and carrying several biovectors by means of appropriate linkers;
- where appropriate, the biovector is coupled to a chelate which is itself coupled to several chelates connected to one another by appropriate linkers.

The applicant has, moreover, studied an assembly between the biovector(s) and the chelate(s) in such a way that the access to the target is not hindered despite the presence of the chelate(s):
- the chelate is distanced from the biovector(s) by a linker having a sufficient size and having a chemical structure such that the recognition of the biovector(s) by the target is not impaired;
- for biovectors having a sufficient size, the biovector comprises, firstly, a portion for recognition of the biological target, not directly connected to the chelate, and, secondly, at least one structural portion, the binding (direct or by a linker) of which with one or more chelates does not interfere with the specific recognition;
- the structure of the chelate is defined in such a way that it appears to be invisible or transparent in a biological medium with respect to the biovector. These chelates are in particular useful when the biovector must reach a recognition site that is difficult to access, such as a catalytic site of an enzyme, or for biovectors whose coupling with known chelates poses a problem of specificity or of recognition by their biological target (in particular biovectors of small size and/or having difficulties in accessing a biological zone). This transparent nature can be obtained by using appropriate chemical groups, in particular hydrophilic groups or, conversely, lipophilic groups masking the chelate. In this case, the chelate comprises at least one portion for masking the chelate in vivo.

Among the biovector/chelate associations, mention may in particular be made of:
- a central biovector connected to several chelates;
- a central chelate connected to several identical or different biovectors;
- a first assembly [biovector carrying chelate (s)] coupled by means of a hydrophobic or hydrophilic linker to a second assembly [biovector carrying chelate(s)], written, for example, (Ch)2-B1-Linker-B2(Ch)2 with Ch representing identical or different chelates and B1 and B2 representing identical or different biovectors;
- several biovectors forming a type of crown in interaction with the gallium;
- an assembly B1-(Linker carrying Ch)-B2-Ch.

For these associations, use will advantageously be made of the chelates in particular cited on pages 18-19, in particular of U.S. Pat. No. 6,440,956 and U.S. Pat. No. 5,919,432.

The applicant has also studied compounds that can be used in PET imaging of Ga68 and comprising, in addition to the biovector and the chelate, a chemical structure which confers thereon useful diagnostic properties, according to a logic described, for example, in WO 2005/082425, pages 60-67, in particular polymers (polysaccharides, polyamino acids, hydrophilic polymers of PEG type, for example), encapsulation systems of liposome type, lipid systems for transport and/or for release of the diagnostic compound, such as liposomes, micelles (which allow passage through the lymphatic system instead of the circulatory system) or nanoemulsions.

The applicant has also studied several pathways of chemical synthesis and several types of chelates making it possible to activate the product at the targeting site, according to "intelligent" or "smart" functioning. When the product is in proximity to its target in vivo, it undergoes a structural modification such that the affinity of the biovector with respect to its target is enhanced. The term "enhanced affinity" is intended to mean that the biovector has a better recognition and/or that its interaction time with its target is increased. For example, the product undergoes a conformational modification and/or a cleavage, for example enzymatic cleavage, resulting in better exposure of the binding site of the biovector with respect to its target. The cause of said structural modification may be local, in particular linked to the pH, to the oxidoreduction potential, etc. The biovector may, for example, be a substrate or an inhibitor of an enzyme.

According to another aspect, compounds are sought in which the biovector is coupled directly to at least one gallium, without the use of chelate, the biovector recognition not being impaired by the interaction between the biovector and the gallium atom(s). Various cases are possible, for example:
- the biovector comprises two sites, including one target recognition site and one site for interaction with the gallium, the second site forming a type of box around the gallium;
- the biovector comprises several sites, each site being both a recognition site and a site for interaction with the gallium, each site forming a type of box around the gallium. Where appropriate, these two recognition sites are different biovectors targeting identical or different targets.

It is also possible to use compounds comprising, in addition to the chelate and to the targeting biovector portion, a transport portion capable of transporting the targeting biovector to a zone of interest. For example, the zone of interest will be a biological territory of the brain made accessible to the compound by virtue of a transporter capable of crossing the blood-brain barrier (BBB). There will be for example, the following associations: (Ch)-X-L1-Y; X-(Ch)-Y; X-L1-(Ch)-L2-Y, with: X a targeting biovector, Y a transport portion, and L1 and L2 linkers, where appropriate biodegradable.

According to another aspect, the applicant has studied the use of biovectors known for their high specificity for a biological target associated with a pathological zone, but the coupling of which with the isotopes commonly used in nuclear medicine, in particular with F18, is chemically difficult and/or poses problems of stability of the biovector-F18 complex synthesized. The applicant has thus studied the use of biovectors recognized for their specificity (typically of at least $10^{-9}$ to $10^{-12}$ M), and the coupling of which with gallium (by means of the chelate) is much easier and/or rapid and/or provides a more stable compound than with F18. This also makes it possible to give the practitioner more time in which to use the product clinically.

The difficulties in coupling F18 (Kryptofix R, exchange reaction with mesylate or triflate, use of anhydrous F18, F18-

F2, F18XeF2, F18 DAST, etc.) are recalled in the prior art, for example in WO 2005/082425.

The applicant has in particular studied the use of gallium instead of F18 for diagnostic indications (using appropriate biovectors) requiring the high spatial resolution of PET (2 to 3 times greater than that of SPECT), in particular in oncology (early diagnosis of cancers, assessment of spread, monitoring of therapies), neurology, cardiology and infectiology. The detection of tumour zones of the order of 5 mm, and the detection of primary tumours and of metastatic nodules will in particular be targeted.

The applicant has also studied the use of gallium instead of F18 for biovectors for which the specificity of recognition of their target (in particular between a normal zone and a pathological zone or a zone at pathological risk) is quite high, in order to obtain a good contrast in the image and therefore to meet the diagnostic requirement, even though the resolution in PET imaging with gallium is lower than with F18.

The applicant has in particular studied the use of gallium for the PET myocardial perfusion imaging diagnostic indication, optionally in combination with a therapeutic treatment, by selecting the promising biovectors from the list of the numerous biovectors that are used or that can be used in this indication.

The applicant has also studied diagnostic PET imaging products incorporating Ga68 for monitoring the efficacy of a therapeutic product, the biovector of the diagnostic compound being identical to or different than the biovector of the therapeutic product, the two products being coadministered simultaneously or with a delay between them. It is also possible to use mixed compounds comprising a therapeutic portion and a diagnostic portion, that optionally separate at the site of action of the mixed compound.

The applicant has also studied imaging methods more especially intended for PET imaging of Ga68, in particular apparatuses, sequences, signal processing methods, acquisition, transfer and data compilation methods, suited to the particularities (half-life, etc.) of Ga68. Physiological imaging using the Ga68 PET imaging product is, where appropriate, combined with anatomical reading on a scanner with, optionally, an X-ray scan contrast product. A Ga68-PET product and another contrast product can be coadministered simultaneously or with a delay between them. The applicant has thus studied possibilities of administering several products, almost simultaneously or, conversely, with a delay of a few hours between them, for PET imaging, each product providing a relevant piece of diagnostic information, for example a product labeled with F18 and a product labeled with Ga68. The applicant has also studied the possibilities of combining the results obtained on the same patient by combining the imaging methods using Ga68-labeled products, for example in PET-CT or in PET-MRI.

The applicant has also focused on compounds comprising a biovector used in SPECT imaging with technicium or indium, for example, but that it will be advantageous to use in PET imaging with gallium, given the known efficiency of specific recognition of these biovectors. The choice of such compounds is made possible due to the fact that the chemistry is quite similar between gallium and these elements. For example, such compounds comprise a biovector coupled to a chelate complexing gallium instead of indium, with the advantage that the results are obtained rapidly, whereas the use of indium required visualization of the patient 2 to 3 days after the administration of the product.

In addition, the applicant has studied the use of biovectors known for their use in certain known SPECT indications given the radionuclide used up until now (technicium, in particular), in other diagnostic PET imaging indications through the use of Ga68 instead of the radionuclide used up until now.

In addition, unlike the use of indium which requires a chelate and/or a biovector that is (are) stable for at least 2 to 3 days, with gallium the chelate and/or the chelate/biovector compound can be stable for only 1 to 3 hours (the time for preparing the product and for imaging the patient).

The applicant has in particular studied compounds comprising biovectors whose biodistribution kinetics are such that the gallium has not decayed before reaching its biological target, since these compounds reach their target in the patient in less than two to three hours.

Among the biovectors used in SPECT, the applicant has in particular studied improvements developed for SPECT and liable to be useful for gallium PET. Mention may in particular be made of:
  coupling with quinoline and quinolinine derivatives (WO 2005/079886);
  coupling with mitochondrial targeting derivatives with sufficient targeting and retention in the myocardium (rotenone derivatives in WO 2003/086476, MCI inhibitor derivatives of US 2005/0191238);
  coupling with pyridyl and imidazolyl derivatives (WO 2003/077727);
  coupling with benzodiazepine derivatives (WO 00/61195) for the targeting of GPIIbIIa (thrombus) with chelates carrying sulphide groups;
  coupling with derivatives carrying phosphine functions carrying hydroxyl, polyhydroxyl, carboxyl or polycarboxyl groups (WO 01/77122) for improving the biodistribution, in particular, of biovectors targeting integrins;
  use of agents for protection against oxidation (WO 01/00637);
  use of stabilizing agents (radioprotective and antimicrobial agents of WO 02/053192);
  use of Cardiolite and Myoview derivatives.

For the choice of appropriate biovectors, the applicant has focused most particularly on the major families of biovectors used in therapeutics and/or in diagnostic imaging: proteins, glycoproteins, lipoproteins, polypeptides, peptides, peptidomimetics, dyes, sugars, oligosaccharides, neuromediators, and in general, any peptide or nonpeptide ligand known to those skilled in the art as being capable of recognizing at least one biological target such as, in particular, receptors or enzymes, without any unwanted impairment of the biological activity of the target due to the coupling with the chelate.

For the choice of biovectors, the applicant has focused on any biovector:
  known in the prior art and that can be used in imaging;
  known in the prior art, not described for imaging, but which can be given its specific recognition of at least one biological target that is an indicator of a pathological state or of a risk of a pathological state.

The choice of the biovector can be made according to its structure and/or according to its desired use in imaging, such as the labeling of a biological mechanism that may be modified and that is reflected, for example, by a modified level of expression of the target of the biovector compared with the nonpathological state: cell receptors, cell metabolism, intra- or extracellular transport, molecules that inform and/or activate effectors or cells.

By way of examples, mention will be made of the following biovectors, mentioned in particular in WO 2004/112839, capable of targeting a ligand associated with (directly or indirectly involved in and/or overexpressed in) a pathological process.

1) The biovectors described in documents WO 01/97850 (targeting VEGF and antiopoietin receptors), U.S. Pat. No. 6,372,194 (polymer such as polyhistidine), WO 2001/9188 (polypeptide targeting fibrin), WO 01/77145 (integrin targeting peptide), WO 02/26776 (αv↑3 integrin targeting ligand), WO 99/40947 (ligands targeting, for example, the KDR/Flk-1 receptor, including R—X—K—X—H and R—X—K—X—H, or Tie-1 and 2 receptors), WO 02062810 (sialyl Lewis glycosides), WO 02/40060 (antioxidants such as ascorbic acid), U.S. Pat. No. 6,524,554 (targeting of tuftsin), WO 02/094873 (targeting of GPCR G-protein receptors, in particular cholecystokinin), U.S. Pat. No. 6,489,333 (integrin antagonist and guanidine mimetic association), U.S. Pat. No. 6,511,648 (quinolone targeting αvβ3 or 5), US 2002/0106325, WO 01/97861 (integrin-targeting benzodiazepines and analogues), WO 01/98294 (imidazoles and analogues), WO 01/60416 (MMP inhibitors, in particular hydroxamates), WO 02/081497 (αvβ3-targeting peptides such as RGD-WXE), WO 01/10450 (RGD peptides), U.S. Pat. No. 6,261,535 (antibodies or antibody fragments for FGF, TGFb, GV39, GV97, ELAM, VCAM, inducible with TNF or IL), U.S. Pat. No. 5,707,605 (targeting molecule modified by interaction with its target), WO 02/28441 (agents for targeting amyloid deposits), WO 02/056670 (cathepsin-cleaved peptides), U.S. Pat. No. 6,410,695 (mitoxantrone or quinone), U.S. Pat. No. 6,391,280 (polypeptides targeting epithelial cells), U.S. Pat. No. 6,491,893 (GCSF), US 2002/0128553, WO 02/054088, WO 02/32292, WO 02/38546, WO 20036059, U.S. Pat. No. 6,534,038, WO 99/54317 (cysteine protease inhibitors), WO 0177102, EP 1 121 377, Pharmacological Reviews (52, No. 2, 179; growth factors PDGF, EGF, FGF, etc.), Topics in Current Chemistry (222, W. Krause, Springer), Bioorganic & Medicinal Chemistry (11, 2003, 1319-1341; tetrahydrobenzazepinone derivatives targeting αvβ3).

2) Angiogenesis inhibitors, in particular those tested in clinical trials or already commercially available, in particular:
angiogenesis inhibitors involving FGFR or VEGFR receptors, such as SU101, SU5416, SU6668, ZD4190, PTK787, ZK225846, azacycle compounds (WO 00/244156, WO 02/059110);
angiogenesis inhibitors involving MMPs, such as BB25-16 (marimastat), AG3340 (prinomastat), solimastat, BAY12-9566, BMS275291, metastat, neovastat;
angiogenesis inhibitors involving integrins, such as SM256, SG545, adhesion molecules blocking EC-ECM (such as EMD 121-974, or vitaxin);
medicaments with a more indirect anti-angiogenic mechanism of action, such as carboxyamidotriazole, TNP470, squalamine, ZD0101;
the inhibitors described in document WO 99/40947, monoclonal antibodies highly selective for binding to the KDR receptor, somatostatin analogues (WO 94/00489), selectin-binding peptides (WO 94/05269), growth factors (VEGF, EGF, PDGF, TNF, MCSF, interleukins);
VEGF-targeting biovectors described in Nuclear Medicine Communications, 1999, 20;
the inhibitory peptides of document WO 02/066512;
folate derivatives;
agents for targeting Alzheimer's disease;
exopolysaccharides.

3) Biovectors capable of targeting receptors: CD36, EPAS-1, ARNT, NHE3, Tie-1, 1/KDR, Flt-1, Tek, neuropilin-1, endoglin, pleiotropin, endosialin, Ax1., alPi, a2ss1, a4P1, a5pl, eph B4 (ephrin), laminin A receptor, neutrophilin receptor, OB-RP leptin receptor, CXCR-4 chemokine receptor (and other receptors mentioned in document WO 99/40947), LHRH, bombesin/GRP, gastrin receptors, VIP, CCK.

4) Biovectors of tyrosine kinase inhibitor type.

5) Known GPIIb/IIIa receptor inhibitors chosen from: (1) the Fab fragment of a monoclonal antibody for the GPIIb/IIIa receptor, Abciximab (ReoPro™), (2) small peptide and peptidomimetic molecules injected intravenously, such as eptifibatide (Integrilin™) and tirofiban (Aggrastat™), it being recalled that the possible choice of an antibody will have to take into account the time for reaching its target.

6) Ligands that are antagonists for fibrinogen receptors (EP425212), peptides that are ligands for IIb/IIIa receptors, fibrinogen ligands, thrombin ligands, peptides capable of targeting atheroma plaque, platelets, fibrin, hirudin-based peptides, guanine-based derivatives for targeting the IIb/IIIa receptor.

7) Other biovectors or biologically active fragments of biovectors known to those skilled in the art, such as medicaments with anti-thrombotic, anti-platelet aggregation, anti-atherosclerotic, anti-restenotic or anticoagulant action.

8) Other biovectors or biologically active fragments of biovectors targeting αvβ3, described in association with DOTAs in U.S. Pat. No. 6,537,520, chosen from the following: mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustin, thymalfasin, sobuzoxane, nedaplatin, cytarabine, bicalutamide, vinorelbine, vesnarinone, aminoglutethimide, amsacrin, proglumide, elliptinium acetate, ketanserin, doxifluridine, etretinate, isotretinoin, streptozocine, nimustin, vindesine, flutamide, drogenil, butocin, carmofur, razoxane, sizofilan, carboplatin, mitolactol, tegafur, ifosfamide, prednimustin, picibanil, levamisole, teniposide, improsulfan, enocitabine, lisuride, oxymetholone, tamoxifen, progesterone, mepitiostane, epitiostanol, formestane, interferon-alpha, interferon-2-alpha, interferon-beta, interferon-gamma, colony stimulating factor-1, colony stimulating factor-2, denileukin diftitox, interleukin-2, leutinizing hormone releasing factor.

9) Certain biovectors targeting particular types of cancers, for example peptides targeting the ST receptor associated with colorectal cancer, or the tachykinin receptor.

10) Biovectors using phosphine-type compounds.

11) Biovectors for targeting P-selectin or E-selectin (for example, the 8-amino acid peptide described by Morikawa et al, 1996, 951).

12) Annexin V or biovectors targeting apoptotic processes.

13) Any peptide obtained by targeting technologies such as phage display, optionally modified with unnatural amino acids, for example peptides derived from phage display libraries: RGD, NGR, CRRETAWAC, KGD, RGD-4C, XXXY*XXX, RPLPP, APPLPPR.

14) Other known peptide biovectors for targeting atheroma plaques mentioned in particular in document WO 2003/014145.

15) Vitamins (in particular folates).

16) Hormone receptor ligands, including hormones and steroids.

17) Biovectors targeting opioid receptors.

18) Biovectors targeting TKI receptors, CXCR receptors (1 to 4, in particular).

19) LB4 and VnR antagonists.

20) Nitroimidazole and benzylguanidine compounds.

21) Biovectors recalled in Topics in Current Chemistry, vol. 222, 260-274, fundamentals of receptor-based diagnostic metallopharmaceuticals, in particular:
  biovectors for targeting peptide receptors overexpressed in tumors (LHRH receptors, bombesin/GRP, VIP receptors, CCK receptors, tachykinin receptors, for example), in particular somatostatin analogues or bombesin analogues, optionally glycosylated octreotide derived peptides, VIP peptides, alpha-MSHs, CCK-B peptides;
  peptides chosen from: cyclic ROD peptides, fibrin-alpha chain, CSVTCR (SEQ ID NO: tuftsin, fMLF, YIOSR (SEQ ID NO: 6) (receptor: laminin).
22) Polysaccharides and monosaccharide derivatives, derivatives targeting Glut.
23) Biovectors used for smart products.
24) Markers for myocardial viability (for example, tetrafosmin and hexakis-2-methoxy-2-methylpropylisonitrile).
25) Sugar and fat metabolism tracers.
26) Ligands for neurotransmitter receptors (D,5HT,Ach, GABA,NA receptors).
27) Oligonucleotides.
28) Peptide biovectors of WO 03/011115, pages 36 to 43.
28) Biovectors already used for SPECT or PET, mentioned in: WO 03/018640, WO 03/020701, WO 03/078569, US 2003/0152513, WO 03/086475, WO 2005/002293, US 20050048000, WO 2004/069365, WO 2005/012335, WO 2005/044312, WO 2005/042033, WO 2003/013346, WO 2005/023314, WO 2005/019247, WO 2005/049096, WO 2005/049095, WO 2005/044313, WO 2005/042033, US 2004/0210041, US 2005/201943, WO 2005/082889.
29) Biovectors derived from chemical scaffolds referred to as scaffolds and described in US 2005/026127.
30) Biovectors targeting GLUT, GLUT transporters (GLUT1 glucose receptors and the like) which are already known to be coupled to chelates complexed with lanthanides such as Gd3+.

For the linker portion of the product, mention will be made, by way of examples, of the following linkers:
1) Amino acids.
2) Linkers L capable of interacting with at least one functional group of the biovector and at least one functional group of the chelate. L includes in particular substituted or unsubstituted, saturated or unsaturated, straight or branched alkyl chains, peptides, polyethylene glycols and polyoxyethylenes. Mention will in particular be made of:
3) a.1) $(CH_2)_2$-phenyl-NH, $(CH_2)_3$—NH, NH—$(CH_2)_2$—NH, NH—$(CH_2)_3$—NH, nothing or a single bond, $(CH_2)_n$, $(CH_2)_n$—CO—, —$(CH_2)_n$NH—CO— with n=2 to 10, $(CH_2CH_2O)_q(CH_2)_r$—CO—, $(CH_2CH_2O)q(CH_2)_r$—NH—CO— with q=1-10 and r=2-10, $(CH_2)_n$—CONH—, $(CH_2)_n$—CONH-PEG, $(CH_2)_n$—NH—,

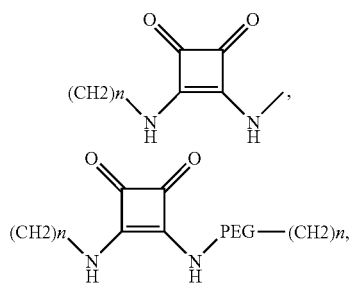

with n=1 to 5 and advantageously n=4 or 5, HOOC—$CH_2$—O—$(CH_2)_2$—O—$(CH_2)_2$—O—$CH_2$—COOH; HOOC—$(CH_2)_2$—$CO_2$—$(CH_2)_2$—OCO—$(CH_2)_2$—COOH; HOOC—CH(OH)—CH(OH)—COOH; HOOC—$(CH_2)_n$—COOH; $NH_2$—$(CH_2)_n$—$NH_2$, with n=0-20; $NH_2$—$(CH_2)_n$—$CO_2$H; $NH_2$—$CH_2$—$(CH_2$—O—$CH_2)_n$—$CO_2$H with n=1 to 10, linkers denoted A8 to A32 of document WO 2006/095234, pages 104 and 105;

a.2) P1-l-P2, which may be identical or different, P1 and P2 being chosen from O, S, NH, nothing, $CO_2$, NHCO, CONH, NHCONH, NHCSNH, $SO_2$NH—, $NHSO_2$—, squarate with l=alkyl, alkoxyalkyl, polyalkoxyalkyl (PEG), alkyl interrupted with one or more squarates or with one or more aryls, advantageously phenyls, alkenyl, alkynyl, alkyl interrupted with one or more groups chosen from —NH—, —O—, —CO—, —NH(CO)—, —(CO)NH—, —O(CO)— or —(OC)O—.

L will, for example, have a molecular weight of between 300 and 2000 g/mol, in particular between 300 and 1000 g/mol.

P1 and P2 are thus groups for coupling the linker with, firstly, the chelate and, secondly, the biovector.

3) Linkers described in U.S. Pat. No. 6,264,914, capable of reacting with amino, hydroxyl, sulfhydryl, carboxyl, carbonyl, carbohydrate, thioether, 2-amino alcohol, 2-aminothiol, guanidyl, imidazolyl or phenolic functional groups (of the biovector and of the chelate).

Groups capable of reacting with sulfhydryl groups include alpha-haloacetyl compounds of the type X—$CH_2$CO— (where X=Br, Cl or I), which can also be used for reacting with imidazolyl, thioether, phenol or amino groups.

Groups capable of reacting in particular with amino groups include:
  alkylating compounds: alpha-haloacetyl compounds, N-maleimide derivatives, aryl (for example, nitrohaloaromatic) compounds, aldehydes and ketones capable of forming Schiff's bases, epoxide derivatives such as epichlorohydrin, triazine derivatives containing chlorine that are highly reactive with respect to nucleophiles, aziridines, squaric acid esters, alpha-haloalkyl ethers.
  acylating compounds: isocyanates and isothiocyanates, sulfonyl clorides, esters such as nitrophenyl esters or N-hydroxysuccinimidyl esters, acid anhydrides, acyl azides, azlactones, imido esters. Groups capable of reacting with carboxyl groups include diazo compounds (diazo acetate esters, diazoacetamides), compounds that modify carboxylic acids (carbodiimides, for example), isoxazolium derivatives (nitrophenyl chloroformate, carbonyldiimidazoles, etc.), quinoline derivatives. Groups capable of reacting with guanidinyl groups include dione compounds such as phenylene diglyoxal or diazonium salts.

4) Certain linkers described in U.S. Pat. No. 6,537,520, of formula $(C r_6 r_7)_g$—$(W)_h$—$(C r_{6a} r_{7a})_{g'}$—$(Z)_k$—$(W)_{h'}$—$(C r_8 r_9)_{g''}$—$(W)_{h''}$—$(C r_{8a} r_{9a})_{g'''}$ with g+h+g'+k+h'+g''+h''+g''' other than 0;
  W chosen from O, S, NH, NHCO, CONH, CO, COO, OCO, NHCONH, NHCONH, $SO_2$, $(OCH_2CH_2)_s$; $(CH_2CH_2O)_{s'}$, $(OCH_2CH_2CH_2)_{s''}$, $(CH_2CH_2CH_2O)_t$;
  Z chosen from the group: aryl substituted with 0 to 3 $r_{10}$, $C_3$-$C_{10}$ cycloalkyl substituted with 0 to 3 $r_{10}$, a heterocycle system of 5-10 members containing 1-4 heteroatoms independently chosen from N, S and O, and substituted with 0 to 3 $r_{10}$;
  r6,r6a, r7, r7a, r8, r8a, r9 and r9a chosen independently from: H, =O, COOH, $SO_3H$, $PO_3H$, $C_1$-$C_5$ alkyl substituted with 0 to 3 $r_{10}$, aryl substituted with 0 to 3 $r_{10}$, benzyl substituted with 0 to 3 $r_{10}$, $C_1$-$C_5$ alkoxy substituted with 0 to 3 $r_{10}$, NHCO$r_{11}$, CONH$r_{11}$, NHCONH$r_{11}$, NH$r_{11}$, $r_{11}$, and a linker with the chelate;

$r_{10}$ chosen independently from: a linker with a chelate, COO$r_{11}$, OH, NH$r_{11}$, SO$_3$H, PO$_3$H, aryl substituted with 0 to 3 $r_{11}$, $C_1$-$C_5$ alkyl substituted with 0 to 1 $r_{12}$, $C_1$-$C_5$ alkoxy substituted with 0 to 1 $r_{12}$, and a heterocycle of 5-10 members containing 1-4 heteroatoms chosen independently from N, S and O, and substituted with 0 to 3 $r_{11}$;

$r_{11}$ is chosen independently from: H, aryl substituted with 0 to 1 $r_{12}$, a heterocycle with 5-10 members comprising 1-4 heteroatoms chosen from N, S and O, and substituted with 0 to 1 $r_{12}$, $C_3$-$C_{10}$ cycloalkyl substituted with 0 to 1 $r_{12}$, polyalkylene glycol substituted with 0 to 1 $r_{12}$, carbohydrate substituted with 0 to 1 $r_{12}$;

$r_{12}$ is a linker with the chelate;

with k chosen from 0, 1 and 2; h chosen from 0, 1 and 2; h' chosen from 0, 1, 2, 3, 4 and 5; h" chosen from 0, 1, 2, 3, 4 and 5; g chosen from 0, 1, 2, 3, 4, 5, 6, 7, 8, 9 and 10; g' chosen from 0, 1, 2, 3, 4, 5, 6, 7, 8, 9 and 10; g" chosen from 0, 1, 2, 3, 4, 5, 6, 7, 8, 9 and 10; g''' chosen from 0, 1, 2, 3, 4, 5, 6, 7, 8, 9 and 10; s chosen from 0, 1, 2, 3, 4, 5, 6, 7, 8, 9 and 10; s' chosen from 0, 1, 2, 3, 4, 5, 6, 7, 8, 9 and 10; s" chosen from 0, 1, 2, 3, 4, 5, 6, 7, 8, 9 and 10; t chosen from 0, 1, 2, 3, 4, 5, 6, 7, 8, 9 and 10.

5) Certain linkers described in document WO 02/085908, for example a linear or branched linker chain chosen from:
CR6'''R7'''—, —(R6''')C=C(R7''')=, —CC—, —C(O)—, —O—, —S—, —SO$_2$—, —N(R3''')—, —(R6''')C=N—, —C(S)—, —P(OO(OR3'''))—, —P(O)—(OR3''')O—, with R'''3 a group capable of reacting with a nitrogen or an oxygen;
a cyclic region (divalent cycloalkyls, divalent heterocycles);
polyalkylenes, polyalkylene glycols.

6) Linkers of document WO 03/011115, pages 124-125 in particular

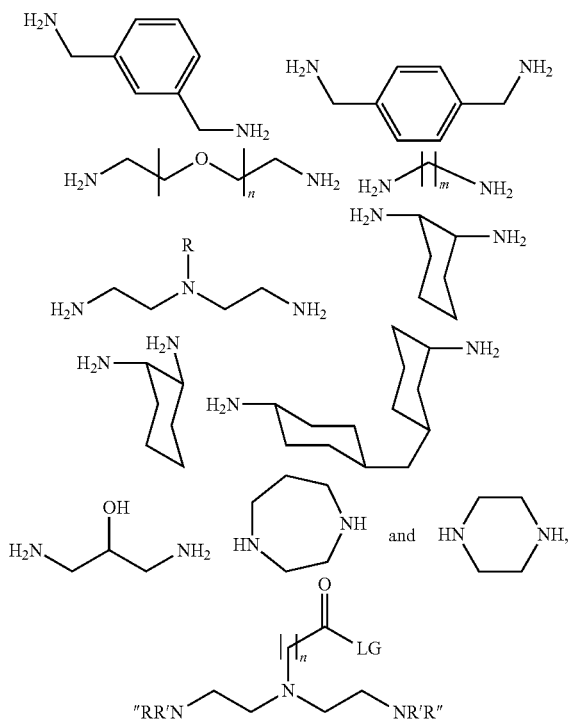

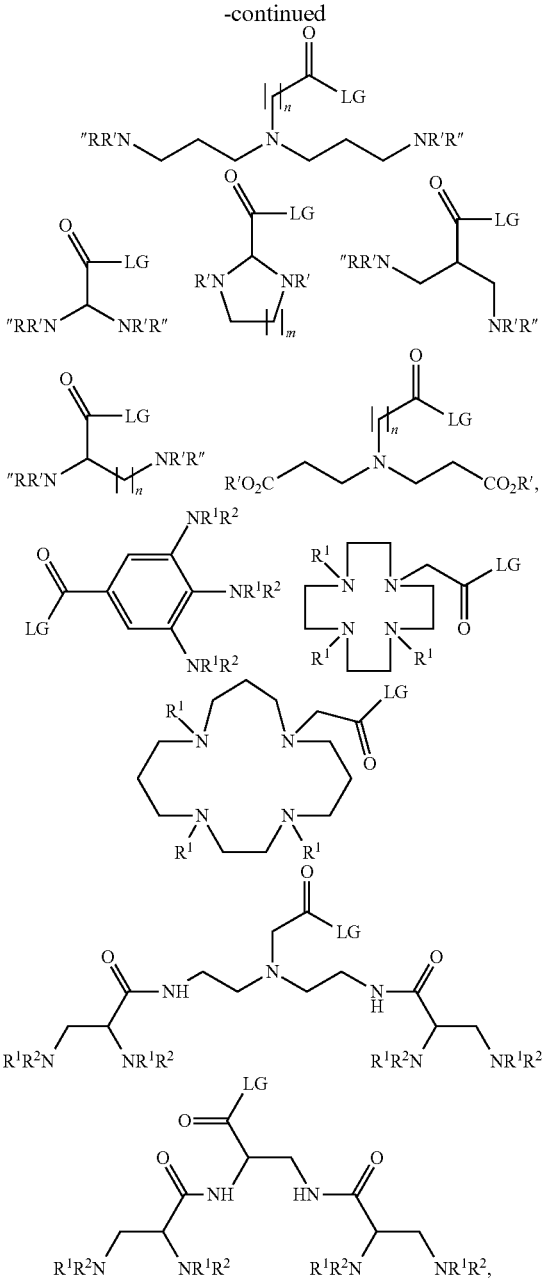

The choice of linkers (structure and size) may be made in particular in such a way as to control in particular the charge, the lipophilicity and the hydrophilicity of the product according to the desired diagnostic indication, so as to optimize the biological targeting and the biodistribution. Use may in particular be made of linkers that are biodegradable in vivo, PEG linkers or mini-PEG linkers. The invention relates in particular to the compounds comprising a linker such that the effectiveness of the compound prepared is equivalent to that of the compounds exemplified in detail in the present application, the activity being measured using appropriate in vitro and/or in vivo techniques.

For the chelate portion of the product, a large number of chelates may be used.

Use may in particular be made of a chelate of general formula below:

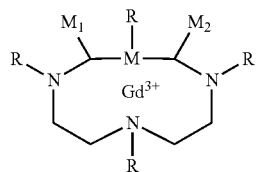

in which:
M-M1-M2 forms a pyridine ring;
or M1 and M2 are absent and M represents a bond;
or M is N—R and M1 and M2 represent a hydrogen atom or a methyl, with R chosen independently from $CH_2CO_2$— or H or CHX—$CO_2$—, with at least one R being $CHXCO_2$— and X being L-B;
and in particular a linear chelate chosen from: EDTA, DTPA diethylenetriaminopentaacetic acid, N-[2-[bis(carboxymethyl)amino]-3-(4-ethoxyphenyl)propyl]-N-[2-[bis(carboxymethyl)amino]ethyl]-L-glycine (EOB-DTPA), N,N-bis[2-[bis(carboxymethyl)amino]ethyl]-L-glutamic acid (DTPA-GLU), N,N-bis[2-[bis(carboxymethyl)amino]ethyl]-L-lysine (DTPA-LYS), monoamide or bisamide derivatives of DTPA, such as N,N-bis[2-[carboxymethyl[methylcarbamoyl)methyl]amino]ethyl]glycine (DTPA-BMA), 4-carboxy-5,8,11-tris(carboxymethyl)-1-phenyl-2-oxa-5,8,11-triazatridecan-13-oic acid (BOPTA).

Use may in particular be made of a macrocyclic chelate from 1,4,7,10-tetraazacyclododecan-1,4,7,10-tetraacetic acid (DOTA), 1,4,7,10-tetraazacyclododecan-1,4,7-triacetic acid (DO3A), 10-(2-hydroxypropyl)-1,4,7,10-tetraazacyclododecan-1,4,7-triacetic acid (HPDO3A) 2-methyl-1,4,7,10-tetraazacyclododecan-1,4,7,10-tetraacetic acid (MCTA), (alpha, alpha', alpha'', alph''')-tetramethyl-1,4,7,10-tetraazacyclododecan-1,4,7,10-tetraacetic acid (DOTMA) and 3,6,9,15-tetraazabicyclo[9.3.1]pentadeca-1(15),11,13-triene-3,6,9-triacetic acid (PCTA).

Use may also be made of derivatives in which one or more carboxylic groups is (are) in the form of a corresponding salt, ester or amide; or a corresponding compound in which one or more carboxylic groups is (are) replaced with a phosphonic and/or phosphinic group, such as 4-carboxy-5,11-bis(carboxymethyl)-1-phenyl-12-[(phenylmethoxy)methyl]-8-(phosphonomethyl)-2-oxa-5,8,11-triazatridecan-13-oic acid, N,N'-[(phosphonomethylimino)di-2,1-ethanediyl]bis[N-(carboxy-methyl)glycine], N,N'-[(phosphonomethylimino)di-2,1-ethanediyl]bis[N-(phosphonomethyl)glycine], N,N'-[(phosphinomethylimino)di-2,1-ethanediyl]bis[N-(carboxymethyl)glycine], 1,4,7,10-tetrsazacyclododecane-1,4,7,10-tetrakis[methylene(methylphosphonic)] acid, or 1,4,7,10-tetraazacyclododecane-1,4,7,10-tetrakis[methylene(methylphosphinic)] acid.

Use may also be made of a chelate from: DOTA gadofluorines, DO3A, HPDO3A, TETA, TRITA, HETA, DOTA-NHS, M4DOTA, M4DO3A, PCTA and their derivatives 2-benzyl-DOTA, alpha-(2-phenethyl)-1,4,7,10-tetraazacyclododecane-1-acetic-4,7,10-tris(methylacetic) acid, 2-benzylcyclohexyldiethylenetriamine-pentaacetic acid, 2-benzyl-6-methyl-DTPA, 6,6''-bis[N,N,N'',N''-tetra(carboxymethypaminomethyl)-4'-(3-amino-4-methoxyphenyl)-2,2':6',2''-terpyridine, N,N'-bis(pyridoxal-5-phosphate)ethylenediamine-N,N'-diacetic acid (DPDP) and ethylenedinitrilotetrakis(methylphosphonic) acid (EDTP).

More widely, the chelate(s) forming the single entity may correspond to the formula of document WO 01/60416.

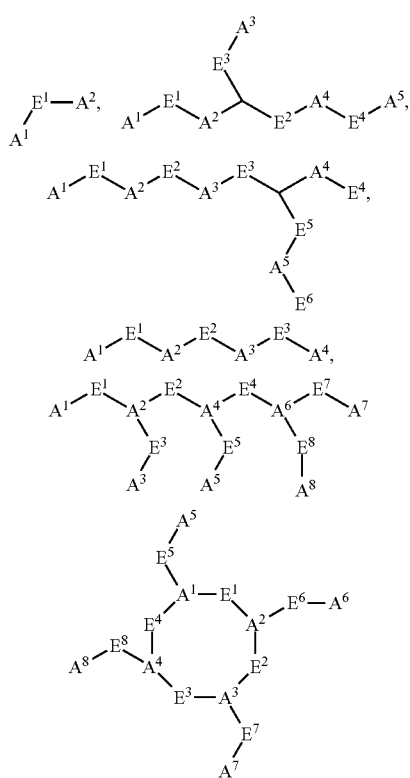

Use may in particular be made of the compounds DTPA, DOTA, NOTA and DO3A, and derivatives, in particular:

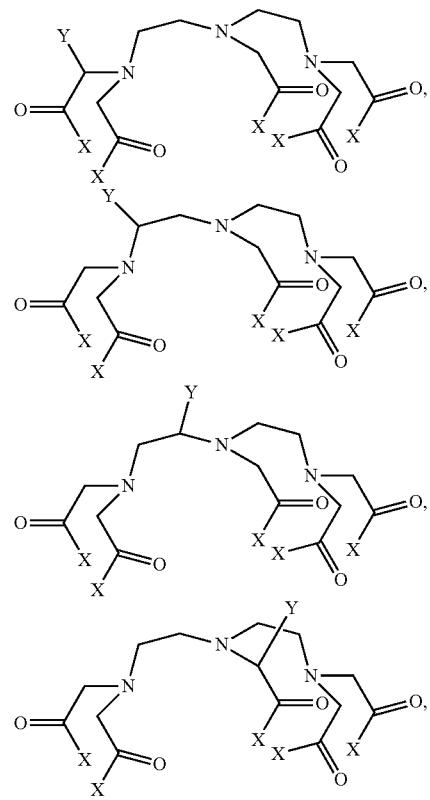

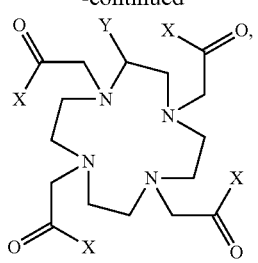
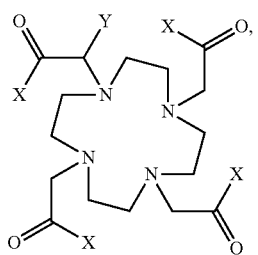
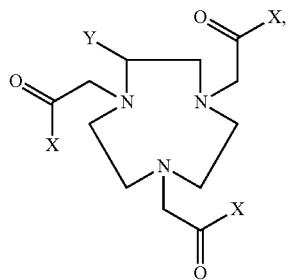
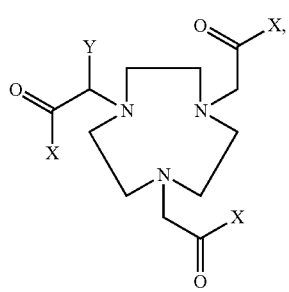
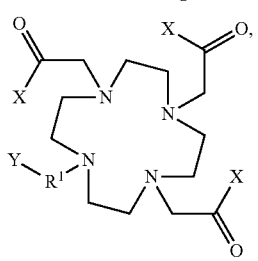
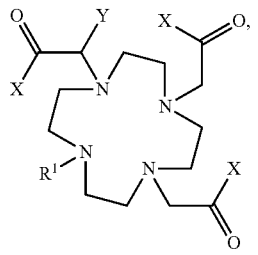
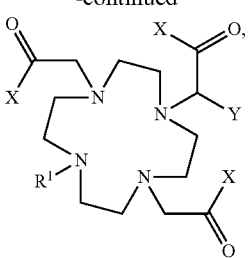
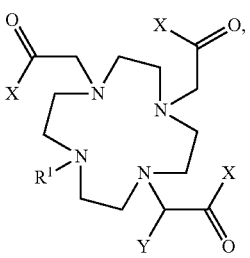
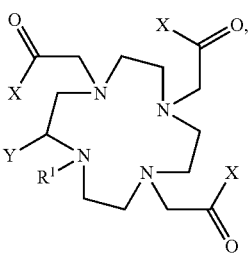
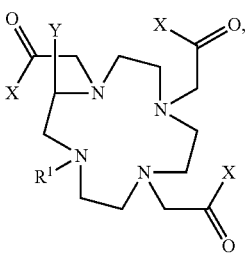
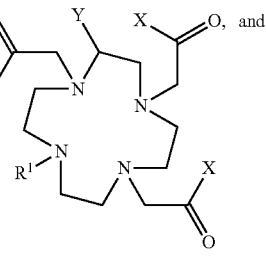
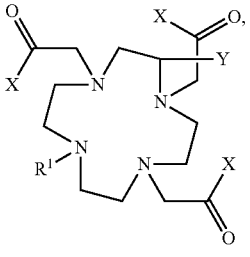
with X a group capable of coordinating a metal cation, preferably O—, OH, $NH_2$, $OPO_3$— or NHR, with R an aliphatic chain.
Use may in particular be made of the chelates denoted P730 from the applicant, in particular of formula V and VI of document EP 661279 (U.S. Pat. No. 5,919,432), especially

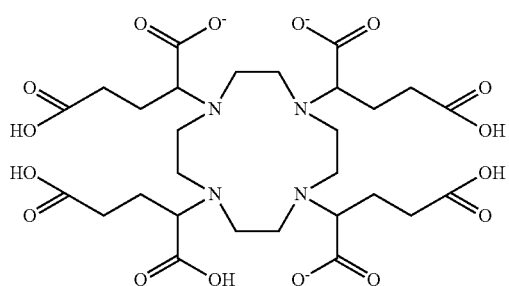 [SMILES: O=C(O)CCC(C(=O)[O-])N1CCN(C(CCC(=O)O)C(=O)[O-])CCN(C(CCC(=O)O)C(=O)O)CCN(C(CCC(=O)O)C(=O)[O-])CC1]

the preparation of which is precisely described in particular on pages 26 to 32, and the chelates with a PCTA scaffold described by the applicant in particular in U.S. Pat. No. 6,440,956, whether or not these chelates or their intermediates carry hydrophilic chains, and in particular short or long amino alcohol chains.

Mention will also be made of the chelates recalled in WO 03/011115, pages 8 to 11, in particular

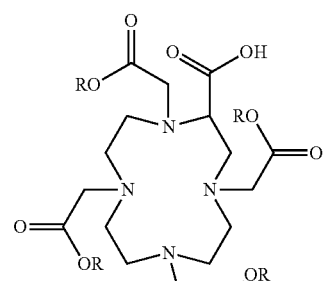

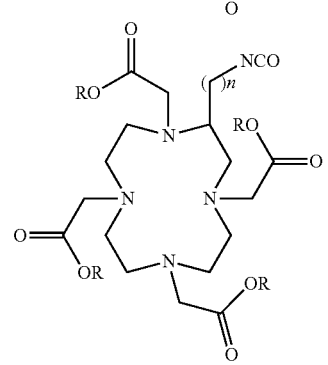

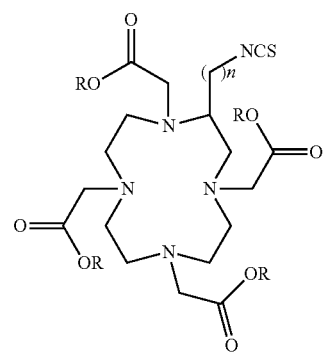

-continued

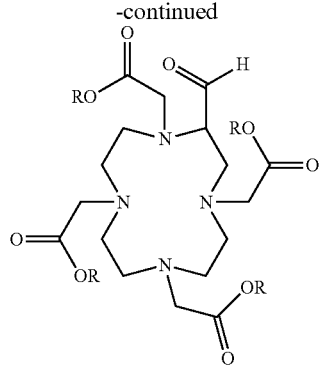

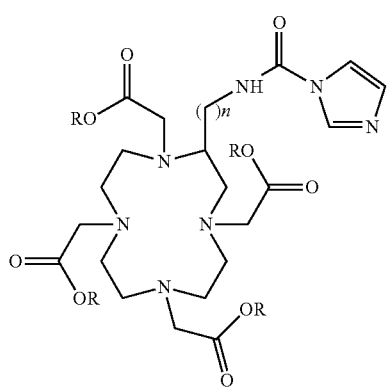

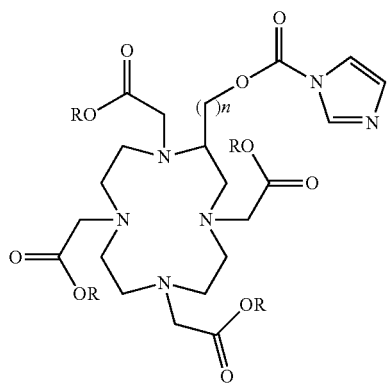

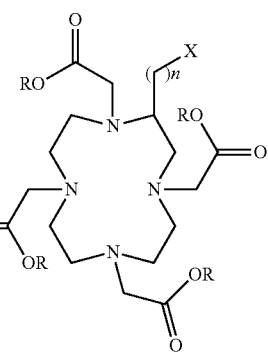

-continued
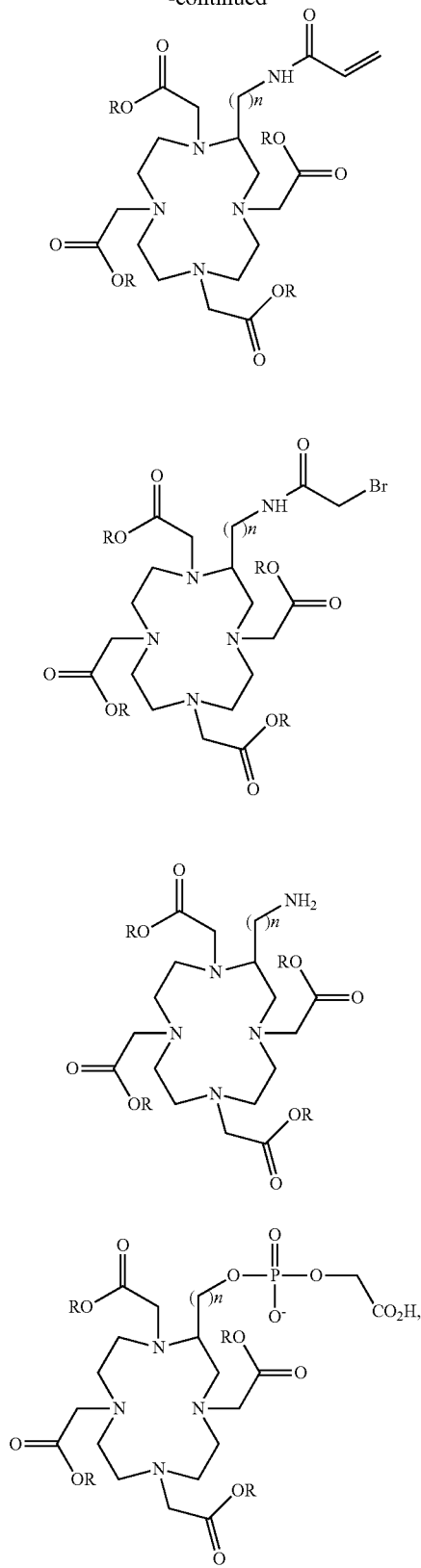
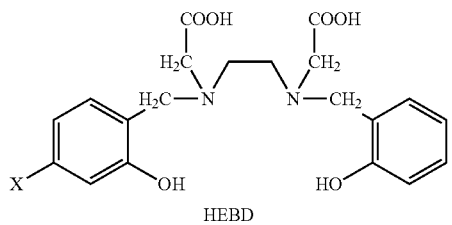
Desferrioxamine-B (DFO)
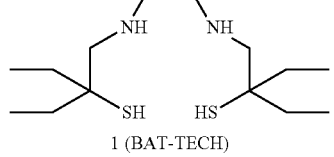
HEBD
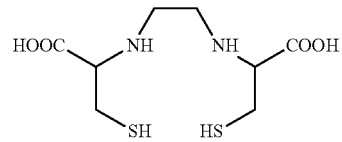
1 (BAT-TECH)
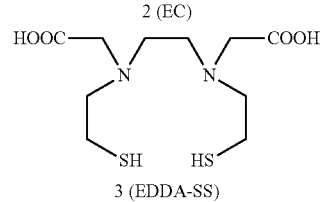
2 (EC)
3 (EDDA-SS)
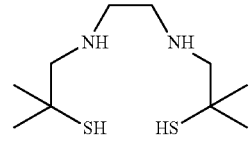
4 (4SS)
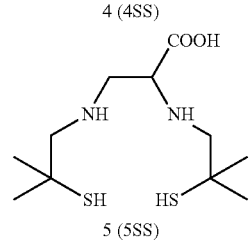
5 (5SS)
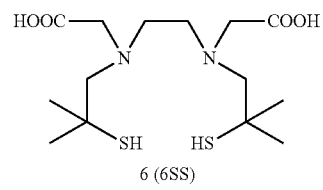
6 (6SS)
Use may also be made of the improvements of the following compounds already mentioned for the coupling with gallium (HED, IDA (iminodiacetic acid), desferroxamine).

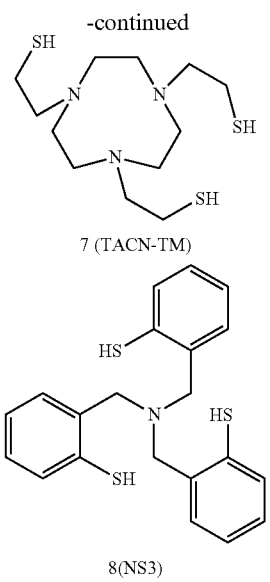

7 (TACN-TM)

8(NS3)

Use may also be made of chelates described in Inorg. Chim. Acta (1995), 75-82 (TACN-TM (1,4,7-tris(2-mercaptoethyl)-1,4,7-triazacyclononane)), and Bioconj. Chem. (2002), 1140-1145 (tripodal trithiolate chelate) and, in general, any chelate capable of forming a sufficiently stable cage around $Ga^{3+}$, in particular any aliphatic macrocyclic or linear amine, or amine macrocycle with tertiary amines.

The applicant has focused most particularly on chelates capable of complexing gallium and having at least one function for coupling the chelate to at least one biovector.

For the choice of the chelates, use may be made of chelates that are particularly suitable for coupling gallium, in particular chelates for which the value of log K is quite high (log K=ML/(M)(L) with M the metal and L the ligand which is the chelate or the conjugate [chelate+biovector]), and in particular of which the structures makes it possible to form a highly protective box for the $Ga^{3+}$. Use may in particular be made of complexes such that the log K is of the order of 20 to 40, in particular of 25 to 35. Where appropriate, use will be made of a macrocycle carrying, in addition to the three negatively charged acid functions coupled to the $Ga^{3+}$, at least one protective group for the $Ga^{3+}$. The term "protective group" is intended to mean a group capable of protecting or improving the coordination of $Ga^{3+}$ with the functions of the chelate (COOH functions, for example). Insofar as the amount of chelate injected into the patient is very small, it is possible to use chelates with quite a complex structure intended to provide protection for the $Ga^{3+}$, for example by assembly of linear or macrocyclic chelates.

Complexes that are more stable than the gallium III-transferrin complex (log K=20.3) will in particular be chosen.

However, since the lifetime of the product is very short (approximately 1 to 2 hours between the time it is synthesized and the PET meaning), chelates for which the log K is much lower but sufficient for the desired reading could be chosen, taking into account, where appropriate, Ga68-transferrin interaction data.

The experimental results for PET imaging with Ga68 show the advantage of sufficiently distancing the chelate portion from the biovector portion. For this, quite a large linker may be chosen. Conversely, it is possible to use biovectors that are small in size, but such that the recognition of the biovector by its target is not altered in an impairing manner. In particular, according to one embodiment, the recognition specificity is tested with linkers comprising 1 to 5 amino acids. Complexes (biovector-chelate-$Ga^{3+}$) whose target-specificity is better using gallium rather than technicium or indium are thus studied, the difference in affinity for the target probably being due to a difference in conformation of the complex according to the radionuclide.

Chelates in which one or more functions not linked to the biovector are coupled with at least one group intended to improve the recognition of the biovector for its target have also been studied; for example, a group which decreases renal clearance, a group which interacts with a target in the vicinity of the biological target (for example, this group stabilizes the structure of the biovector recognition site), or a group which modifies the pH, the charge or other physicochemical parameters such as the hydrophilicity or the lipophilicity, so as to improve the affinity of the biovector for its target and/or to increase the modification of the biovector if it involves a substrate for an enzyme or an intra- or extracellular effector, is used.

The applicant has also studied multivalent systems of the type:
microemulsions (lipid nanoparticles) for specific targeting, comprising chelates of gallium and a biovector for specific targeting, for example for the targeting of integrines;
nanoparticles coated with a covering of Ga68 chelate and biovector; mention will in particular be made of superparamagnetic particles of iron oxide of the type USPIO and SPIO, and quantum-dot compounds, the surface of which is suitable for this covering of the chelate and of the biovector.

Insofar as the preparation of the Ga68 in the generator is accompanied by the release of impurities, the applicant has also studied compounds of which the chelate is capable of complexing Ga68 but not the possible residual impurities in the Ga68 solution that has left the generator.

The applicant has, moreover, studied formulations of the gallium-labeled vectorized compounds. These formulations comprise, firstly, at least one gallium-labeled vectorized compound, each vectorized compound comprising at least one biovector coupled to at least one Ga68-complexing chelate, and, secondly, at least one additive for stabilizing the vectorized compound. In particular, given the kinetics and the stability of the complexation of the Ga68 by the chelate, it may be the case that Ga68 is not optimally complexed by the chelate of the chelate-biovector-Ga68 compound, hence a risk of free Ga68 in the product injected into the patient.

To this effect, the formulation administered to the patient comprises, as stabilizing additive, an excess of chelate capable of complexing the free Ga68. The excess chelate may be the same as the chelate of the vectorized compound, or a different chelate, provided that it is suitable for complexing the free Ga68. For example, the chelate of the vectorized compound will be a macrocyclic chelate that is particularly advantageous for gallium chemistry, while the excess chelate in the formulation will be a linear chelate that is simpler to manufacture. By virtue of such a formulation, it will be possible in particular to compensate for the product purity or stability difficulties derived from the rapid preparation process selected. It will thus be possible to use a method for coupling the biovector and the chelate of the product, for example by heating, which is rapid (less than 20 minutes, for example) but which causes a risk of relative instability of the complexation of the Ga68 by the chelate, this risk being, however, compensated for by the addition of excess chelate to this product. Thus, the formulation comprises a compound according to the invention (i.e. a metal complex of gallium Ga68 of formula Ch-L-B or Ch-Lp-Bq) and a noncomplex linear or macrocyclic chelate Ch, advantageously present at a concentration of from 0.01 to 100 mM, advantageously from 10 to 100 mM.

The formulation may also be an ionic formulation, in particular of calcium. In fact, advantageously, the calcium can bind to the excess free chelate that may be present in the formulation or in the patient's body. The general principle is to respond to a particular technical problem derived from the use of Ga68 for preparing vectorized compounds, in particular due to the intention of preparing a compound rapidly, which may not allow optimal purification or stabilization of the product. Such a formulation will, for example, make it possible to overcome the existence of by-products or of excess reactants such as amines or acids.

Use may also be made of various formulation mixtures, for example, described in WO 2005009393 for the stabilization with respect to radiolysis in particular of biovectors (examples: free-radical blockers, dithiocarbamates, PDTC, soluble compounds with selenium, such as selenomethionine, selenocysteine with, where appropriate, sodium ascorbate, derivatives capable of reducing oxidized amino acids such as methionine, in particular thiol derivatives of cysteine, mercaptoethanol, dithiothreitol). Use may also be made of formulations of arginine, lysine, polylysine and other cationic amino acid derivatives for limiting renal reabsorption.

The applicant has also investigated biovectors and chelates such that their coupling with gallium is sufficiently efficient and rapid.

For example, document WO 2004/089425 describes a microwave process for improved synthesis and improved purity of the product which incorporates the biovector and the chelate coupled to Ga68. The applicant has examined the use of biovectors likely to be sensitive to the microwave treatment. In particular, a screening method consists in testing the stability of biovectors of diagnostic interest subsequent to microwave treatment.

There remains the need to develop processes and devices that make it possible:
  to reduce the preparation time and to improve the stability of the product, in particular for microwave-unstable biovectors;
  to improve the purity of the product;
  to increase the concentration of the product;
  to improve the safety of the patient, in particular by means of a preparation under appropriate sterility conditions.

The applicant has thus taken an interest most particularly in processes (thermal, physicochemical, chemical, etc.) and devices, optionally already used or that can be used in nuclear medicine for isotopes other than gallium, and the adaptation of which is appropriate in the case of Ga68 in order to solve these problems.

Ga68 is obtained by decay of Ge68, the lifetime of which is 270 days. Ge68 generators are based on the use of a matrix which absorbs the Ge68, the Ga68 being eluted. However, in known generators, a step to concentrate the Ga68 is necessary since the eluted volume is too dilute. The applicant has studied means for concentrating the eluate and/or for reducing the volume of the eluate, in particular by improving the matrix used. The applicant has also studied the means of purifying the eluant so as to remove its impurities ($Ti^+$ in particular) capable of hindering the coupling with the chelate, and of automating the concentrating/purifying step, for example by means of chromatography columns, using a device that is integrated or at the generator outlet. When the Ga68 leaves the generator, it can be coupled to the chelate, the complex formed being intended to be coupled to the biovector portion. According to one variant, the chelate has been coupled to the biovector beforehand, so that this coupling reaction does not impair the stability of the chelate with gallium. Where appropriate, the preparation of the product comprises a step of eliminating the excess gallium which has not been complexed by the product. Where appropriate, the Ga68 solution is made less acidic in order to facilitate the coupling with the chelate. In particular, processes for coupling, lasting less than 20 minutes, between, firstly, the Ga68 that has left the generator and, secondly, the biovector+chelate compound have been studied, the coupling conditions being such that the degree of complexation of the Ga68 by the chelate of said compound is more than 50%, preferably more than 70%, 80%, 90%, for example:
  very rapid heating at high temperature without impairing the structure of the biovector, then rapid cooling;
  no heating, but addition of a catalyst;
  heating for less than 10 minutes at 50° C., for example between 70 and 100° C., an excess of chelate being added in order to chelate the Ga68 not complexed by the biovector+chelate compound.

In addition to the microwave processes, use may be made of any type of activation process, such as processes with ultrasound and clay.

Furthermore, the applicant has been able to obtain stable Ga68-complexing compounds as described in detail below with rapid heating at about 80° C. for 5 minutes, without this requiring microwaves.

The applicant has also studied the use of appropriate chelates for a process of coupling the chelate and the biovector under conditions which are not optimal but which are sufficient for the desired reading. For example, the coupling process comprises heating at a temperature lower than the optimal temperature, but sufficient for an effective PET reading.

Chelates which are such that their coupling with Ga68 is very rapid and does not require a physical and/or chemical treatment that impairs the biovector have also been most particularly studied. This is intended to select chelates which are highly advantageous with respect to this process criterion (rapidity of coupling), provided that the gallium-complexing of said chelates is sufficient for the use in PET imaging of Ga68.

It has also been sought to optimize the dose of gallium so as to limit the dose of radiation given to the patient, while at the same time obtaining good product effectiveness. Since the patient's exposure time is much shorter than with radionuclides with quite a long lifetime, such as technicium or indium, the dose of product with gallium injected may thus be much higher than with these radionuclides. The applicant has thus studied compounds that are effective at a dose of radioactivity of the order of 1 to 1000 Curie/mol, in particular 1 to 10, 1 to 100, or even more than approximately 2000 to 3000 Curie/mol. It will also be possible to carry out several series of measurement, for example at a radioactivity dose of the order of 0.1 to 1000 Curie/mol per measurement, in the same patient imaging session. The radioactivity of the product is, for example, between 100 and 1000 MBq/nmol.

According to one embodiment, a kit comprising the gallium ligand, i.e. the chelate, to be coupled to the biovector or already coupled to the biovector, is used. The radiopharmacist adds, to this gallium ligand, the sterile gallium solution that has left the generator.

In order to improve the sterility of the device and, where appropriate, to meet CGMP standards, it is possible to lyophilize the ligand (biovector coupled to the chelate), which is dissolved (for example using sterile water and a buffer such as sodium acetate), and the resulting solution is added to the gallium solution by the radiopharmacist. Other methods of preparing the ligand may be carried out, the principle being to obtain a solution of ligand, the desired parameters of which (stability, reactivity with gallium, sterility, etc.) are suitable for gallium complexation. For example, for ligands that provide constraints of poor water-solubility with the risk of precipitation, DMSO and suitable excipients can be used.

As regards the generator itself, devices are sought which improve miniaturization and sterility, as described in WO 2005/084168, for example with the solution of gallium leaving the generator being collected in a presterilized empty packaging, the packaging filled with the Ga68 solution then being used with the administration kit comprising the ligand. In particular, it is sought to ensure sterility of the generator throughout its lifetime, which is close to that of germanium, therefore approximately one year. Suitable generators may also be of the Ti 44/SC44 type.

Automated and preferably sterile systems comprising, for example, the following are also studied:
- a part for producing the Ga68 (Ga68 generator producing a solution of Ga68, and, where appropriate, concentrating means, means for sterilizing the solution of Ga68, means for collecting the sterile solution of Ga68);
- a part for coupling the solution of Ga68 with the Ga68 ligand (biovector+chelate), at the outlet of which the solution of product to be injected into the patient is collected; where appropriate, this part comprises a solution of stabilizing additives (pH, excess chelate, protective groups, etc.) and heating/cooling means;
- where appropriate, a part for administering the solution of product ready for injection.

The preparation process preferably includes an aspect of radioprotection of individuals, which is obtained, for example, by using appropriate packaging devices and/or injection devices (syringes, for example).

As regards more particularly the methods of imaging of the compounds studied, the PET imaging with Ga68 may, moreover, be coupled with certain specific methods of MRI imaging.

In particular, the combination of PET (or PET CT with PET for the functional imaging and the CT scan for the anatomical imaging) and of MRI makes it possible to combine the very high sensitivity of PET (but which has a resolution which is not as good as MRI) with the very high resolution of MRI (but which has a sensitivity which is not as good as PET). In order to improve the contrast, at least one contrast product for PET, preferably with Ga68, which makes it possible to detect all the tumor zones and metastases over the entire body, and at least one contrast product for MRI intended to visualize with a high resolution one or more zones detected with the PET, may be administered simultaneously or with a delay between them. In certain indications, other gallium isotopes may be preferred.

Automated processes will be particularly advantageous for such an imaging combination, in order to optimize the administration, the reading and the image analysis, using, where appropriate, automatic contrast product injection devices. It will be possible, for example, according to the results of the PET detection, to automatically zoom into one or more zones of interest pinpointed with the PET, with or without the injection of contrast product. For example, a specific contrast product vectorized for PET with Ga68 and a contrast product vectorized for MRI with gadolinium may be used, the biovectors being identical or different, with for example the biovector of the PET product being capable of localizing an angiogenesis in all tumors, and the biovector of the MRI product being capable of studying with precision the localization and/or the characterization of the progression of specific tumoral zones in various biological territories.

The invention thus also relates to an imaging method comprising:
a) the administration of at least one Ga68 contrast product for detecting by PET imaging at least one zone of diagnostic interest;
b) the administration of at least one contrast product for MRI or XR scan, intended to specifically analyze the zone(s) of diagnostic interest detected in a).

Conversely, if an XR or MRI contrast product is effective in a diagnostic indication, the diagnosis may be refined using a Ga68 product.

The invention thus also relates to an imaging method comprising:
a) the administration of at least one contrast product for MRI or XR scan capable of performing a first analysis of a diagnostic zone of interest;
b) the administration of at least one radiolabeled Ga68 contrast product for performing a second analysis of the diagnostic zone of interest or of a zone wider than the zone of interest.

As MRI contrast product, use may also be made of a nonvectorized BPA (blood pool agent) product for analyzing tumor zones with precision through high resolution.

As MRI contrast product, use may also be made of superparamagnetic particle compounds, especially USPIO, and especially all those indicated in WO 2004058275 and application WO 2005046563 (pages 5 to 9), and in particular comprising an iron oxide core coated with dextran or with any dextran derivative.

As CT scan contrast product, use may be made of radioisotopes for CT, known iodinated products, such as a monomer, a dimer which may be ionic or nonionic, or a mixture of a monomer and of a dimer which is nonionic. Use may also be made of products such as liposomes of XR or MRI products, for instance of iohexol or of gadoteridol, described in particular in Investigative radiology, vol 41, No. 3, 339-348, 2006. According to one embodiment, a diagnostic composition comprising at least one gallium contrast agent detectable by PET as described in the application and at least one contrast agent detectable by MRI or at least one contrast agent detectable by CT scan will be prepared. According to one embodiment, a superparamagnetic product of the USPIO type and a product that can be used for X-rays, such as an ionic or nonionic iodinated monomer or dimer, will be used in combination.

Advantageously, it is also possible to use, by coadministration (simultaneously or with a delay between administrations), an agent capable of increasing the tumor-accessibility of a contrast product, in particular a Ga68 contrast product, and/or the time spent by the contrast product in passing through the tumor. Such agents can, for example, act by increasing the vascular permeability in the tumor zone (peripheral and/or intratumoral) so as to cause the contrast product to penetrate further into the tumor, or by a decrease in the pressure of the interstitial fluids in the tumor (the contrast product has more time to penetrate into the tumor). Use is in particular made of "stealth" agents capable of acting very rapidly on these mechanisms, and eliminated rapidly from their zones of action, thereby allowing both an improvement in diagnosis and nontoxicity.

Tumor PET imaging can also be coupled with diffusion imaging or perfusion imaging studying the differences in diffusion or the perfusion of compounds or in diffusion of water in afflicted/normal zones, by involving, where appropriate, PET or MRI contrast products.

The following steps will, for example, take place:
optional first scan or MRI measurement, before injection of contrast product;
PET measurement following injection of a gallium contrast product;
analysis of the PET data in order to identify zones of interest, in particular pathological zones for which the diagnosis may be investigated more thoroughly;
in a programmed manner or depending on this analysis, injection of gadolinium contrast product for MRI, in one or more zones of interest;
MRI measurement following injection of contrast product for MRI;
optional further administration of contrast product.

In order to optimize the flow rate and the dose of contrast product to be injected, it will be possible to use and parameterize an automatic injector which is capable of integrating the results of the analysis of the data from a prior measurement carried out with or without contrast product and of optimizing the flow rate and the dose of contrast product.

More specifically, use will, for example, be made of a PET/MRI or PET/CT or PET/CT/MRI installation comprising:
a PET module capable of performing PET measurements;
where appropriate, an MRI module capable of performing MRI measurements;
where appropriate, a CT module capable of performing CT measurements;
an analytical module comprising, firstly, a module for receiving the data from the signal emitted by the measuring module (PET, MRI, XR scan, etc.) following a measurement with or without administration of contrast product, and, secondly, a module for processing these data, capable of converting these data into a signal for controlling one or more injectors by giving them instructions regarding the contrast product administration parameters;
one or more injectors comprising a module for receiving the instructions from the analytical module, and an injection module controlled by the receiving module and connected to the patient in order to administer to the latter the appropriate contrast product dose.

Among the data analyzed by the analytical module, mention will be made of the enhancement curves and the measurements of relaxivity linked to the diagnostic indication studied, physicochemical parameters, biological data from the patient that may have an impact on the injection.

The analysis may be carried out, for example, in comparison with behavioral models of the contrast products as a function of the category of product used, and, where appropriate, by means of confidence indices associated with calculated parametric maps.

These data are, for example, compared to an internal database of the installation which exploits the results obtained by means of clinical data compilation software.

It is also possible to study combining MRI or CT anatomical information with PET functional imaging information during the image analysis, the analysis being related to the volume of the anomaly.

According to one aspect, the invention thus relates to an automated system comprising a device for preparing an injectable solution of gallium contrast product, an administration component for administering said solution and, where appropriate, means for controlling this administration as a function of biological data or of imaging data from the patient.

The invention also relates to a medical imaging installation (and the associated imaging process) comprising:
an imaging device capable of performing measurements of imaging parameters with or without injection of contrast product;
a device for injecting a contrast product, connected to the patient, it being possible for the device to be an automatic syringe or bag injector;
where appropriate, a device for analysis and for controlling the injection device according to a first measurement performed following the administration of a contrast product, in particular when the contrast product is a radiolabeled gallium product.

The device is of PET/CT, PET/MRI or PET/CT/MRI type.

Where appropriate, an MRI and/or CT scan measurement is performed using an appropriate contrast product, and then a PET measurement is performed with the gallium product.

The detailed description which follows describes examples of appropriate compounds, in particular metal complexes of gallium of formula:

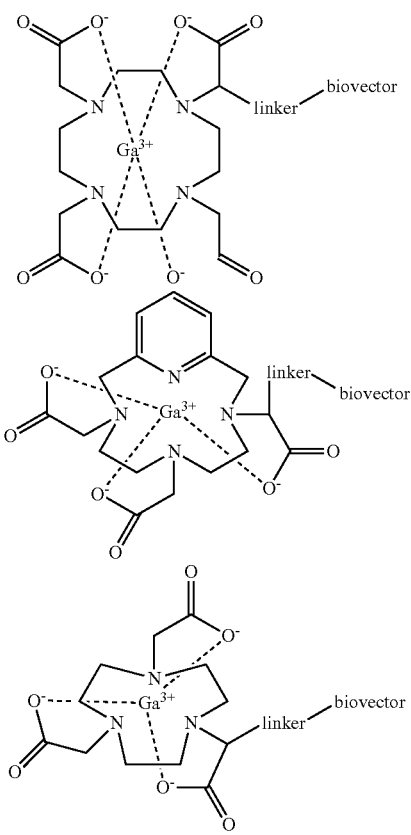

with:
biovector a pharmacologically active molecule, in particular a peptide;
linker chosen from: $(CH_2)_n$, $(CH_2)_n$—CO—, PEG,

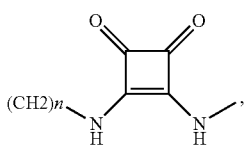

squarate coupled with PEGs, with n=1 to 5, advantageously n=2 to 5, n=4 or 5, so as to advantageously obtain several lengths and types of linkers advantageous for the physicochemistry and/or the biodistribution.

The invention relates to a metal complex of gallium Ga68 of formula Ch-L-B (chelate-linker-biovector), or Ch-Lp-Bq with p=q=2 to 5, Ch being a chelate chosen from the scaffolds DTPA, DOTA, NOTA, DO3A and PCTA, and derivatives thereof, and having the following general formula:

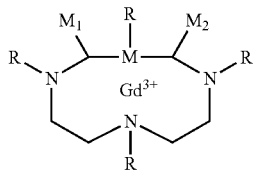

in which:

M-M1-M2 forms a pyridine ring;

or M1 and M2 are absent and M represents a bond;

or M is N—R and M1 and M2 represent a hydrogen atom or a methyl, with R being chosen independently from CH$_2$CO$_2$— or H or CHX—CO$_2$—, with at least one R being CHXCO$_2$— and X being L-B;

in particular the complexes of formulae:

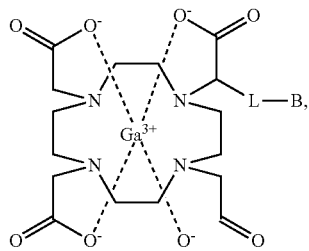

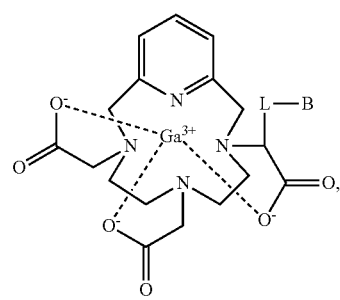

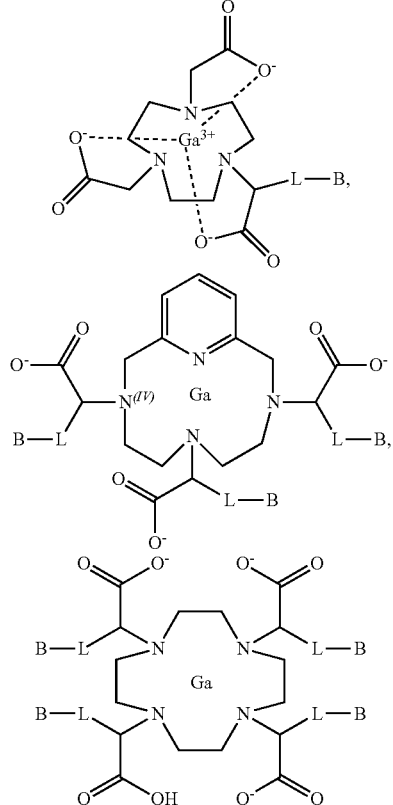

in which:

1) B is a biovector for targeting a biological target associated with a pathology, in particular chosen from enzymes (metalloproteases, COX, tyrosine kinase), cell receptors VEGF, KDR, CXC, LHRH, GPIIb/IIIa, bombesin/GRP, gastrin, VIP, CCK, GLUT and folate;

2) L is a linker chosen from:
 a) P1-l-P2, with P1 and P2, which may be identical or different, being chosen from O, S, NH, CO$_2$, —NHCO, CONH, NHCONH, NHCSNH, SO$_2$NH— and NHSO$_2$—,
  and l representing an alkyl (advantageously C$_1$-C$_{10}$), alkoxyalkyl (advantageously C$_1$-C$_{10}$), polyalkoxyalkylene, alkyl interrupted with one or more squarate(s) or with one or more aryl(s), advantageously phenyl, or alkenyl (advantageously C$_1$-C$_6$), alkynyl (advantageously C$_1$-C$_6$), or alkyl interrupted with one or more groups chosen from —NH—, —O—, —CO—, —NH(CO)—, —(CO)NH—, —O(CO)—, or —(OC)O—;
 b) (CH$_2$)$_n$, (CH$_2$)$_n$—CO—, —(CH$_2$)$_n$NH—CO— with n=2 to 10, (CH$_2$CH$_2$O)$_q$(CH$_2$)$_r$—CO—, (CH$_2$CH$_2$O)q (CH$_2$)$_r$—NH—CO— with q=1-10 and r=2-10, (CH$_2$)$_n$—CONH—, (CH$_2$)$_n$—CONH-PEG, (CH$_2$)$_n$—NH—,

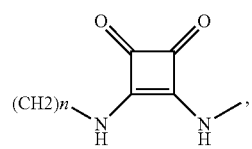

31

-continued

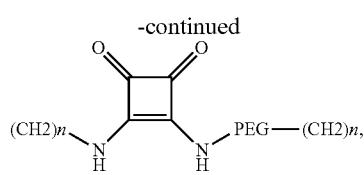

with n=1 to 5 and advantageously n=4 or 5, HOOC—CH$_2$—O—(CH$_2$)$_2$—O—(CH$_2$)$_2$—O—CH$_2$—COOH; HOOC—

32

(CH$_2$)$_2$—CO$_2$—(CH$_2$)$_2$—OCO—(CH$_2$)$_2$—COOH; HOOC—CH(OH)—CH(OH)—COOH; HOOC—(CH$_2$)$_n$—COOH; NH$_2$—(CH$_2$)$_n$—NH$_2$, with n=0-20; NH$_2$—(CH$_2$)$_n$—CO$_2$H; NH$_2$—CH$_2$—(CH$_2$—O—CH$_2$)$_n$—CO$_2$H with n=1 to 10.

Advantageously, these compounds according to the present invention are chosen from the compounds of formulae below:

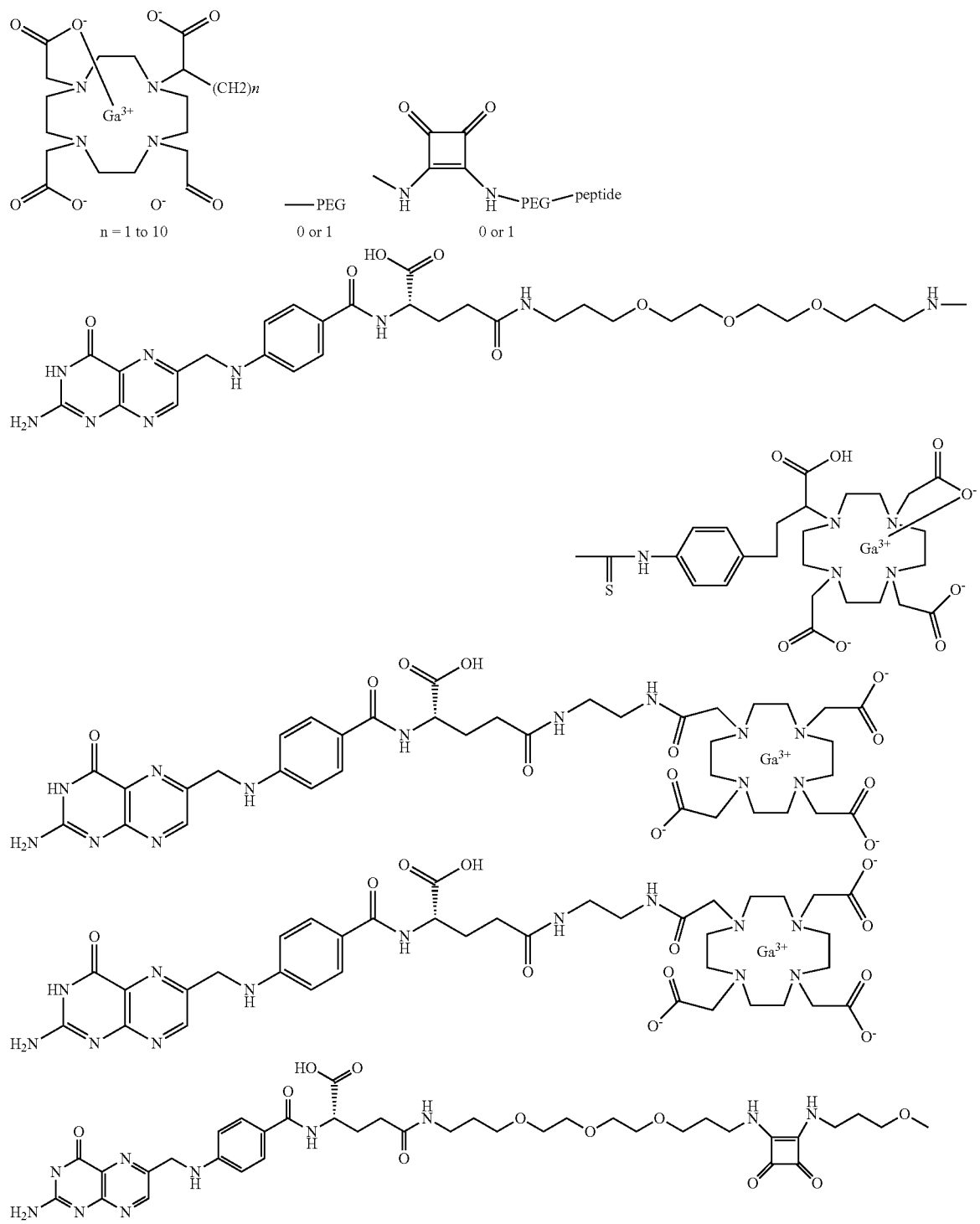

-continued

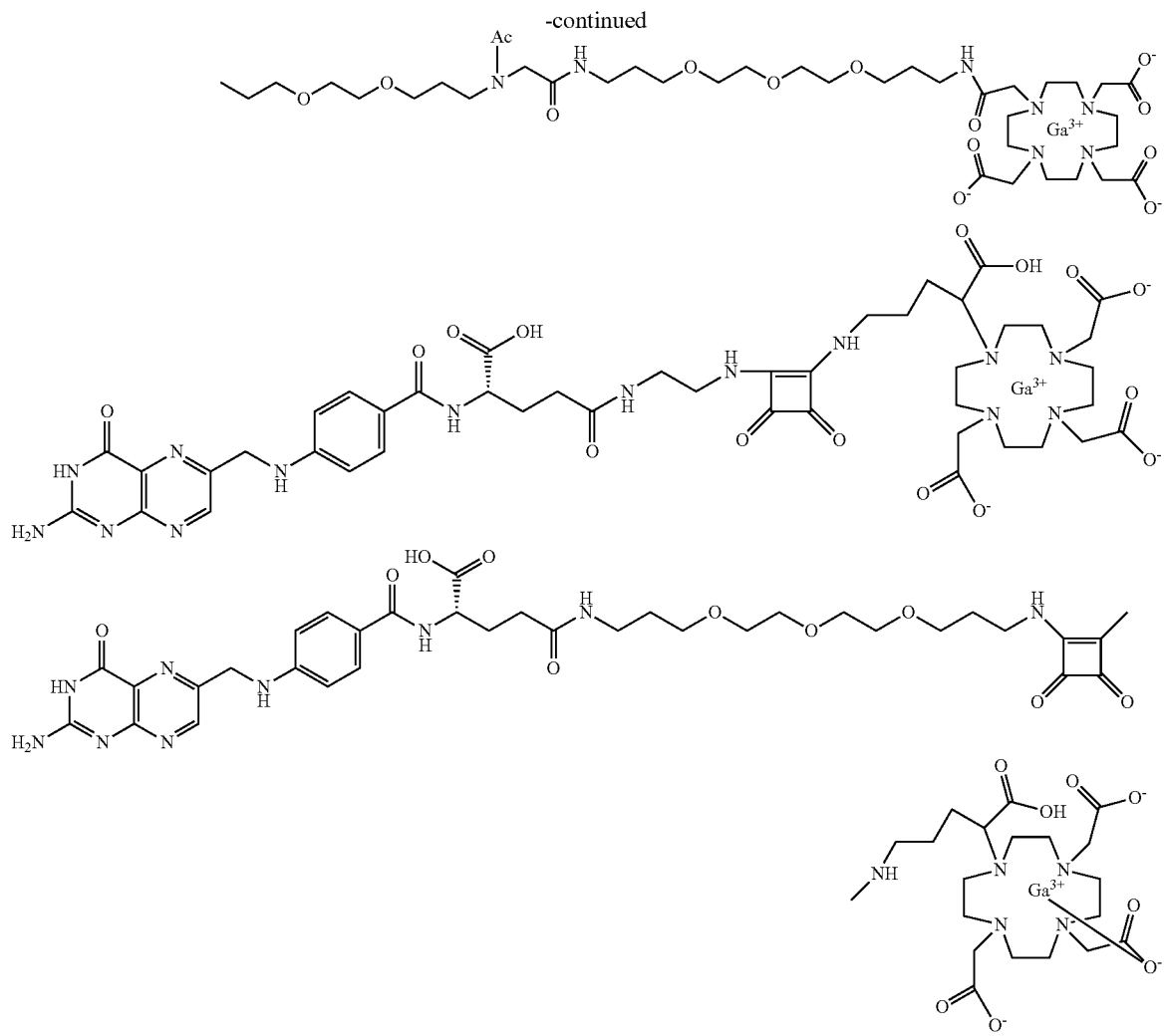

For the purpose of the present invention, the expression "alkyl group, advantageously $C_1$-$C_{10}$" is intended to mean any alkyl group advantageously containing from 1 to 10 linear or branched carbon atoms, in particular methyl, ethyl, n-propyl, isopropyl, n-butyl, isobutyl, sec-butyl, t-butyl, n-pentyl and n-hexyl groups. Advantageously it is a methyl group.

For the purpose of the present invention, the expression "alkenyl group, advantageously $C_2$-$C_6$" is intended to mean any alkenyl group advantageously containing from 2 to 6 linear or branched carbon atoms, in particular the vinyl group. For the purpose of the present invention, the expression "alkynyl group, advantageously $C_2$-$C_6$" is intended to mean any alkynyl group advantageously containing from 2 to 6 linear or branched carbon atoms, in particular an ethynyl group.

For the purpose of the present invention, the expression "alkoxy group, advantageously $C_1$-$C_{10}$" is intended to mean any alkoxy group advantageously containing from 1 to 10 linear or branched carbon atoms, in particular the $OCH_3$ group.

For the purpose of the present invention, the term "aryl group" is intended to mean one or more aromatic rings containing from 5 to 8 carbon atoms, that may be attached or fused, optionally substituted with halogen atoms, alkyl groups as defined above or the nitro group. In particular, the aryl groups may be monocyclic or bicyclic groups, preferably phenyl, naphthyl, tetrahydronaphthyl or indanyl. It is advantageously a phenyl group.

For the purpose of the present invention, the term "heteroaryl group" is intended to mean any hydrocarbon-based aromatic group having from 3 to 9 atoms containing one or more heteroatoms, such as, for example, sulfur, nitrogen or oxygen atoms, and possibly bearing one or more substituents, such as, for example, a $C_1$-$C_7$ alkyl group as defined above, a $C_2$-$C_7$ alkenyl group as defined above or a halogen. Examples of heteroaryl groups are furyl, isoxazyl, pyridyl or pyrimidyl groups.

The term "polyalkoxyalkylene" is intended to mean a polyalkoxy($C_2$-$C_3$)alklylene (i.e. polyoxyethylenes and polyoxypropylenes), in particular polyethylene glycol, PEG, and $C_1$ to $C_3$ monoethers and monoesters thereof, having a molecular mass of preferably 1000 to 2000.

The expression "pharmacologically active molecule associated with a pathology" is intended to mean, in particular, any biovector capable of specifically recognizing a biological target whose expression is modified in a pathological zone compared with the nonpathological state, which includes all the biovectors mentioned in the application.

According to embodiments, (L-B) represents CH$_2$—CH$_2$—CONH-biovector or CH$_2$—CH$_2$—NHCO-biovector, the biovectors B being identical to or different than one another.

According to embodiments, the compounds according to the invention comprise at least one group capable of modifying the hydrophilicity or the biodistribution of the compounds, or of masking the chelate in such a way as not to impair the recognition of the biological target. In this case, these or these group(s) is (are) advantageously grafted in the place of a biovector B, for example of the compound:

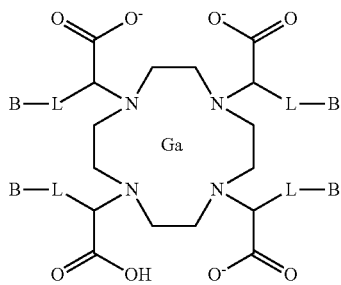

EXAMPLES

Part I: Examples of Macrocyclic Chelates and of Biovectors Coupled to Chelates

Example 1

DOTA-Scaffold Chelate

Stage 1: 5-(1,3-Dioxo-1,3-dihydroisoindol-2-yl)-2-(1,4,7,10-tetraazacyclododec-1-yl)pentanoic acid benzyl ester

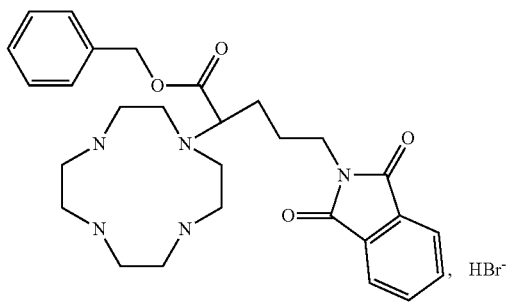 [SMILES: O=C(OCc1ccccc1)C(CCCN1C(=O)c2ccccc2C1=O)N1CCNCCNCCNCC1 ; [Br-]]

55 g of cyclen base (320 mmol) are dissolved in 550 ml of CH$_3$CN, to which 119.8 g of brominated derivative (2-bromo-5-(1,3-dioxo-1,3-dihydroisoindol-2-yl)pentanoic acid benzyl ester, 288 mmol) dissolved in 550 ml of CH$_3$CN are added dropwise. The medium is stirred at ambient temperature overnight. The precipitate is filtered off and washed thoroughly with acetonitrile. 138 g of product are obtained in the form of a white powder (corrected yield 81.3%).

TLC: CH$_2$Cl$_2$/MeOH/NH$_4$OH to 25% (80/40/3)
Visualization UV and CuSO$_4$
Rf: 0.3.

Stage 2: 5-(1,3-Dioxo-1,3-dihydroisoindol-2-yl)-2-(4,7,10-trisethoxycarbonylmethyl-1,4,7,10-tetraazacyclododec-1-yl)pentanoic acid benzyl ester

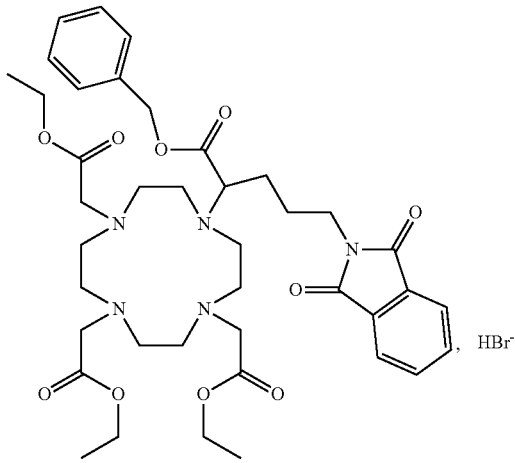 [SMILES: CCOC(=O)CN1CCN(CC(=O)OCC)CCN(C(CCCN2C(=O)c3ccccc3C2=O)C(=O)OCc2ccccc2)CCN(CC(=O)OCC)CC1 ; [Br-]]

60 g of the compound obtained in stage 1 (102 mmol) and 50.1 g of Na$_2$CO$_3$ (464 mmol) are added to a solution of 59.1 g of ethyl bromoacetate (Aldrich®, 358 mmol) in CH$_3$CN (1.11). The reaction medium is heated at 80° C. under an argon blanket overnight. After elimination of the precipitate, the filtrate is concentrated and washed thoroughly with CH$_3$CN. The product is crystallized from CH$_3$CN by adding Et$_2$O dropwise. 89.8 g of product are obtained in the form of a white solid (corrected yield 100%).

TLC: CH$_2$Cl$_2$/MeOH (9/1)
Visualization UV and KMnO$_4$
Rf: 0.4.

Stage 3: 5-Amino-2-(4,7,10-triscarboxymethyl-1,4,7,10-tetraazacyclododec-1yl)pentanoic acid

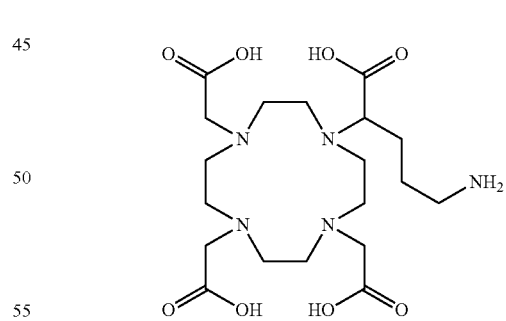

A solution of 54 g of compound obtained in stage 2 (64 ml) in 37% hydrochloric acid (1.81) is refluxed overnight in a 5-liter reactor. After cooling and filtration, the filtrate is concentrated and purified over silanized silica (elution with water). After evaporation under reduced pressure, the product is washed with ether. 45 g of product are obtained in the form of a white solid. The product is desalified by passing it over OH resin. 30 g of product are isolated in the form of white crystals (yield 100%).

HPLC: Hypercarb® 5μ, 200×4.6, 250 Å

Solvent A: 0.037 N sulfuric acid
Solvent B: CH₃CN
UV detection at 201 nm
Tr: 18 min.

Stage 4: Gallium complex of 5-amino-2-(4,7,10-triscarboxymethyl-1,4,7,10-tetraazacyclododec-1-yl)pentanoic acid

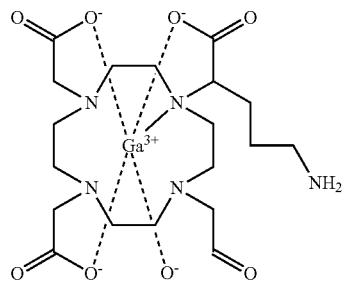

1 mg of the compound obtained in stage 3 (2.17 mmol) are dissolved in 7 µl of water and the pH is adjusted to 5.5 by adding 6 N hydrochloric acid. 0.920 mg of gallium nitrate nonohydrate (2.2 µmol) is added and the reaction medium is heated to 80° C. The pH of the solution should be maintained at around 5 by microadditions of 6 N hydrochloric acid. After two hours, the pH stabilizes. The slight cloudiness is filtered off through a Whatman® filter and the filtrate is concentrated. 1.2 mg of product are obtained in the form of white flakes (corrected yield 100%).

HPLC: Hypercarb® 5µ, 200×4.6, 250 Å
Solvent A: 0.037 N sulfuric acid
Solvent B: CH₃CN
UV detection at 201 nm
Tr: 10 min.

Stage 5: Gallium complex of 5-(2-ethoxy-3,4-dioxo-cyclobut-1-enylamino)-2-(4,7,10-triscarboxymethyl-1,4,7,10-tetraazacyclododec-1-yl)pentanoic acid

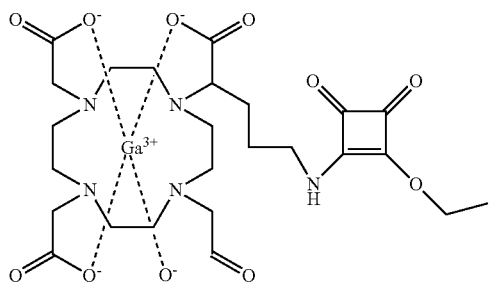

1 mg of compound obtained in stage 4 is dried by azeotropic distillation with toluene, and then suspended in 5 µl of anhydrous DMSO under an argon blanket. 0.5 µl of Et₃N dried over sieves and 0.8 mg of diethyl squarate (Aldrich®, 2.5 eq.) are then added. The medium is stirred at ambient temperature under an argon blanket for 1 hour. The mixture is precipitated from ether. The solid obtained is filtered off and then washed with dichloromethane. After filtration and drying, 0.98 mg of a white solid (yield of 81%) is recovered.

HPLC: Symmetry C18, 5µ, 250×4.6, 100 Å
A: water TFA, pH=2.7
B: CH₃CN
Detection at 201 and 254 nm
Tr: 19.8 min.

Example 2

Peptide Couplings

| Sequence | MW | m in mg | SEQ ID NO |
|---|---|---|---|
| Asp(tBu)-Ala-His(trt)-Ser(tBu)-Phe-Ser(tBu)OH | 1073.31 | 172 | 7 |
| Leu-Ile-Lys(Boc)-Lys(Boc)-Pro-Phe-OH | 945.22 | 151 | 8 |
| Pro-Gly-Asp-(tBu)-Leu-Ser(tBu)-Arg(Pbf)-OH | 1008.25 | 161 | 9 |
| Gly-Asp(tBu)-Ala-His(trt)-Ser(tBu)-Phe-Ser(tBu)OH | 1130.36 | 180 | 10 |
| γ-Abu-Asp(tBu)-Ala-His(trt)-Ser(tBu)-Phe-Ser(tBu)OH | 1158.42 | 185 | 7 |
| 8-Amino-3,6-dioxaoctanoyl-Asp(tBu)-Ala-His(trt)-Ser(tBu)-Phe-Ser(tBu)OH | 1218.47 | 195 | 7 |

Stage 1: Coupling of Peptides No. 1, 2, 3, 4, 5 or 6 to the Squarate Derivative

The compound obtained in stage 5 of example 14 (100 µg, 1.53×10⁻⁷ mol) is dissolved in 15 µl of aqueous solution of Na₂CO₃, pH 9.4. The protected peptide (1.6×10⁻⁷ mol) is introduced while maintaining the pH at 9.4 by adding Na₂CO₃. If the peptide is not soluble in water, a few microdrops of DMF are added until complete dissolution is obtained. After reaction at ambient temperature for 48 h, the medium is precipitated from an ethanol/ethyl ether mixture. The precipitate is filtered off and then dried.

Stage 2: Deprotection

The compound obtained in stage 1 is dissolved in a mixture of 10 µl of TFA/TIS/H₂O in the proportions 90/5/5. The medium is stirred at ambient temperature for 5 h and the solvent is then evaporated off under reduced pressure. The residue is taken up in ethyl ether and the precipitated is filtered off and then dried. The product is then purified by preparative HPLC on a Symmetry® column with an eluant consisting of water/TFA pH 3/CH₃CN.

| No. | Structure | MW |
|---|---|---|
| 1 | 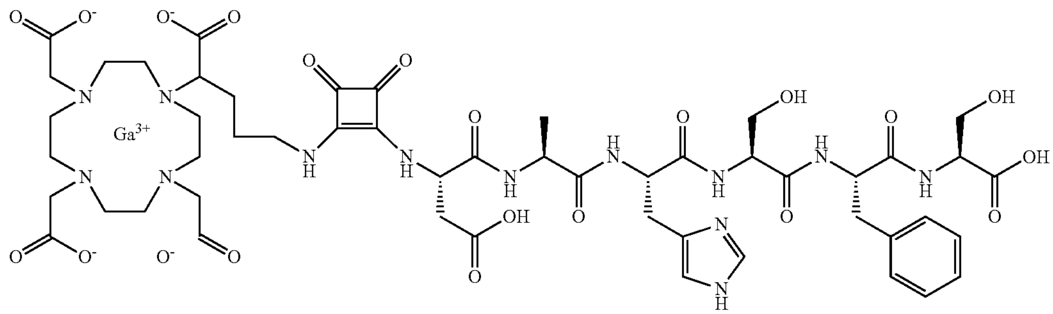 | 1267.9 |
| 2 | 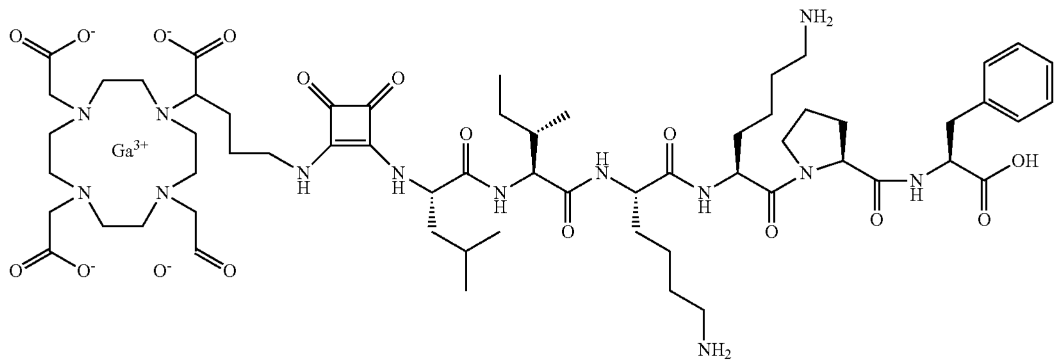 | 1350.22 |
| 3 | 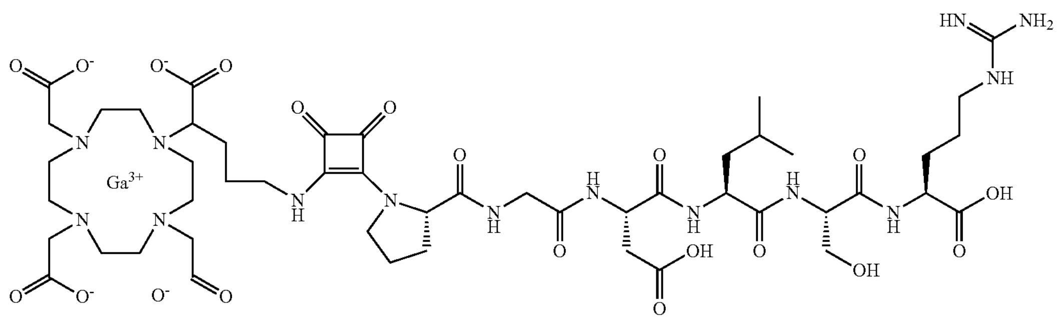 | 1248.94 |
| 4 | 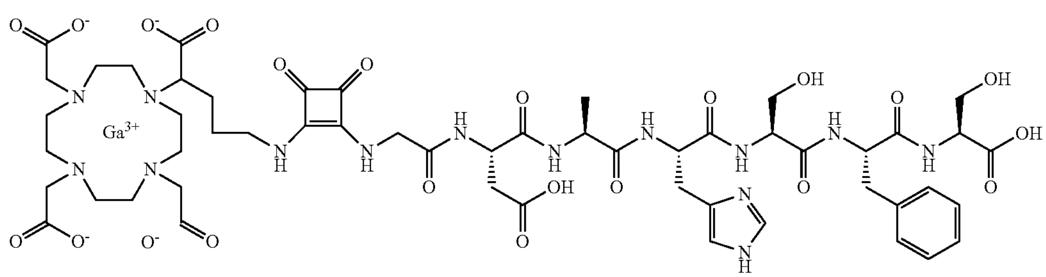 | 1324.95 |
| 5 | 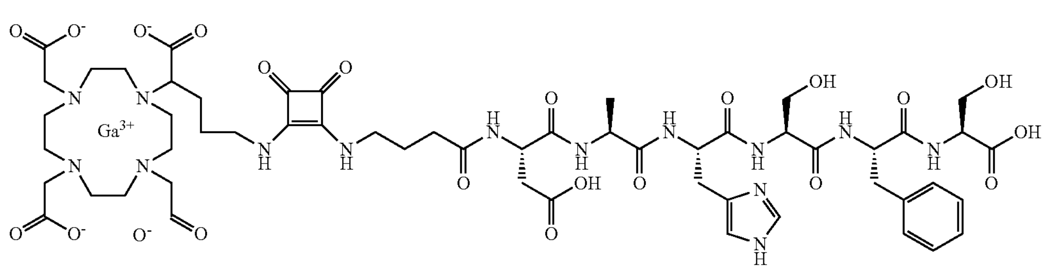 | 1353.00 |

| No. | Structure | MW |
|---|---|---|
| 6 | 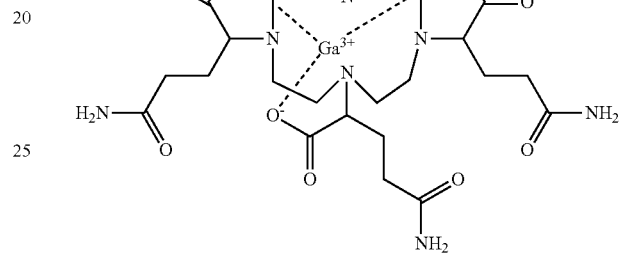 | 1413.06 |

Example 3a

PCTA Scaffold

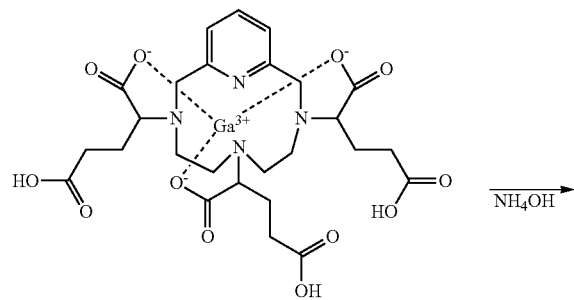

Example 3b

DO3A Scaffold

A solution containing 0.10 mmol of ammonia in 20 μl of water is prepared. The pH is adjusted to 6 with HCl. 1.8 mg of gallium complex of 3,6,9,15-tetraazabicyclo[9,3,1]pentadeca-1(15),11,13-triene-3,6,9-tri(α-glutaric) acid, 0.2 mg of HOBT, 2.5 mg of EDCI and 15 μl of dioxane are added to the above solution. The pH is adjusted to 6. After 24 h, the reaction medium is concentrated to approximately 7 ml. The reaction medium is precipitated from 70 μl of ethanol+20 μl of ether. The solid is filtered off and then purified by chromatography on silanized silica RP2, elution being carried out with water. 1.2 mg of product are obtained.

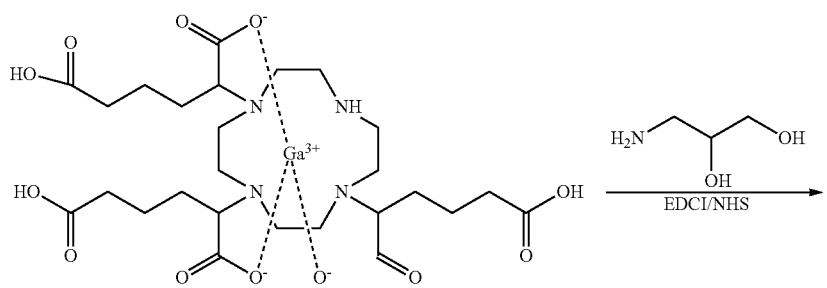

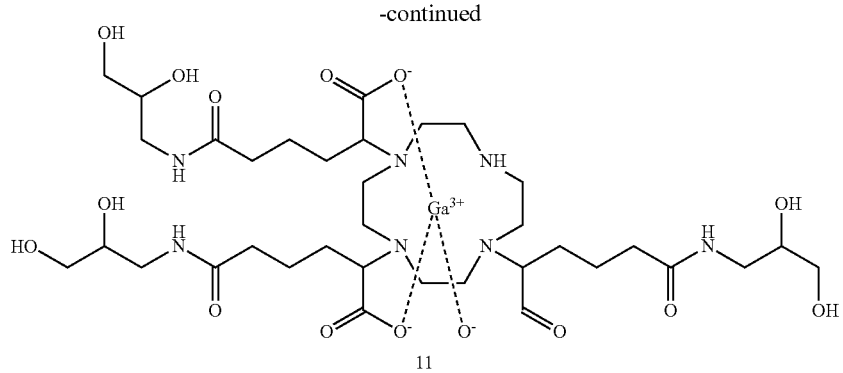

11

A solution containing 0.26 mg of 3-aminopropane-1,2-diol in 6 μl of water is prepared. The pH is adjusted to 6 with HCl. 0.5 mg of gallium complex of 2-[4,7-bis(1,4-dicarboxybutyl]-1,4,7,10-tetraazacyclododec-1-yl]hexanoic acid are added to the above solution. The pH is again adjusted before adding 0.071 mg of sulfo-NHS and 0.062 mg of EDCI. The pH is checked and adjusted to 6 with 2N NaOH. After an overnight period at AT, the reaction medium is concentrated to approximately 2 ml and then precipitated from 10 ml of ethanol. The solid is filtered off, washed with ethanol and diethyl ether, and then purified on silanized silica RP2, elution being carried out with water only. 0.2 mg of product is obtained.

The amino alcohol chains of this example 3b are an example of hydrophilic groups that can improve the hydrophilicity, and, where appropriate, the masking of the chelate described in the application.

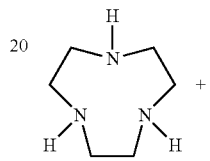

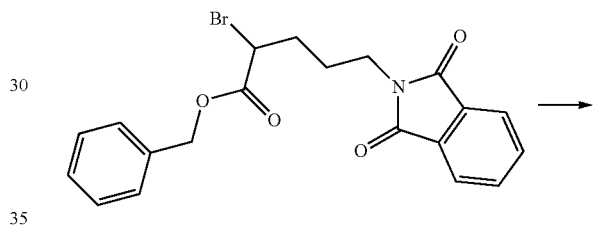

Example 4

NOTA Scaffold

Gallium complex of 2-(4,7-biscarboxymethyl[1,4,7]triazonan-1-yl)-5-(2-ethoxy-3,4-dioxocyclobut-1-enylamino)pentanoic acid

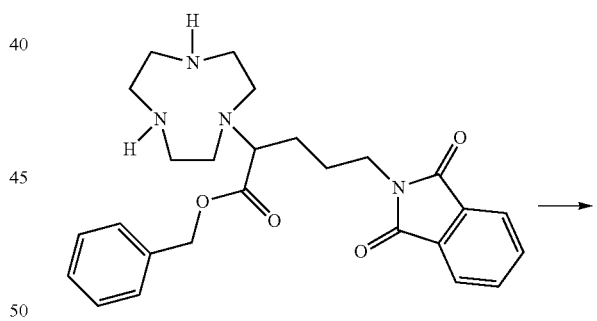

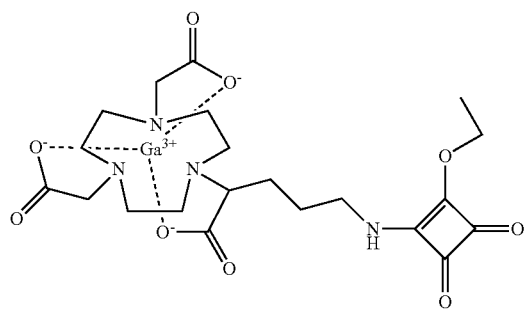

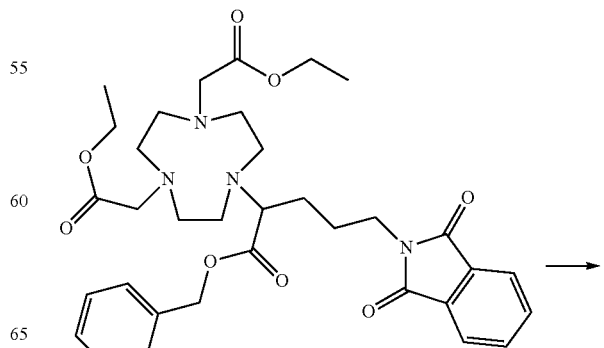

This compound is prepared according to the following synthesis scheme, starting from commercial triaza-1,4,7-cyclononane according to the protocols described in example 1.

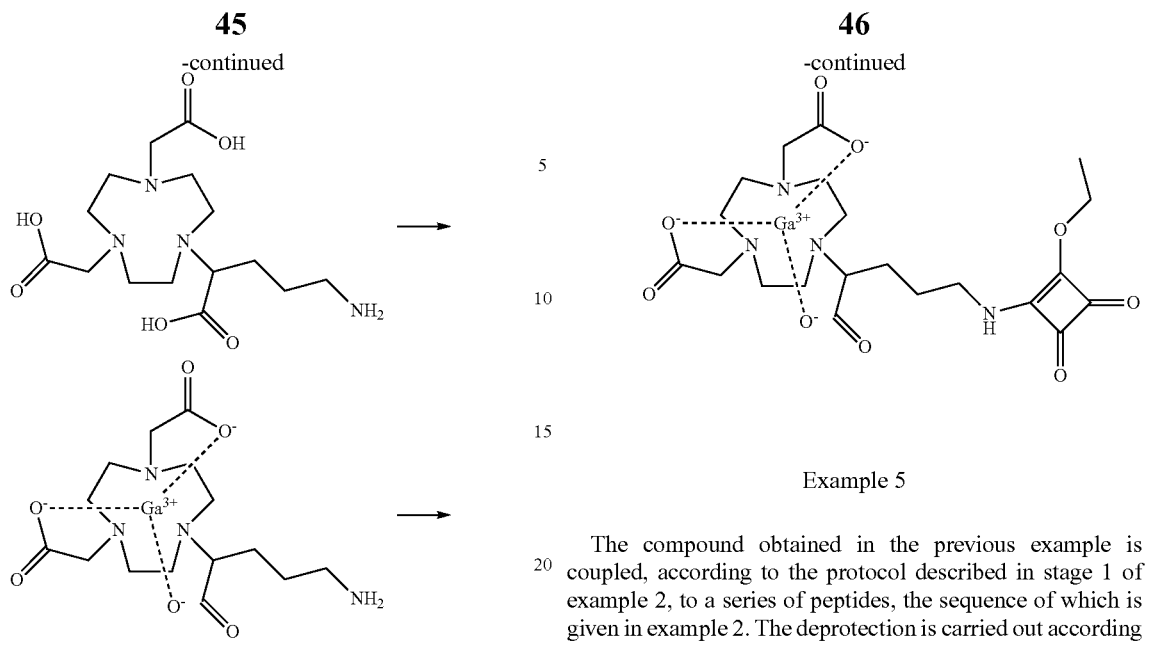
Example 5
The compound obtained in the previous example is coupled, according to the protocol described in stage 1 of example 2, to a series of peptides, the sequence of which is given in example 2. The deprotection is carried out according to the method described in stage 2 of example 2.
| No. | Structure | MW |
|-----|-----------|-----|
| 1 | 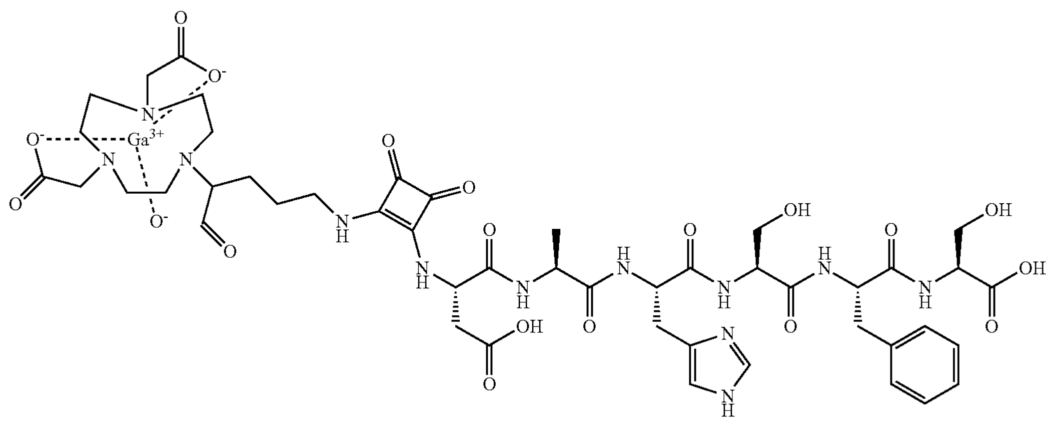 | 1167.80 |
| 2 | 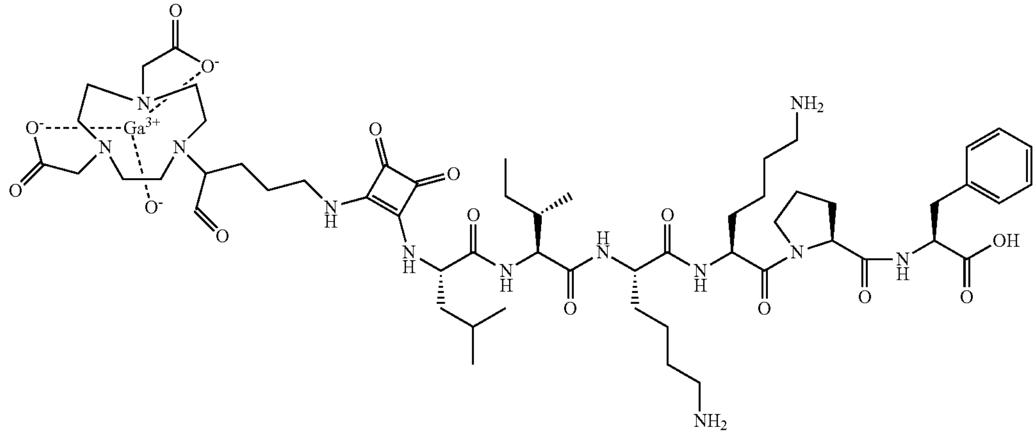 | 1250.12 |

| No. | Structure | MW |
|---|---|---|
| 3 | 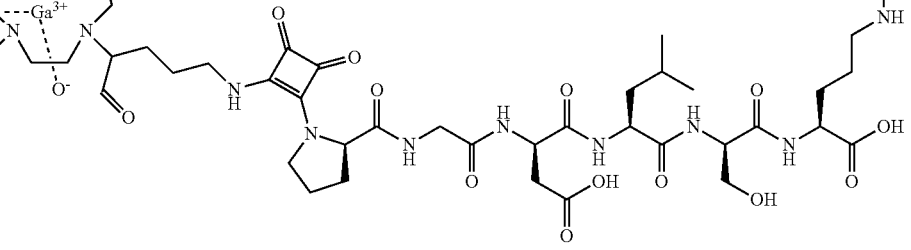 | 1148.84 |
| 4 | 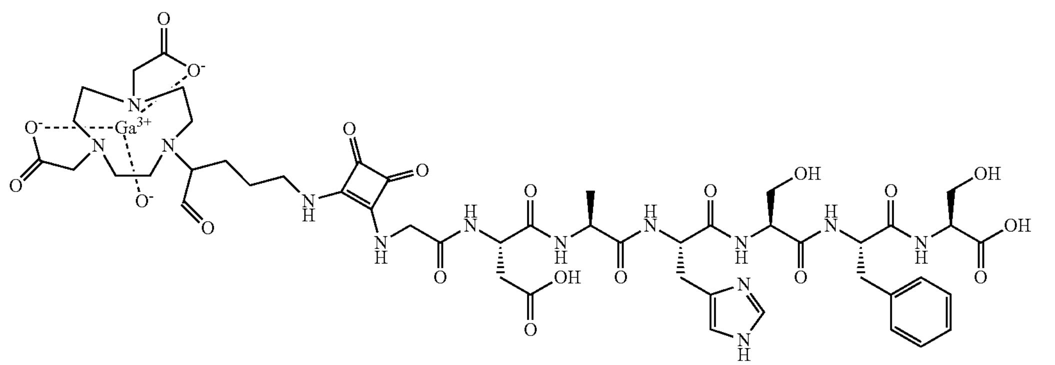 | 1224.85 |
| 5 | 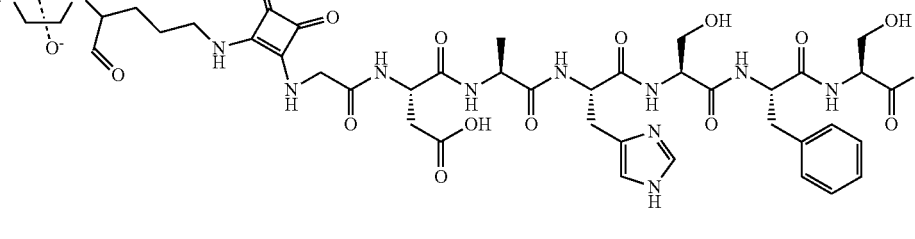 | 1252.91 |
| 6 | 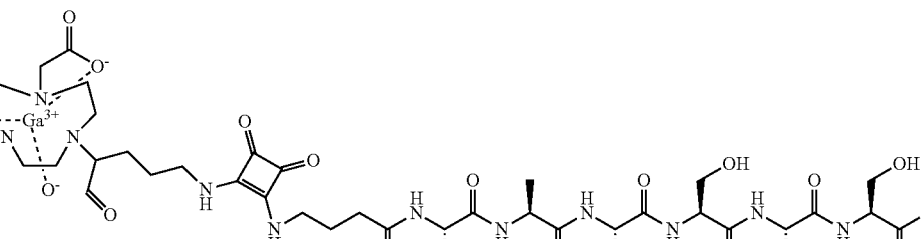 | 1312.96 |

Example 6

Stage 1: 2-(3,6,9,15-Tetraazabicyclo[9.3.1]penta-deca-1(15),11,13-trien-3-yl)pentanedioic acid diethyl ester

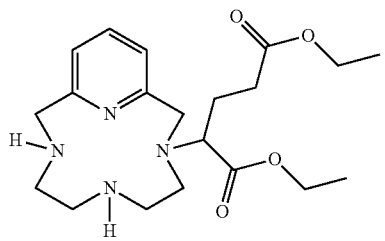 [SMILES: CCOC(=O)CCC(C(=O)OCC)N1CCNCCNCc2cccc(n2)C1]

10 mg of 3,6,9,15-tetraazabicyclo[9.3.1]pentadeca-1(14),11(15),12-triene (48.5 µmol) are dissolved in a water-acetonitrile mixture (170 µl of acetonitrile and 7 µl of water). After the addition of 10 µl of TEA (1.4 eq), the mixture is heated to 50° C. and then 13 mg of ethyl bromoglutarate (1 eq) are added. The medium is stirred at 50° C. for 18 h.

The acetonitrile is evaporated off and the residue taken up with dichloromethane is washed with water (100 µml). The organic phase is dried over anhydrous magnesium sulfate and evaporated to dryness. Brown oil. Yield 58%.

MS: 393.20 in ES+.

Stage 2: 2-(6,9-Bisethoxycarbonylmethyl-3,6,9,15-tetraazabicyclo[9.3.1]pentadeca-1(15),11,13-trien-3-yl)pentanedioic acid diethyl ester

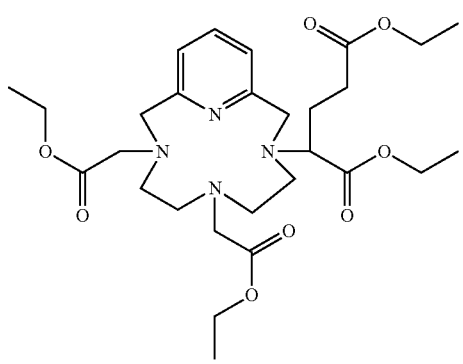 [SMILES: CCOC(=O)CCC(C(=O)OCC)N1CCN(CC(=O)OCC)CCN(CC(=O)OCC)Cc2cccc(n2)C1]

9.5 mg of the compound obtained in stage 1 (24 µmol) are solubilized in 200 µl of acetonitrile with 8.2 mg of $Na_2CO_3$ (4.5 eq). The mixture is brought to reflux and ethyl bromoacetate (9.8 mg, 3.4 eq) is added rapidly. The reaction medium is brought to reflux for 18 h. The salts are filtered off and the solvent is evaporated off. Brown oil. Quantitative yield. MS: 565 in ES+.

Stage 3: 2-(6,9-Biscarboxymethyl-3,6,9,15-tetraazabicyclo[9.3.1]pentadeca-1(15),11,13-trien-3-yl)pentanedioic acid

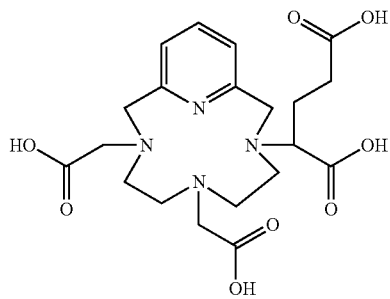 [SMILES: O=C(O)CCC(C(=O)O)N1CCN(CC(=O)O)CCN(CC(=O)O)Cc2cccc(n2)C1]

15 mg of the compound obtained in stage 2 (26.5 µmol) are dissolved in 40 µl of ethanol and 53 µl of 5N sodium hydroxide are added dropwise rapidly. The mixture is brought to reflux for 24 h. The reaction medium is diluted 10-fold with water and the pH is then adjusted to 6.5 by adding weakly acidic resin. The resin is filtered off and washed with water. A strongly basic resin is added to the filtrate and then filtered off and washed twice with water. The product is eluted with 50% acetic acid. After evaporation to dryness, the product is obtained in the form of brown crystals. m=8 mg. Yield=60%.

MS: 453.2 in ES+.

Stage 4: Gallium complex of 2-(6,9-biscarboxymethyl-3,6,9,15-tetraazabicyclo[9.3.1]pentadeca-1(15),11,13-trien-3-yl)pentanedioic acid

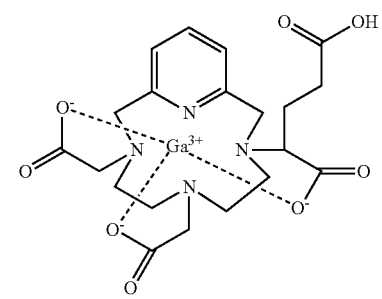

According to the protocol of stage 4 of example 1. White powder. Quantitative yield.

MS: 518 in ES−.

Example 7

The compound obtained in the previous example is coupled, according to the protocol described in example 2, to a series of peptides, the sequence of which is given in example 2. The deprotection is carried out according to the method described in stage 2 of example 2.

| No. | Structure | MW |
|---|---|---|
| 1 | 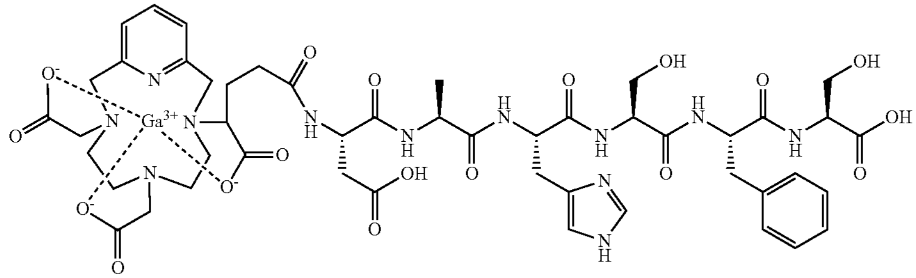 | 1163.81 |
| 2 | 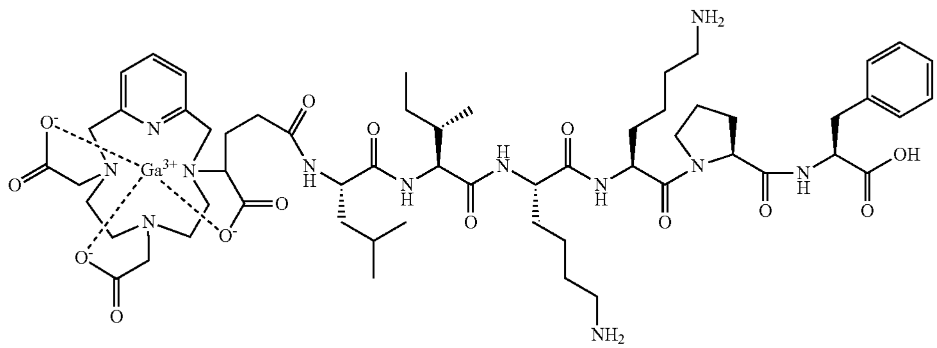 | 1246.13 |
| 3 | 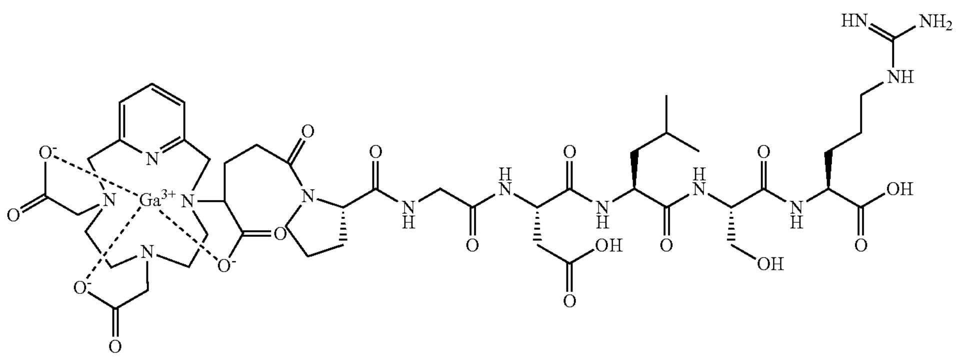 | 1144.85 |
| 4 | 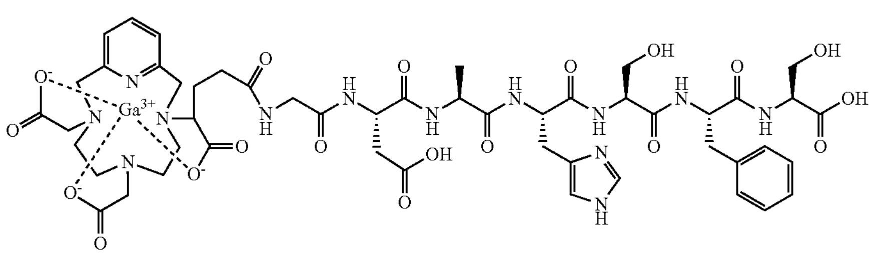 | 1220.86 |
| 5 | 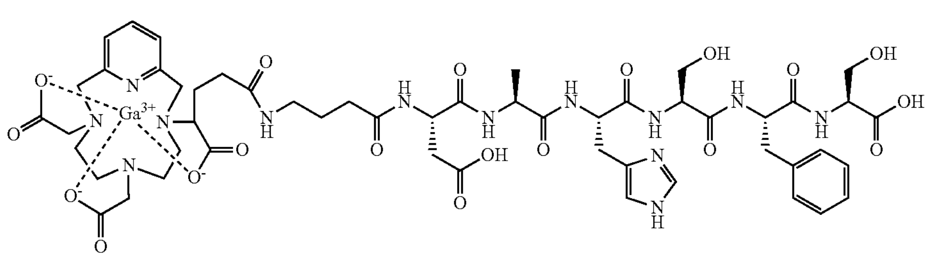 | 1248.92 |

| No. | Structure | MW |
|---|---|---|
| 6 | 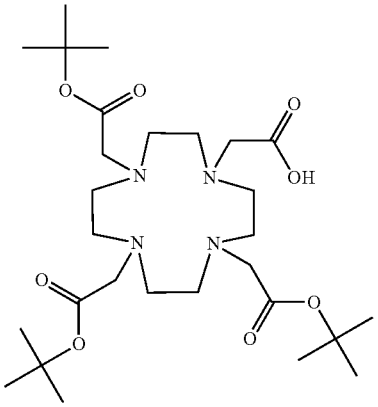 | 1308.97 |

Example 8
(4,7,10-Tris-tert-butoxycarbonylmethyl-1,4,7,10-tetraazacyclododec-1-yl)-acetic acid Stage 1:

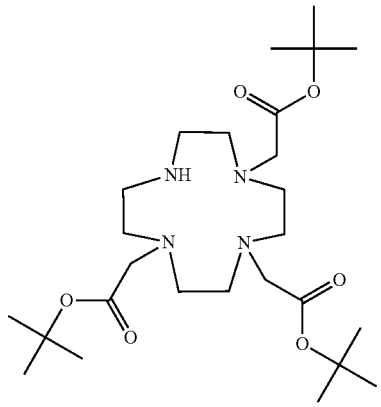

Mw = 514.71 g/mol 73 g of cyclen base (0.42 mol) and 108 g of sodium acetate (i.e. 1.3 mol) are stirred in 1.2 l of dimethylacetamide (DMAC), under argon, at ambient temperature for half an hour. 256 g of tert-butyl bromoacetate (1.3 mol) dissolved in 300 ml of DMAC are then added dropwise. The reaction medium is stirred at ambient temperature for 3 weeks. The reaction medium is cooled to 5° C. and then filtered. The crystals obtained are washed with 150 ml of ice-cold DMAC and then with 210 ml of ethyl acetate. A white solid is obtained with a yield of 60%.

TLC: $CH_2Cl_2$/MeOH/$NH_4OH$ at 25% (80/15/5)
Visualizing agent: $KMnO_4$; Rf=0.75
HPLC: SYMMETRY C18, 5 μm, 250×4.6 mm, 100 Å
Solvent A: Water/TFA, pH 2.7; Solvent B: $CH_3CN$
UV detection at 201 nm; Tr=35.5 min Stage 2:

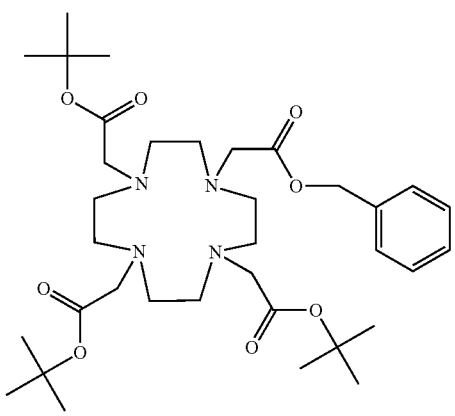

Mw = 662.87 g/mol 1 g of the compound obtained in stage 1 and 0.38 g of $K_2CO_3$ are dissolved in 15 ml of $CH_3CN$. 0.37 ml of benzyl bromoacetate is added dropwise. The reaction medium is refluxed overnight under argon. After returning to ambient temperature, the reaction medium is filtered and then concentrated. After acid-base washes, 1 g of crystals is obtained.

HPLC: SYMMETRY C18, 3.5 μm, 50×2.1 mm,
Solvent A: 0.05% formic acid; Solvent B: $CH_3CN$ (+0.04% formic acid)
UV detection at 220 nm; Tr=3.8 min.

Stage 3:

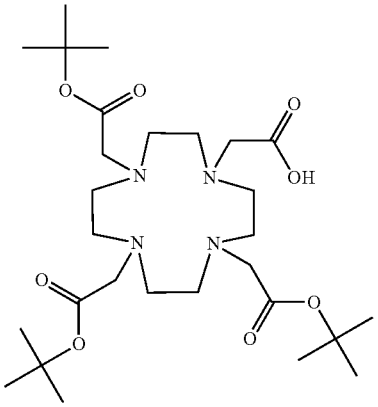

Mw = 572.75 g/mol 1 g of the compound obtained in stage 2 is dissolved in 20 ml of EtOH and hydrogenated at very low pressure (balloon, in the presence of palladium-on-charcoal, at 25° C. for 15 h). After filtration and evaporation of the solvent, 0.6 g of white crystals is obtained (yield of 73%).

HPLC: SYMMETRY C18, 3.5 μm, 50×2.1 mm
Solvent A: 0.05% formic acid; Solvent B: $CH_3CN$ (+0.04% formic acid)
UV detection at 220 nm; Tr=3.1 min.

Example 9

The compound obtained in example 8 is coupled to a series of peptides, the sequences of which are given in example 2, according to the following protocol.

Stage 1: Coupling of Peptides No. 1, 2, 3, 4, 5 or 6 to the Compound of Example 8

0.4 g of the compound obtained in example 8 (0.7 mmol), 144 mg of DCC (0.7 mmol) and 80 mg of NHS (0.7 mmol) are stirred in 10 ml of $CH_2Cl_2$ for 20 min at AT. 20 ml of a solution of protected peptide (0.7 mmol) and of triethylamine (1.4 mmol) in DMSO are added to the preactivated ester. After 30 minutes, the reaction medium is precipitated from 450 ml of ethyl ether. The precipitate is filtered off and then dried.

Stage 2:

The deprotection is carried out according to the method described in stage 2 of example 2

Stage 3: Complexation

The compound obtained in stage 2 (0.041 mmol) is dissolved in 1 ml of 0.1 M acetate buffer at pH 4.8. 0.041 mmol of gallium acetate is added and the pH is adjusted to 5.5. The solution is then heated at 80° C. for 10 min. The reaction medium is concentrated. Heating for 10 minutes is, however, already satisfactory for obtaining gallium complexation.

| No. | Structure | MW |
|---|---|---|
| 1 | 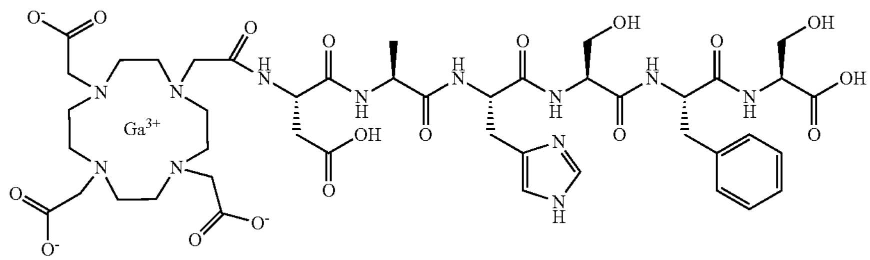 | 1115.77 |
| 2 | 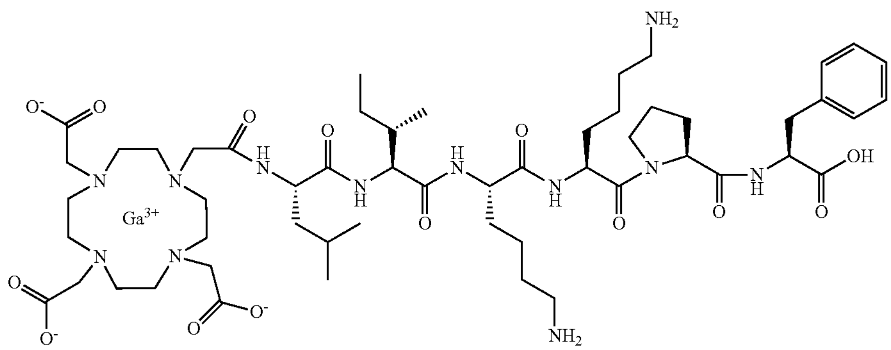 | 1198.09 |
| 3 | 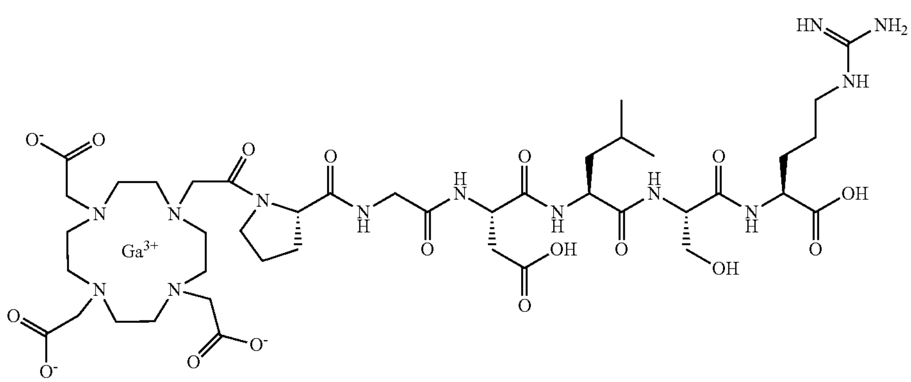 | 1096.81 |
| 4 | 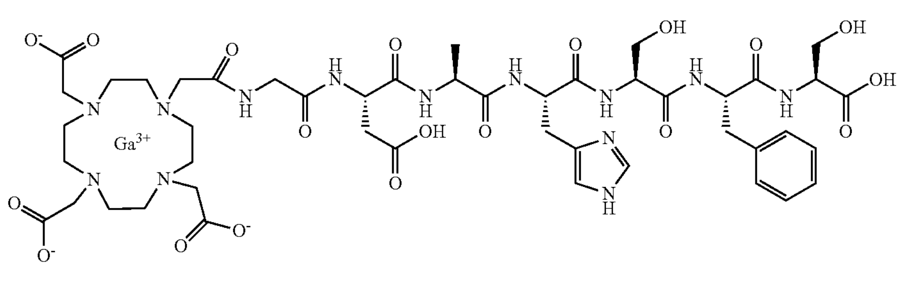 | 1172.82 |

| No. | Structure | MW |
|---|---|---|
| 5 | 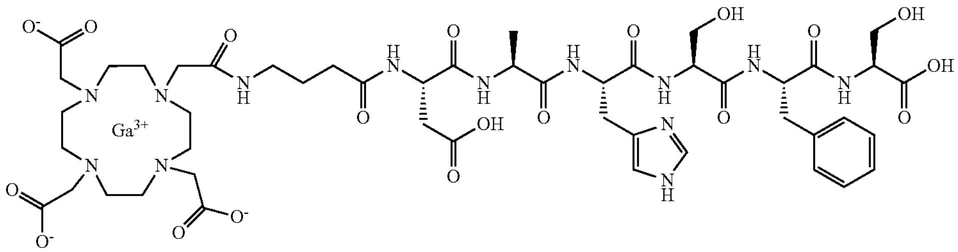 | 1200.87 |
| 6 | 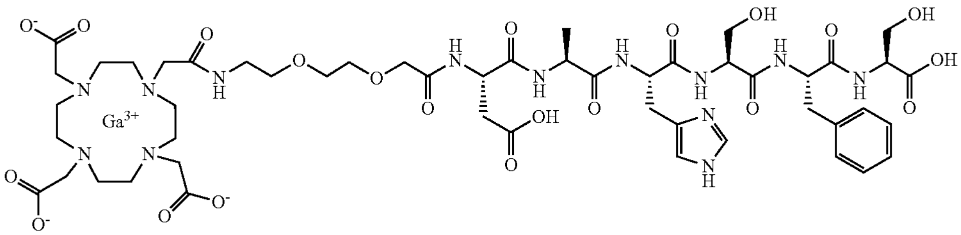 | 1260.93 |

Example 10

The compound obtained in example 8 is coupled to a series of folic acid derivatives (No. 7, 8 or 9), the structures of which are given in the table below.

| No. | Structure | MW |
|---|---|---|
| 7 | 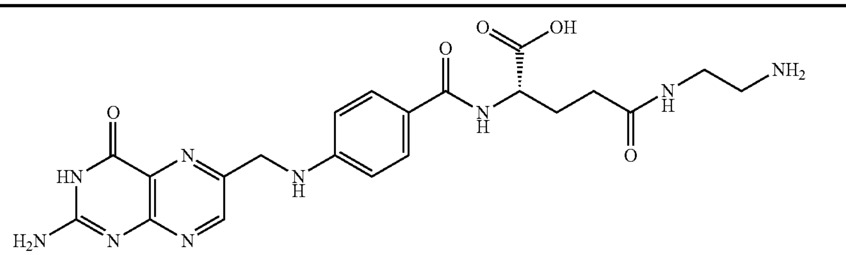 | 483.49 |
| 8 | 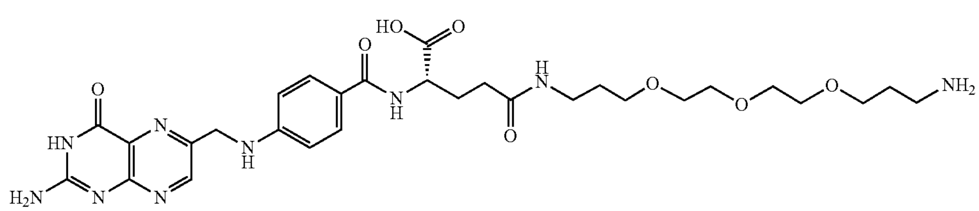 [SMILES: NCCCOCCOCCOCCCNC(=O)CC[C@H](NC(=O)c1ccc(NCc2cnc3nc(N)[nH]c(=O)c3n2)cc1)C(=O)O] | 643.71 |
| 9 | 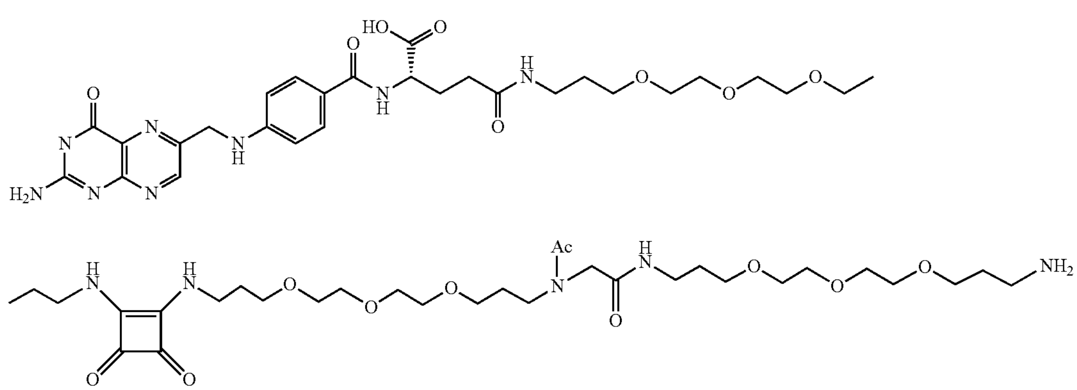 | 1244.42 |

Synthesis of the Folic Acid Derivatives:

The synthesis of derivative No. 8 is described in example 11 of document WO 2004/112839, pages 105 to 108.

The synthesis of derivative No. 7 is carried out according to the same protocol as for derivative 8, with the exception of the final stage, where the 4,7,10-trioxa-1,13-tridecanediamine is replaced with ethylenediamine.

The synthesis of derivative No. 9 is carried out using the derivative 8 which is condensed to the linker whose structure is the following

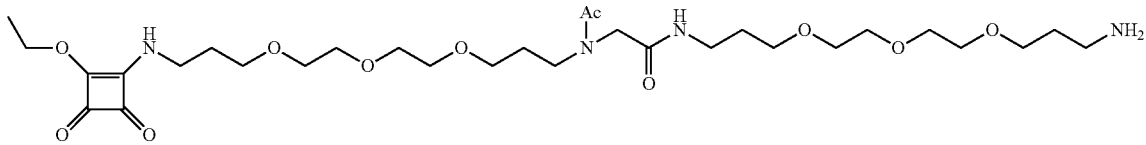 [SMILES: CCOc1c(NCCCOCCOCCOCCCN(CC(=O)NCCCOCCOCCOCCCN)C(C)=O)c(=O)c1=O]

Briefly, the synthesis of this linker is carried out in 4 stages using the 4,7,10-trioxa-1,13-tridecanediamine monoBoc (compound a) of example 15 in the specific patent).

Stage 1:

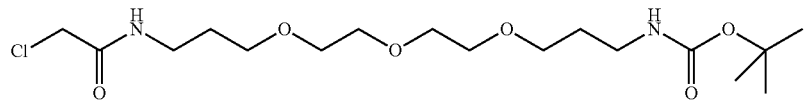 [SMILES: CC(C)(C)OC(=O)NCCCOCCOCCOCCCNC(=O)CCl]

10 g of 4,7,10-trioxa-1,13-tridecanediamine monoBoc (31.2 mmol) are dissolved at −5° C. (by means of a bath of acetone and ice) in 50 ml of $CH_2Cl_2$. 5 g of $K_2CO_3$ (36.2 mmol) dissolved in 50 ml of water and 5 g of chloroacetyl chloride (44.2 mmol) dissolved in 50 ml of $CH_2Cl_2$ are added simultaneously, dropwise, under cold conditions. The reaction medium is stirred at AT for 1 hour. The organic phase is washed with water until neutral pH and then filtered and evaporated to dryness.

m=11.2 g.

ES$^+$: m/z (z=1)=397.3.

Stage 2:

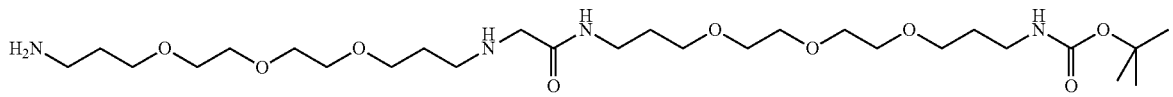 [SMILES: CC(C)(C)OC(=O)NCCCOCCOCCOCCCNC(=O)CNCCCOCCOCCOCCCN]

6.8 g of 4,7,10-trioxa-1,13-tridecanediamine are dissolved in 50 ml of $CH_3CN$ in the presence of 0.85 g of $K_2CO_3$. 6.2 mmol of the compound derived from stage 1, dissolved in 25 ml of $CH_3CN$, are added, dropwise, to this solution. The reaction medium is refluxed for 2 h. After returning to ambient temperature, the reaction medium is filtered and then evaporated. The residue obtained is dissolved in 50 ml of $CH_2Cl_2$ and washed with 4×20 ml of water. The organic phase is dried over $Na_2SO_4$ and then purified on silica with a 50/50 then 30/70 mixture of $CH_2Cl_2$/MeOH. m=1.8 g (yield 50%).

ES$^+$ M/z=581 (z=1) and M/z=291.3 (z=2).

Stage 3:

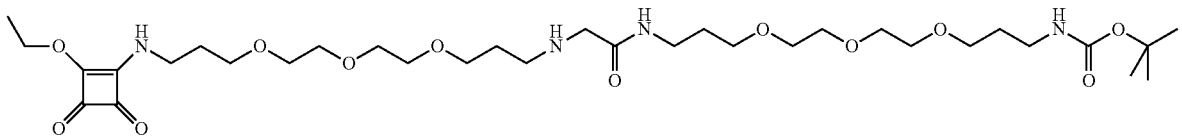 [SMILES: CCOc1c(NCCCOCCOCCOCCCNCC(=O)NCCCOCCOCCOCCCNC(=O)OC(C)(C)C)c(=O)c1=O]

0.25 g of the compound derived from the preceding stage is solubilized in 1.5 ml of $CH_2Cl_2$. 57.5 μl of diethyl squaric acid are added. The reaction medium is stirred for 18 h at ambient temperature. The product is not isolated.

$ES^+$ M/z=706 (z=1) and M/z=354 (z=2).

Stage 4:

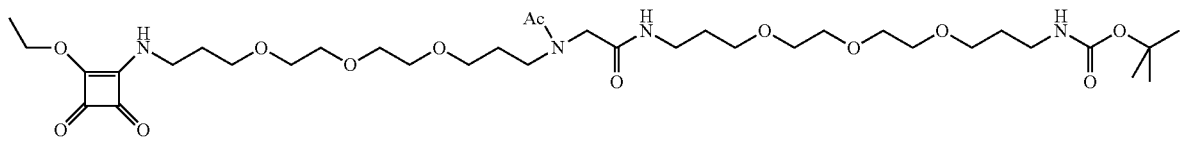 [SMILES: CCOc1c(NCCCOCCOCCOCCCN(CC(=O)NCCCOCCOCCOCCCNC(=O)OC(C)(C)C)C(C)=O)c(=O)c1=O]

40.6 μl of $Ac_2O$ are added to the reaction medium derived from stage 3, and the whole is stirred for 5 minutes at ambient temperature before being purified on silica, elution being carried out with $CH_2Cl_2$/EtOH (9/1). m=0.27 g (translucent oil).

$ES^+$ M/z=748 with z=1.

Stages 1 and 2 corresponding to the coupling of folic acid derivatives No. 7, 8 or 9 to the acid derivative of example 8, and to the deprotection, are carried out according to the same protocol as that described in example 9.

Stage 5: Complexation 0.041 mmol of the compound obtained in stage 2 is dissolved in 1.1 ml of water. 0.041 mmol of anhydrous gallium chloride is added, and the reaction medium is heated at 80° C. for 10 min. The reaction medium is concentrated.

| No. | Structure | MW |
|---|---|---|
| 7 | 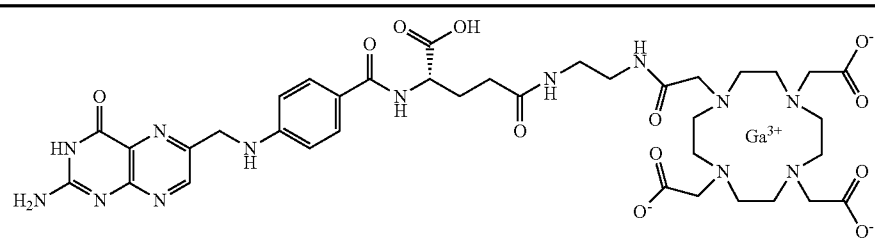 | 937.60 |
| 8 | 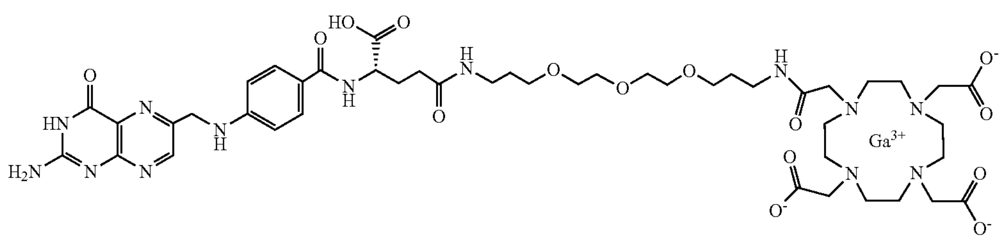 | 1096.81 |
| 9 | 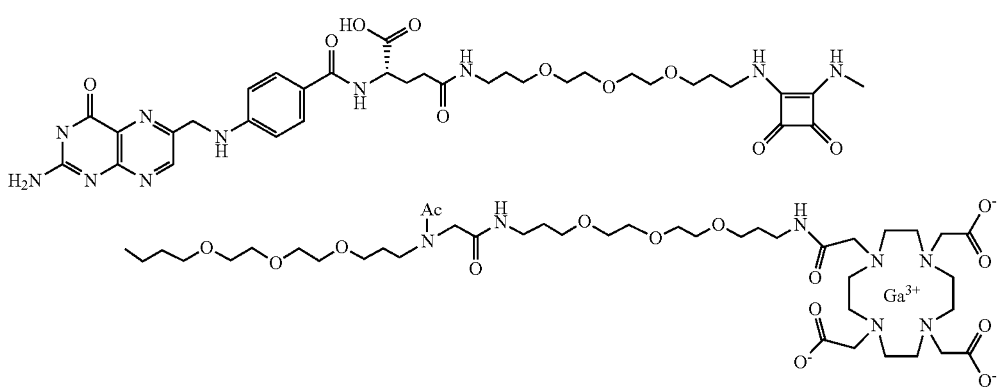 | 1698.53 |

The coupling of a linker-biovector assembly to a single carboxylic function has been described in detail. Similarly, using appropriate protections/deprotections, several linker-biovector assemblies are coupled to the chelate, advantageously 3 or 4 assemblies (one assembly per carboxylic function).

Example 11

4-(4-Isothiocyanatophenyl)-2-(4,7,10-tris-tert-butoxycarbonylmethyl-1,4,7,10-tetraazacyclododec-1-yl)butyric acid tert-butyl ester Stage 1:
Identical to that of example 8
Stage 2:

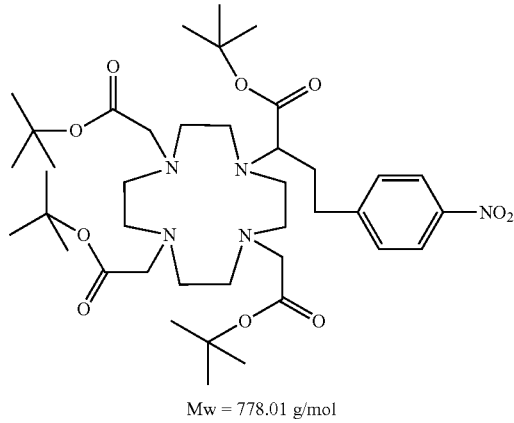

Mw = 778.01 g/mol 26.8 g of 2-bromo-4-(4-nitrophenyl)butyric acid tert-butyl ester in solution in 50 ml of $CH_3CN$ are added, dropwise, to a suspension of 20 g of the compound obtained in stage 1 and 10.8 g of $K_2CO_3$ in 400 ml of $CH_3CN$. After stirring at 25° C. for 24 h, the reaction medium is filtered, washed with $CH_3CN$ and then concentrated. After acid-base washes, 18 g of product are obtained.

Mass spectrum: Mode $ES^+$ m/z=779 with z=1.

Stage 3: Reduction of the Nitro

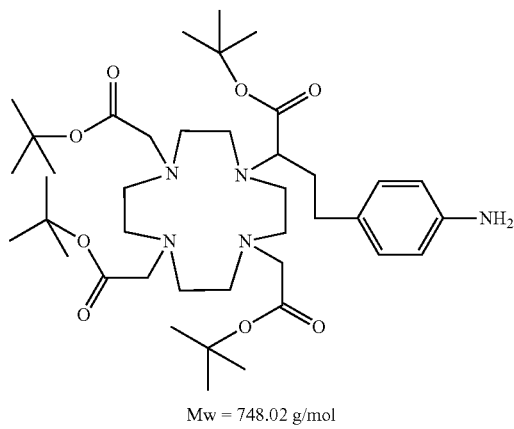 [SMILES: CC(C)(C)OC(=O)CN1CCN(CC(=O)OC(C)(C)C)CCN(C(CCc2ccc([N+](=O)[O-])cc2)C(=O)OC(C)(C)C)CCN(CC(=O)OC(C)(C)C)CC1]

Mw = 748.02 g/mol 5 g of the compound obtained in stage 2 are dissolved in 70 ml of MeOH and hydrogenated under pressure (10% palladium-on-charcoal, 25° C. under a hydrogen pressure of $3 \times 10^5$ Pa for 6 h). 4.2 g of product are obtained.

Mass spectrum: Mode $ES^+$ m/z=749 with z=1.

Stage 4:

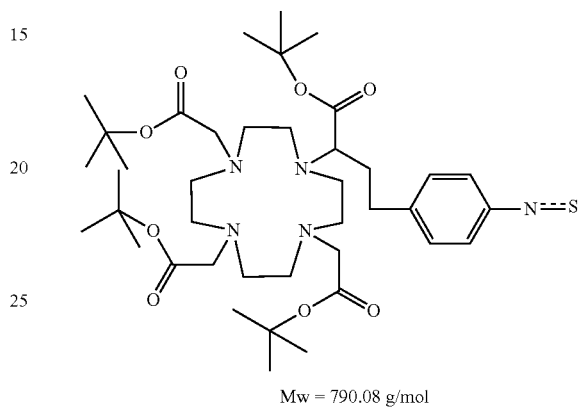

Mw = 790.08 g/mol 2 g (2.7 mmol) of the product derived from stage 3 are solubilized in a mixture of 24 ml of water and 16 ml of $CHCl_3$. 0.45 ml (5.8 mmol) of $SCCl_2$ are added dropwise and the whole is stirred for 1 h 30. the reaction medium is separated by settling out and the organic phase is evaporated under vacuum. The concentrate is taken up in ether and stirred at AT overnight. The precipitate is filtered off and dried under vacuum. m=2 g.

Mass spectrum: Mode $ES^+$ m/z=791 with z=1.

Example 12

The compound obtained in example 11 is coupled to a series of peptides, the sequences of which are given in example 2, according to the following protocol.

Stage 1: Addition of Peptides No. 1, 2, 3, 4, 5 or 6 to the Derivative of Example 11

1.2 g (1.5 mmol) of the compound obtained in example 11 are solubilized in 30 ml of DMSO. The protected peptide (1.5 mmol) and 3 mmol of triethylamine are stirred for 24 h. The reaction medium is then precipitated from 500 ml of diethyl ether.

Stages 2 and 3:
The deprotection and the complexation are carried out as in example 9 (stages 2 and 3)

| No. | Structure | MW |
|---|---|---|
| 1 | 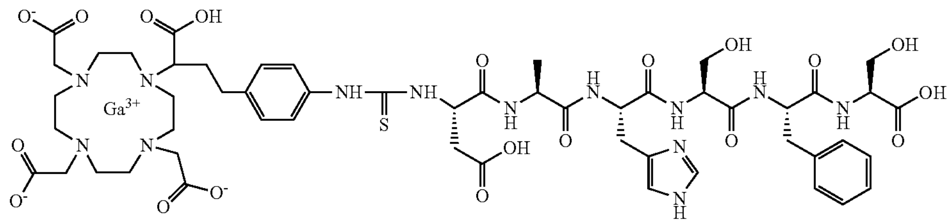 | 1295.01 |
| 2 | 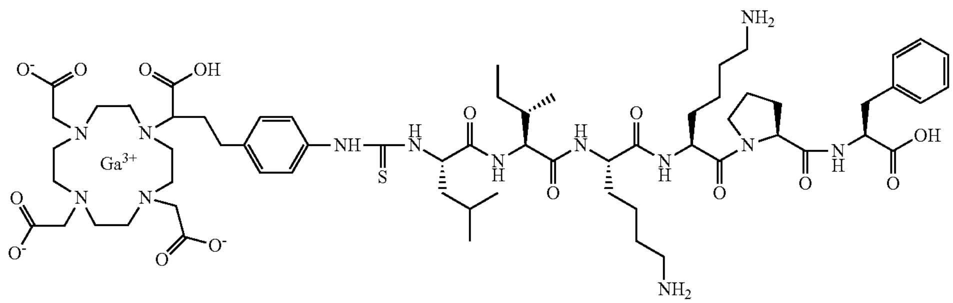 | 1377.33 |
| 3 | 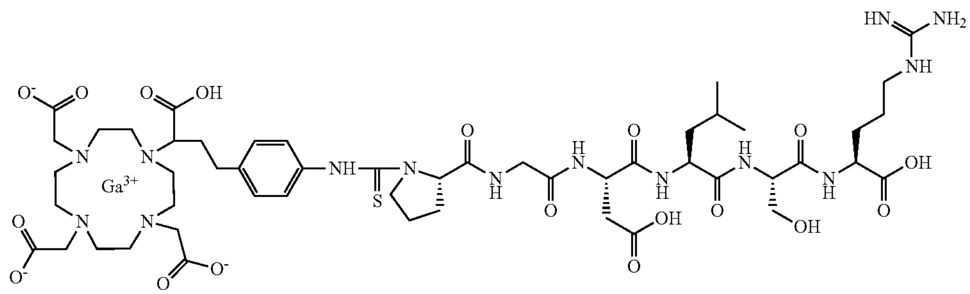 | 1276.05 |
| 4 | 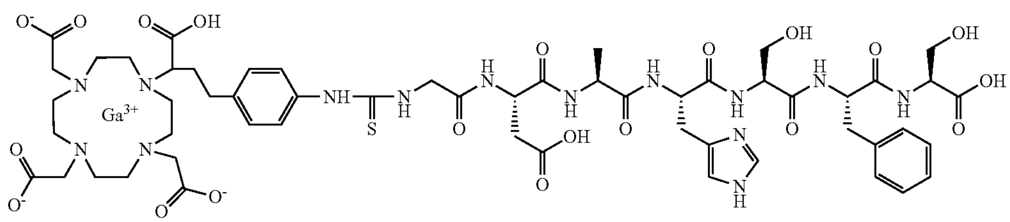 | 1352.06 |
| 5 | 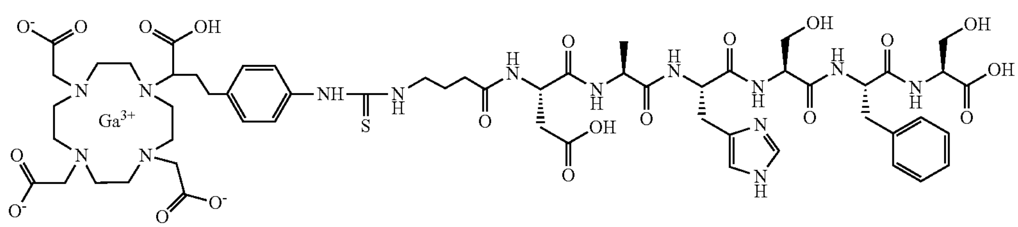 | 1380.12 |
| 6 | 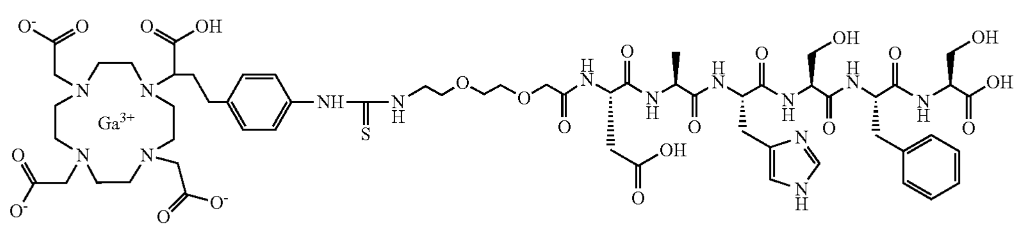 | 1440.17 |

Example 13

The compound of example 11 was coupled to a series of folic acid derivatives, the structures of which are described in example 10. Stages 1 and 2 corresponding to the coupling and deprotection steps are carried out according to the same protocol as that described in example 12 (stages 1 and 2). The complexation is carried out under the same conditions as in stage 3 of example 10.

| No. | Structure | MW |
|-----|-----------|-----|
| 7   | 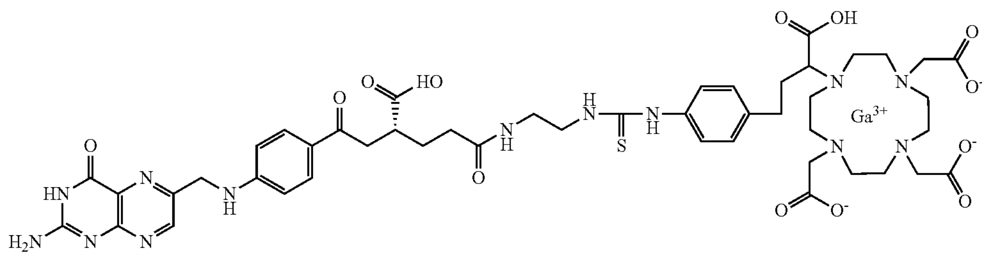          | 1115.84 |
| 8   | 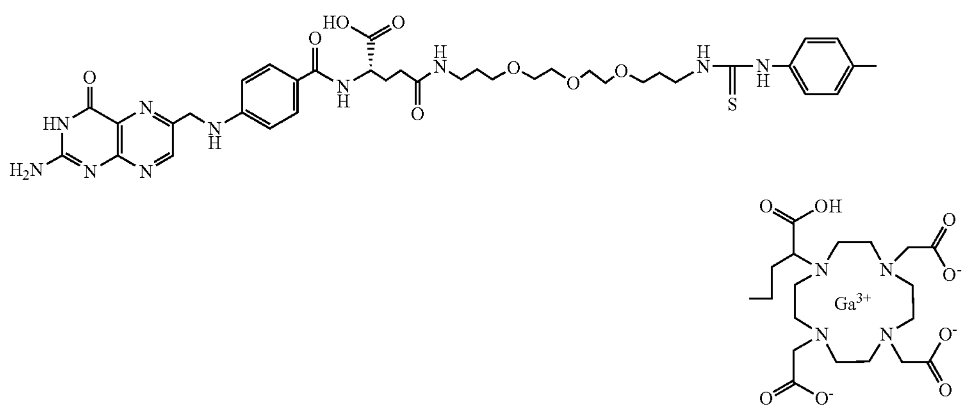          | 1276.05 |
| 9   | 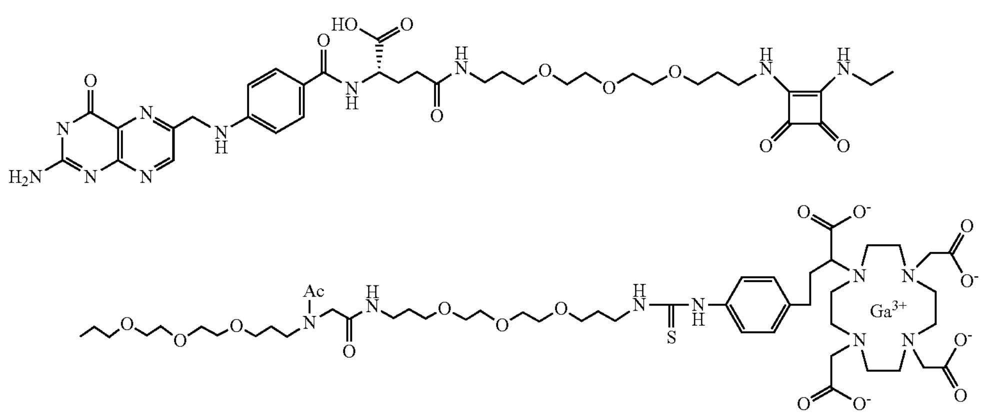          | 1876.77 |

Example 14

[4,7-Bis-tert-butoxycarbonylmethyl-10-(4-isothiocyanatobenzyl)-1,4,7,10-tetraazacyclododec-1-yl)acetic acid tert-butyl ester Stage 1:
Identical to that of example 8

Stage 2:

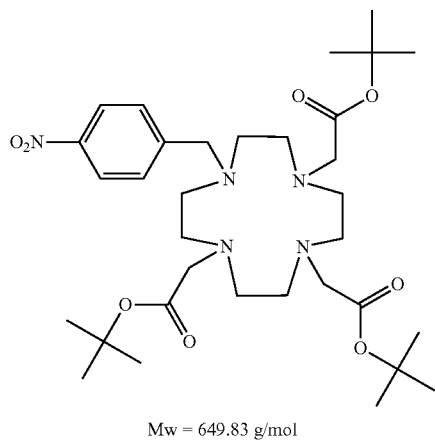 [SMILES: CC(C)(C)OC(=O)CN1CCN(CC(=O)OC(C)(C)C)CCN(Cc2ccc([N+](=O)[O-])cc2)CCN(CC(=O)OC(C)(C)C)CC1]

Mw = 649.83 g/mol 16.8 g of 1-bromo-4-nitrobenzene in solution in 50 ml of $CH_3CN$ are added, dropwise, to a suspension of 20 g of the compound obtained in stage 1 and 10.8 g of $K_2CO_3$ in 400 ml of $CH_3CN$. After stirring for 24 h at 25° C., the reaction medium is filtered, washed with $CH_3CN$, and then concentrated. After acid-base washes, 18 g of product are obtained. Mass spectrum: Mode ES+ m/z=649 with z=1.

Stage 3: Reduction of the Nitro

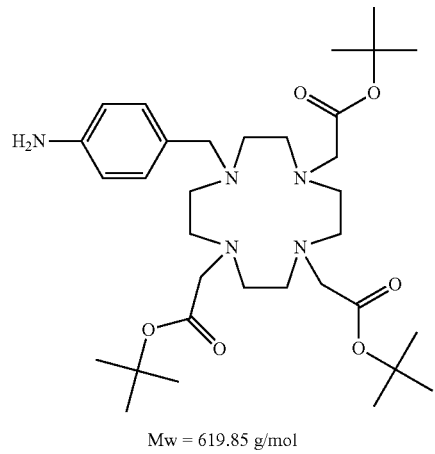 [SMILES: CC(C)(C)OC(=O)CN1CCN(CC(=O)OC(C)(C)C)CCN(Cc2ccc(N)cc2)CCN(CC(=O)OC(C)(C)C)CC1]

Mw = 619.85 g/mol 5 g of the compound obtained in stage 2 are dissolved in 70 ml of MeOH and hydrogenated under pressure (10% palladium-on-charcoal, 25° C. under a hydrogen pressure of $3 \times 10^5$ Pa for 6 h). 4.2 g of product are obtained. Mass spectrum: Mode ES+ m/z=619 with z=1.

Stage 4:

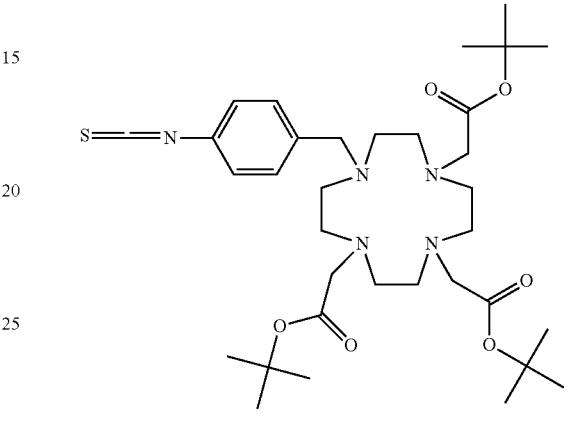

Mw = 661.91 g/mol 2 g (3.2 mmol) of the product derived from stage 3 are solubilized in a mixture of 24 ml of water and 16 ml of $CHCl_3$. 0.53 ml (6.9 mmol) of $SCCl_2$ are added dropwise and the whole is stirred for 1 h 30. The reaction medium is separated by settling out and the organic phase is evaporated under vacuum. The concentrate is taken up in ether and stirred overnight at AT. The precipitate is filtered off and dried under vacuum. m=2 g; mass spectrum: Mode ES+ m/z=661 with z=1.

Example 15

The compound obtained in example 14 is coupled to a series of peptides, the sequences of which are given in example 2, according to the same protocol as that described in example 12.

| No. | Structure | MW |
|---|---|---|
| 1 | 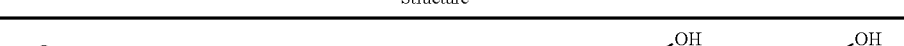 | 1222.948 |

-continued
| No. | Structure | MW |
|---|---|---|
| 2 | 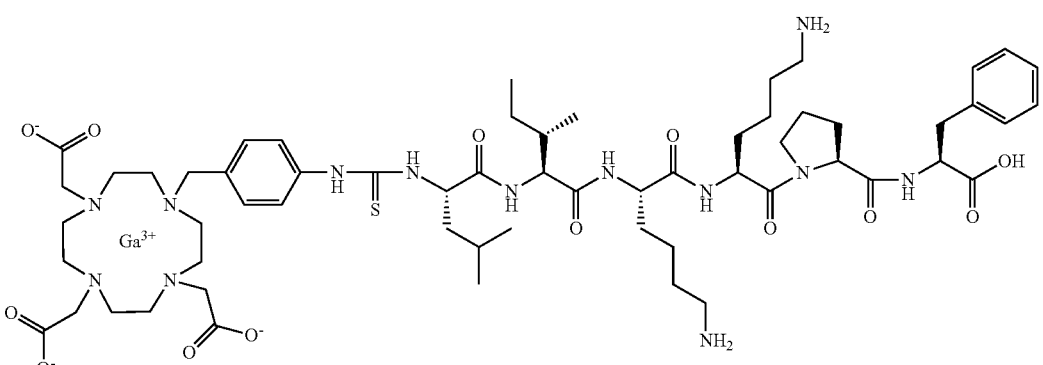 | 1305.27 |
| 3 | 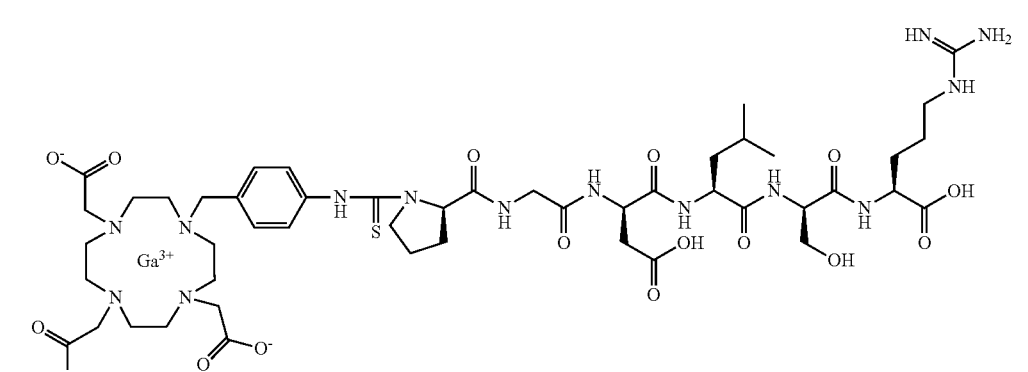 | 1203.99 |
| 4 | 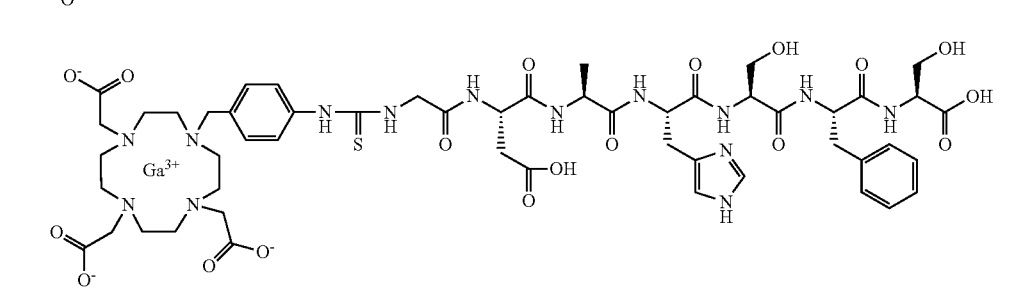 | 1280.00 |
| 5 | 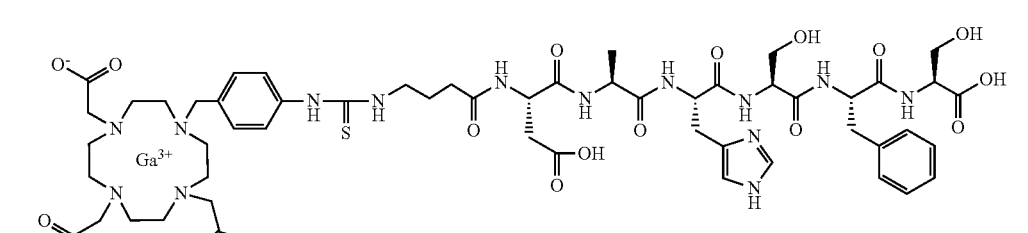 | 1308.05 |
| 6 | 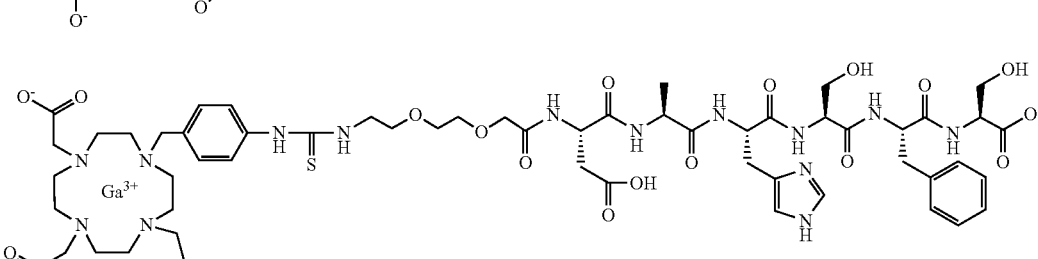 | 1368.40 |

Example 16

The compound of example 14 was coupled to a series of folic acid derivatives, the structures of which are described in example 10, according to the same protocol as in example 13.

| No. | Structure | MW |
|---|---|---|
| 7 | 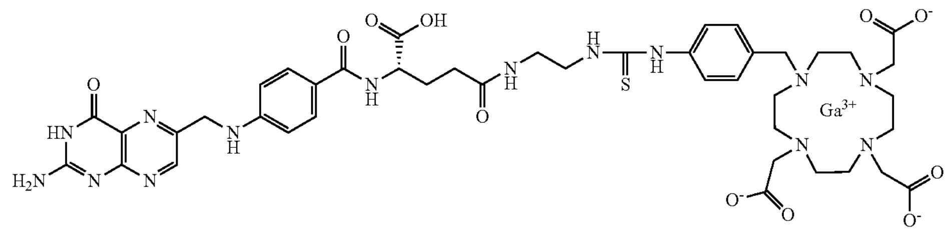 | 1043.77 |
| 8 | 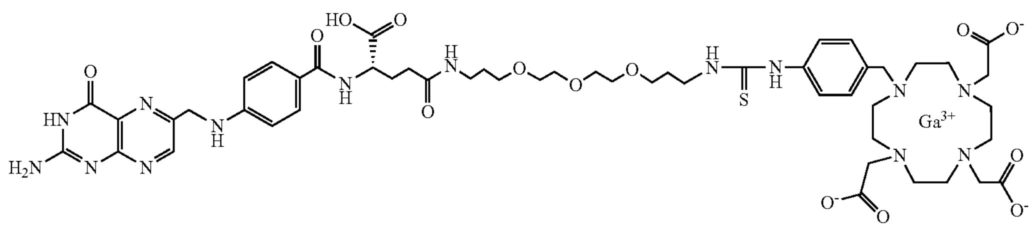 | 1203.99 |
| 9 | 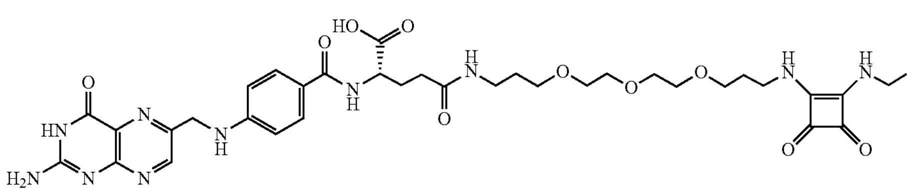 [SMILES: CCNc1c(NCCCOCCOCCOCCCNC(=O)CC[C@H](NC(=O)c2ccc(NCc3cnc4nc(N)[nH]c(=O)c4n3)cc2)C(=O)O)c(=O)c1=O] | 1804.70 |

Example 17

5-(2-Ethoxy-3,4-dioxocyclobut-1-enylamino)-2-(4,7,10-tris-tert-butoxycarbonylmethyl-1,4,7,10-tetraaza-cyclododec-1-yl)pentanoic acid tert-butyl ester Stage 1:
Identical to that of example 8

Stage 2:

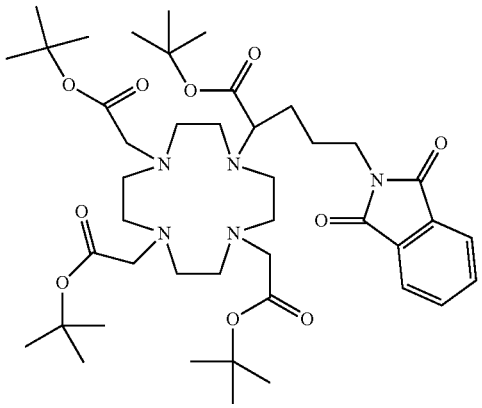

Mw = 816.06 g/mol 29.8 g of 2-bromo-5-(1,3-dioxo-1,3-dihydroisoindol-2-yl)pentanoic acid tert-butyl ester in solution in 50 ml of CH₃CN are added, dropwise, to a suspension of 20 g of the compound obtained in stage 1 and 10.8 g of K₂CO₃ in 400 ml of CH₃CN. After stirring for 24 h at 25° C., the reaction medium is filtered, washed with CH₃CN, and then concentrated. After acid-base washes, 20 g of product are obtained.

Mass spectrum: Mode ES⁺ m/z=815 with z=1.

Stage 3:

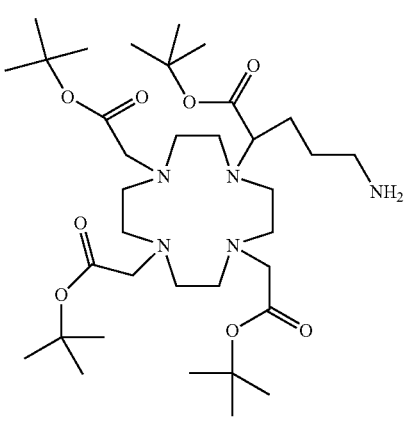

Mw = 685.95 g/mol 5.7 ml of hydrazine hydrate followed by 5 g of the compound obtained in stage 2 are added to 15 ml of water heated to 80° C. The reaction medium is stirred at 80° C. for 3 hours. After cooling, the pH is reduced to 1 with 12N HCl. After filtration, the solution is evaporated under vacuum. 3.6 g of product are obtained.

Mass spectrum: Mode ES⁺ m/z=985 with z=1.

Stage 4:

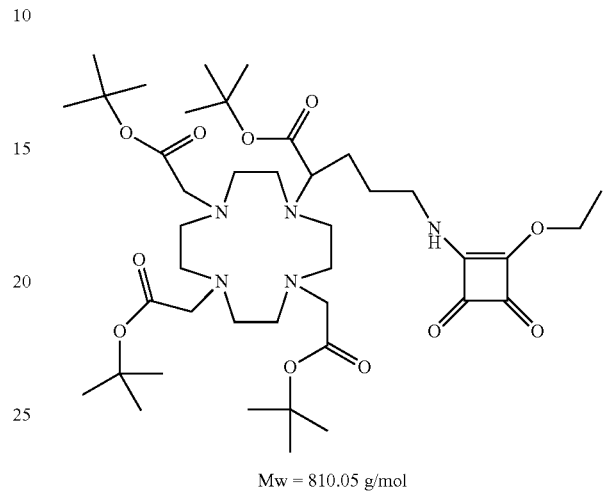

Mw = 810.05 g/mol

Same protocol as in step 5 of example 1.
Mass spectrum: Mode ES⁺ m/z=811 with z=1.

Example 18

The compound obtained in example 17 is coupled to a series of peptides, the sequences of which are given in example 2.

Stages 1 and 2:
Same protocol as that described in example 2

Stage 3:
The complexation is carried out according to the same protocol as in stage 3 of example 9

Example 19

The compound of example 17 was coupled to a series of folic acid derivatives, the structures of which are described in example 10.

Stages 1 and 2:
same protocol as that described in example 2

Stage 3:
The complexation is carried out according to the same protocol as in stage 3 of example 10

| No. | Structure | MW |
|---|---|---|
| 7 | 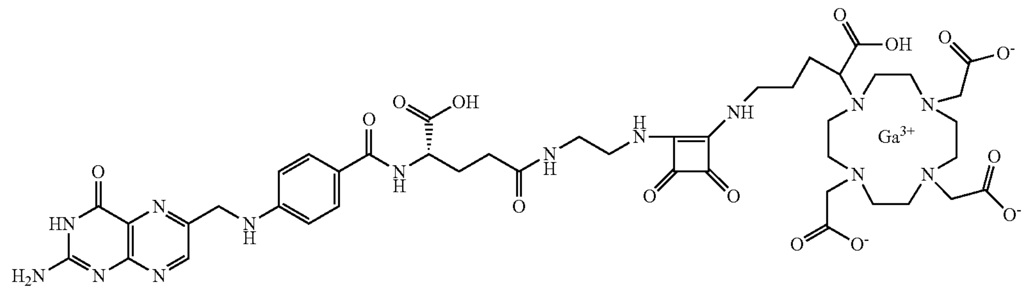 | 1089.70 |
| 8 | 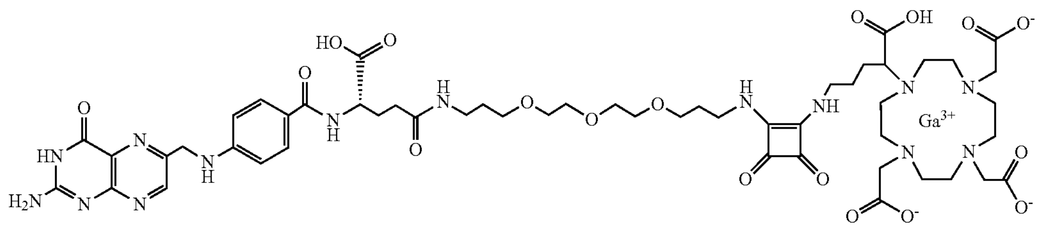 | 1249.95 |
| 9 | 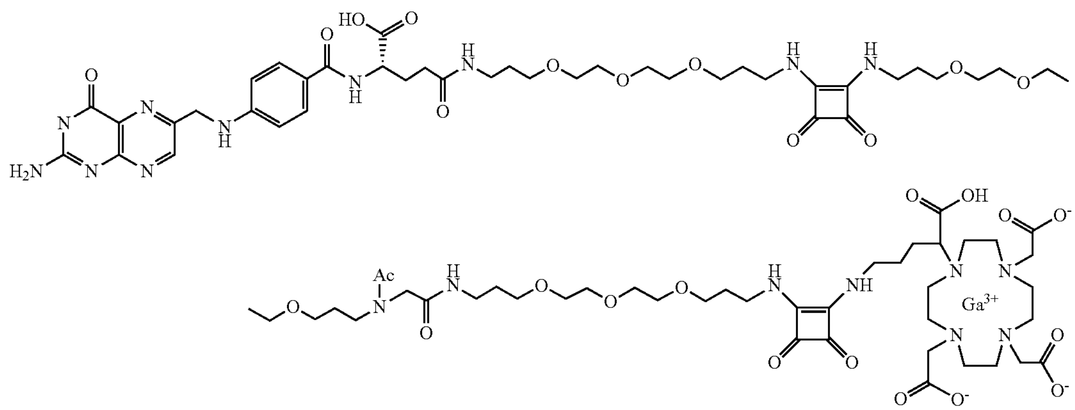 | 1850.66 |

Example 20

2-(4,7,10-Tris-tert-butoxycarbonylmethyl-1,4,7,10-tetraazacyclododec-1-yl)pentanoic acid 1-tert-butyl ester Stage 1:
Identical to that of example 8

Stage 2:

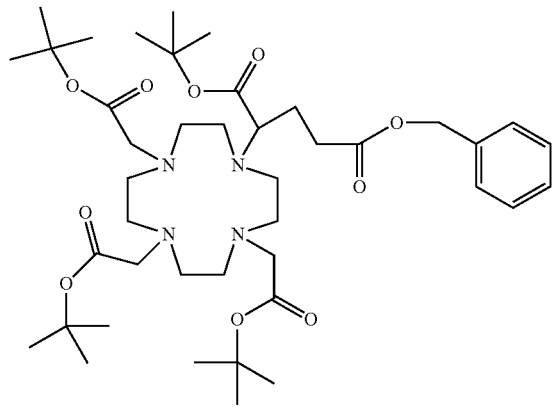

Mw = 791.05 g/mol 27.8 g of 2-bromo-5-(benzyl)pentanoic acid tert-butyl ester in solution in 50 ml of CH$_3$CN are added, dropwise, to a suspension of 20 g of the compound obtained in stage 1 and 10.8 g of K$_2$CO$_3$ in 400 ml of CH$_3$CN. After stirring for 24 h at 25° C., the reaction medium is filtered, washed with CH$_3$CN, and then concentrated. After acid-base washes, 23 g of product are obtained.

Mass spectrum: Mode ES$^+$ m/z=792 with z=1.

Stage 3:

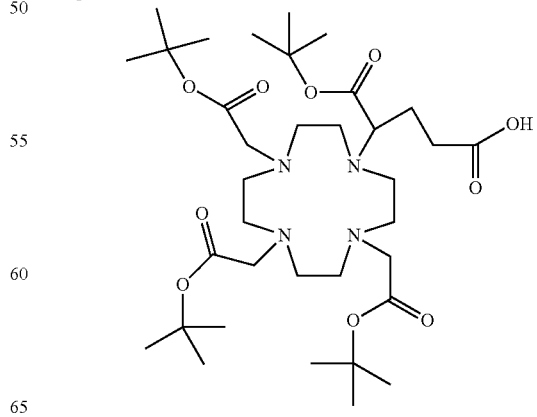

Mw = 700.92 g/mol 10 g of the compound obtained in stage 2 are dissolved in 200 ml of EtOH and hydrogenated under very low pressure (balloon, in the presence of palladium-on-charcoal, at 25° C. for 15 h). After filtration and evaporation of the solvent, 8 g of product are obtained.

Mass spectrum: Mode ES$^+$ m/z=702 with z=1.

Example 21

The compound obtained in example 20 is coupled to a series of peptides, the sequences of which are given in example 2, according to the same protocol as that described in example 9.

| No. | Structure | MW |
|---|---|---|
| 1 | 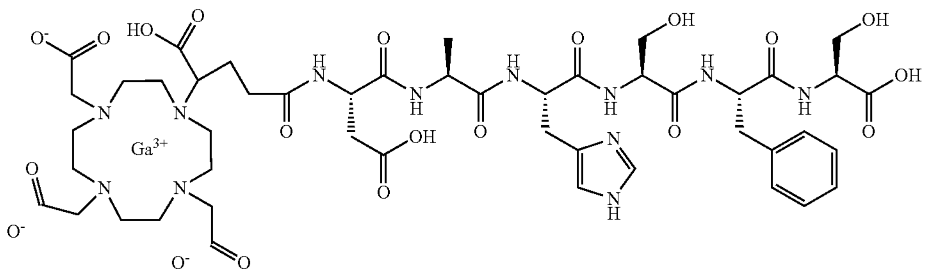 | 1187.83 |
| 2 | 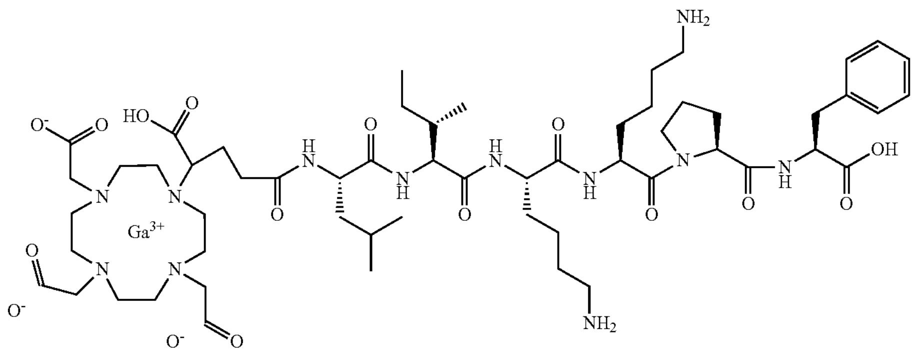 | 1270.15 |
| 3 | 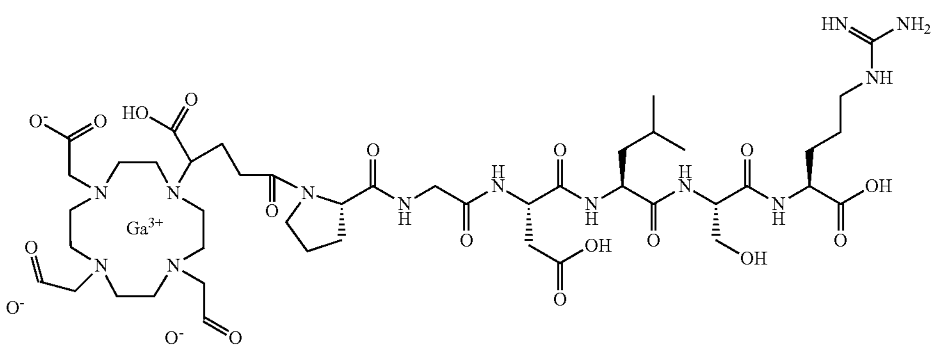 | 1168.87 |
| 4 | 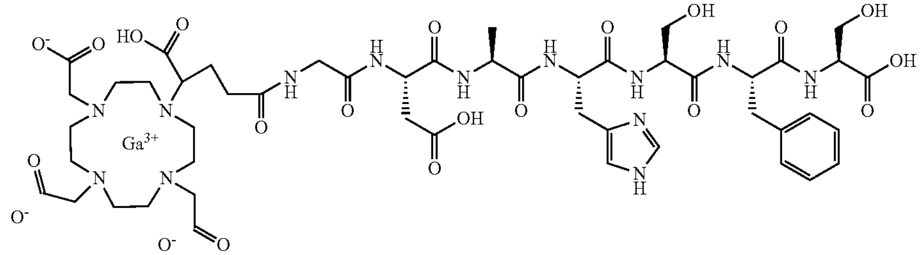 | 1244.88 |

| No. | Structure | MW |
|---|---|---|
| 5 | 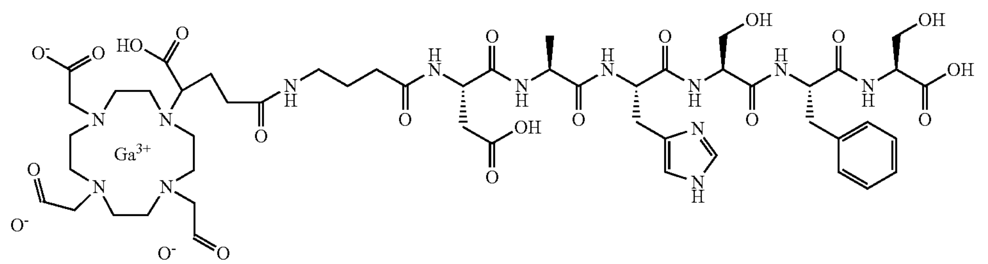 | 1272.94 |
| 6 | 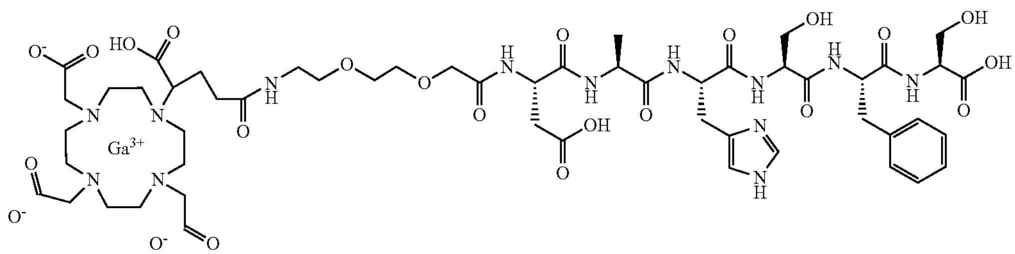 | 1332.99 |

Example 22

The compound of example 20 was coupled to a series of folic acid derivatives, the structures of which are described in example 10, according to the same protocol as that described in example 10.

| No. | Structure | MW |
|---|---|---|
| 7 | 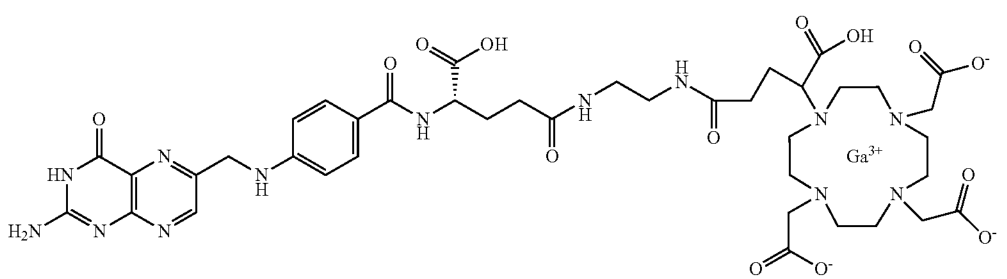 | 1008.66 |
| 8 | 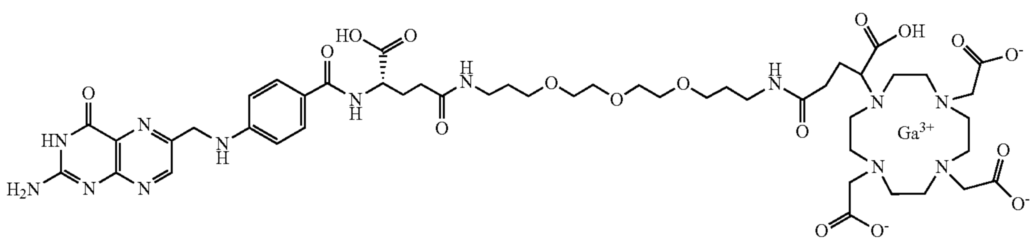 | 1168.87 |
| 9 | 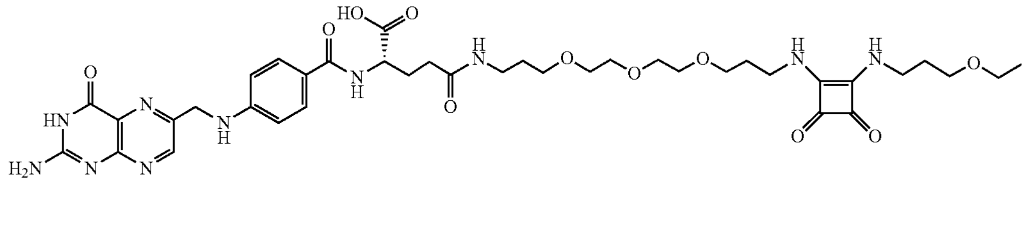 [SMILES: CCOCCCNc1c(NCCCOCCOCCOCCCNC(=O)CC[C@H](NC(=O)c2ccc(NCc3cnc4nc(N)[nH]c(=O)c4n3)cc2)C(=O)O)c(=O)c1=O] | 1769.59 |

| No. | Structure | MW |
|---|---|---|
|  | 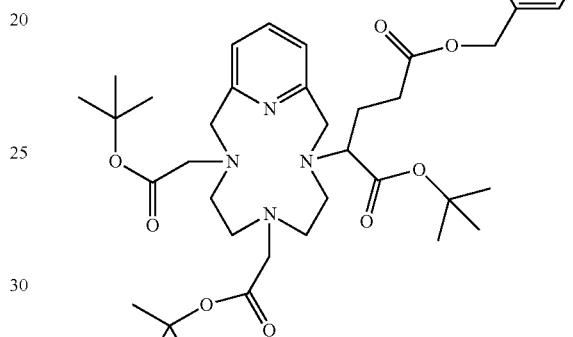 |  |

Other advantageous compounds are obtained by appropriately coupling at least two carboxylic chains of the chelate (instead of one), the compounds of the above table then carrying as many biovectors as there are coupled chains.

Example 23

2-(6,9-Bis-tert-butoxycarbonylmethyl-3,6,9,15-tetraazabicylo[9.3.1]-pentadeca-1(15),11,13-trien-3-yl) pentanoic acid 1-tert-butyl ester Stage 1:

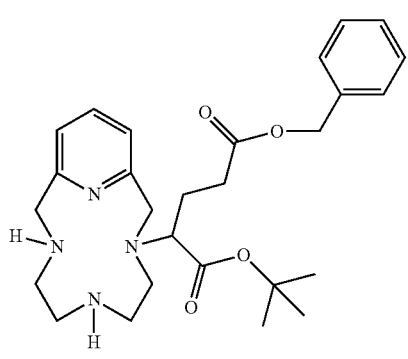

Mw = 482.63 g/mol 10 g of 3,6,9,15-tetraazabicyclo[9.3.1]pentadeca-1(14),11(15),12-triene (48.5 mmol) are dissolved in a water-acetonitrile mixture (170 ml of acetonitrile and 7 ml of water). After the addition of 10 ml of TEA (1.4 eq), the mixture is heated to 50° C. and then 17.3 g of 2-bromo-5-benzylpentanedioic acid tert-butyl ester (1 eq) are added. The medium is stirred for 18 h at 50° C.

The acetonitrile is evaporated off and the residue taken up with dichloromethane is washed with water (100 ml). The organic phase is dried over anhydrous magnesium sulfate and evaporated to dryness. Brown oil. Yield 58%.

Mass spectrum: Mode ES+ m/z=483 with z=1.

Stage 2:

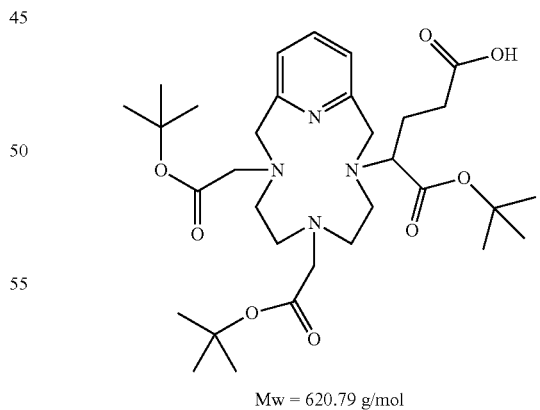

Mw = 710.92 g/mol 5 g of the compound obtained in stage 1 (10 mmol) are solubilized in 200 ml of acetonitrile with 6.4 g of $K_2CO_3$ (4.5 eq). The mixture is brought to reflux and tert-butyl bromoacetate (6.9 g; 3.4 eq) is added rapidly. The reaction medium is brought to reflux for 18 h. The salts are filtered off and the solvent is evaporated off.

Brown oil: 6 g.

Mass spectrum: Mode ES+ m/z=712 with z=1.

Stage 3:

Mw = 620.79 g/mol 5 g of the compound obtained in stage 2 are dissolved in 20 ml of EtOH and hydrogenated under very low pressure (balloon, in the presence of palladium-on-charcoal at 25° C. for 15 h). After filtration and evaporation of the solvent, 4 g of product are obtained.

Mass spectrum: Mode ES+ m/z=622 with z=1.

Example 24

The compound obtained in example 23 is coupled to a series of peptides, the sequences of which are given in example 2, according to the same protocol as that described in example 9.

The products obtained are identical to those of example 7.

Example 25

The compound of example 23 was coupled to a series of folic acid derivatives, the structures of which are described in example 10, according to the same protocol as that described in example 10.

| No. | Structure | MW |
|---|---|---|
| 7 | 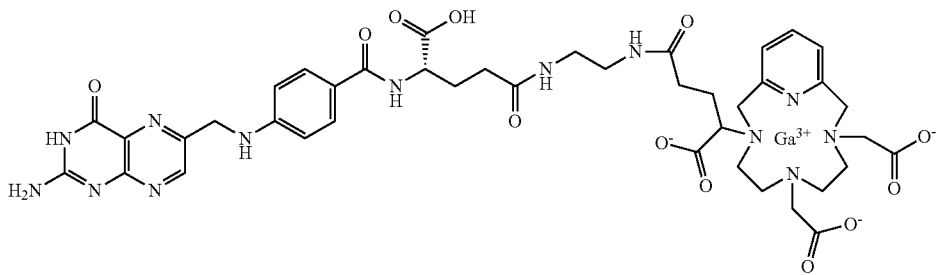 | 984.64 |
| 8 | 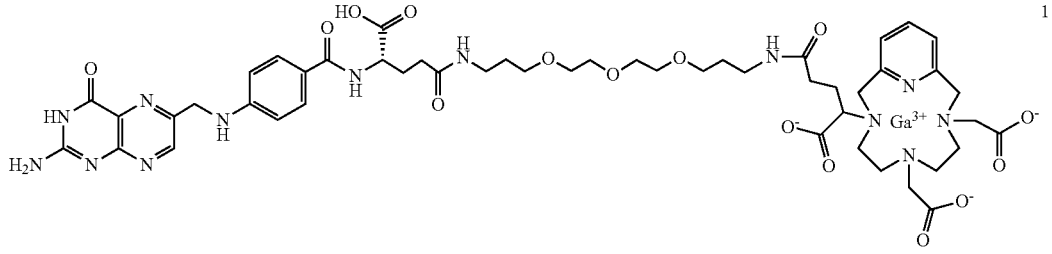 | 1144.85 |
| 9 | 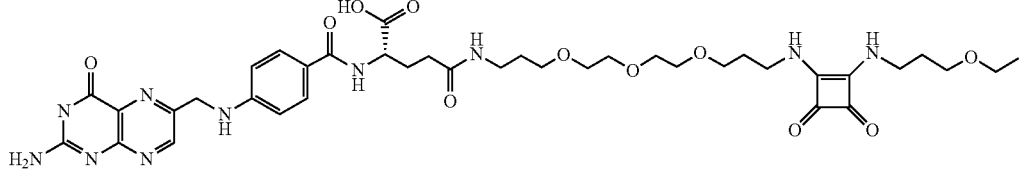 [SMILES: CCOCCCNc1c(NCCCOCCOCCOCCCNC(=O)CC[C@H](NC(=O)c2ccc(NCc3cnc4nc(N)[nH]c(=O)c4n3)cc2)C(=O)O)c(=O)c1=O] | 1745.57 |

Example 26

2-(4,7-Bis-tert-butoxycarbonylmethyl[1,4,7]triazonan-1-yl)-5-(2-ethoxy-3,4-dioxocyclobut-1-enylamino)pentanoic acid tert-butyl ester Stage 1:

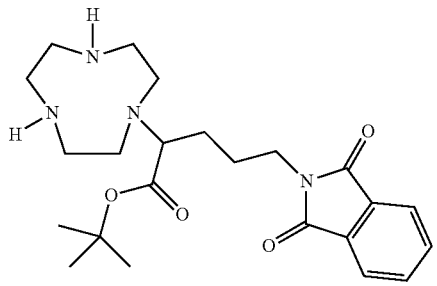

Mw = 430.55 g/mol 10 g of triaza-1,4,7-cyclononane (77.4 mmol) are dissolved in a water-acetonitrile mixture (170 ml of acetonitrile and 7 ml of water). After the addition of 10.7 g of $K_2CO_3$, 29.6 g of 2-bromo-5-(1,3-dioxo-1,3-dihydroisoindol-2-yl)pentanoic acid tert-butyl ester in solution in 50 ml of $CH_3CN$ are added dropwise. After stirring for 24 h at 25° C., the reaction medium is filtered, washed with $CH_3CN$, and then concentrated. After acid-base washes, 20 g of product are obtained.

Mass spectrum: Mode $ES^+$ m/z=431.5 with z=1.

Stage 2:
same protocol as in stage 2 of example 23.

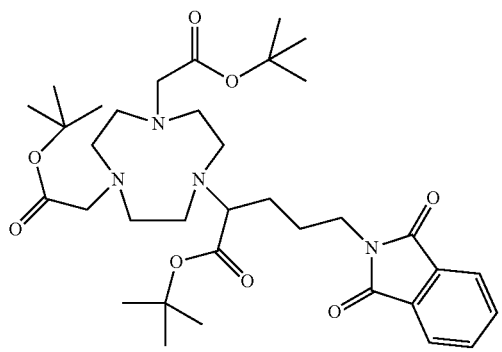

Mw = 658.84 g/mol

Stages 3 and 4:
same protocol as in stages 3 and 4 of example 17.

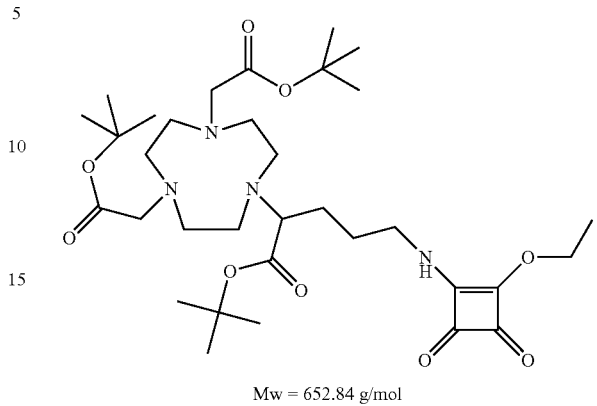

Mw = 652.84 g/mol

Example 27

The compound obtained in example 26 is coupled to a series of peptides, the sequences of which are given in example 2, according to the same protocol as that described in example 18.

The products obtained are identical to those of example 5.

Example 28

The compound of example 26 was coupled to a series of folic acid derivatives, the sequences of which are described in example 10, according to the same protocol as that described in example 19.

| No. | Structure | MW |
|---|---|---|
| 7 | 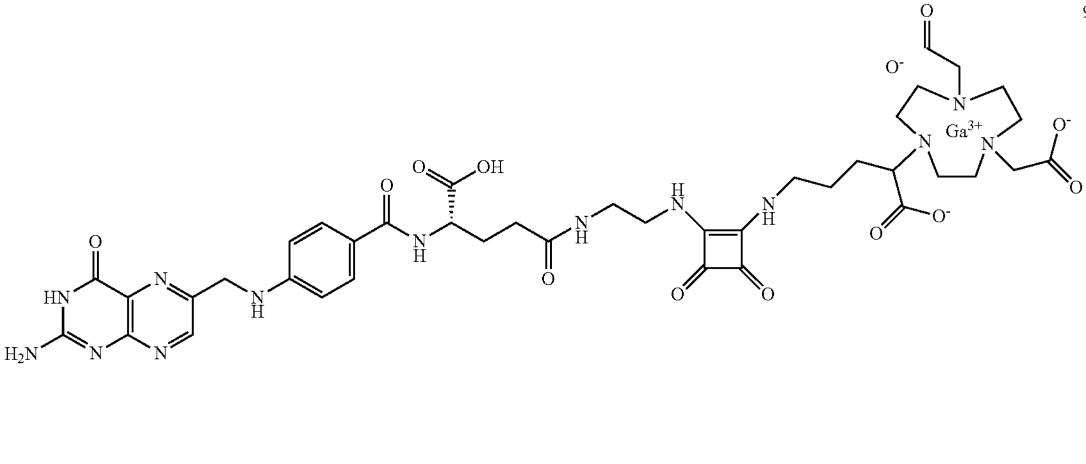 | 988.63 |

-continued

| No. | Structure | MW |
|---|---|---|
| 8 | 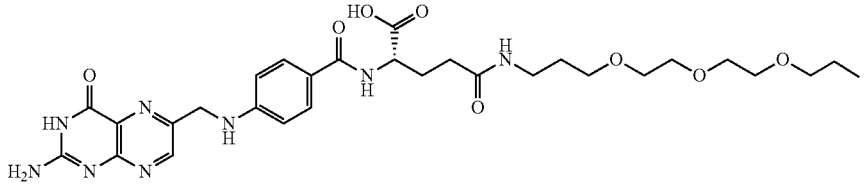 [SMILES: CCCOCCOCCOCCCNC(=O)CC[C@H](NC(=O)c1ccc(NCc2cnc3nc(N)[nH]c(=O)c3n2)cc1)C(=O)O] | 1148.84 |
| 9 | 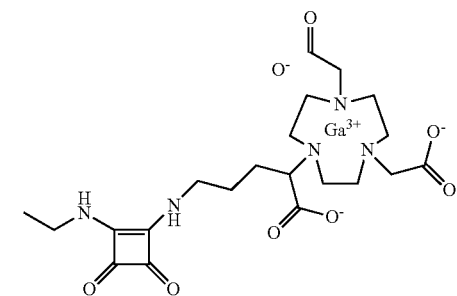 | 1749.56 |

Example 29

The compound obtained in stage 3 of example 17 is coupled to a series of chemical scaffolds (scaffolds) described in the prior art for their therapeutic targeting activity, according to the following protocol:

Stage 1: Coupling of the Scaffolds to the Compound Obtained in Stage 3 of Example 17.

5 mmol of scaffold, 1 g of DCC (5 mmol) and 0.6 g of NHS (5 mmol) are stirred in 50 ml of $CH_2Cl_2$ for 20 min at AT. 20 ml of a solution of the compound obtained in stage 3 of example 17 (5 mmol) and of triethylamine (5 mmol) in DMSO are added to the preactivated ester. After 30 minutes, the reaction medium is precipitated from 600 ml of ethyl ether. The precipitate is filtered off and then dried.

Stages 2 and 3: Deprotection and Complexation Step

The protocol is the same as in stages 2 and 3 of example 9

| Structure | MW |
|---|---|
| 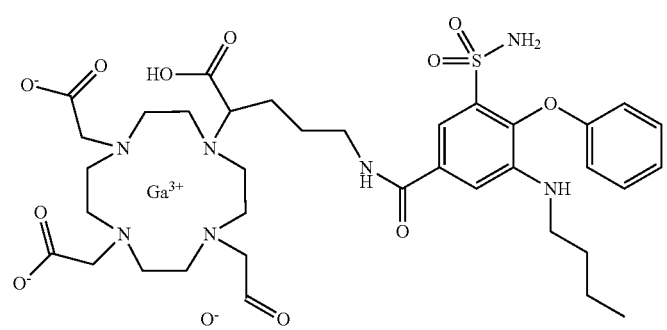 | 874.62 |

| Structure | MW |
|---|---|
| 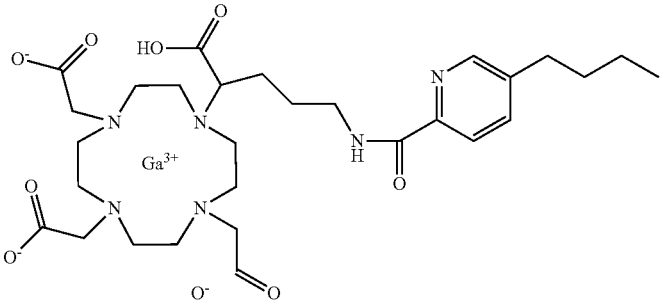 | 689.42 |
| 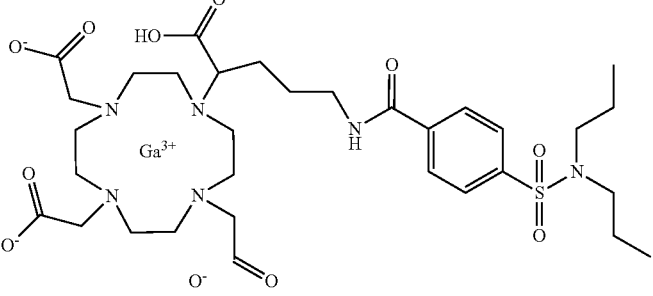 | 795.56 |
| 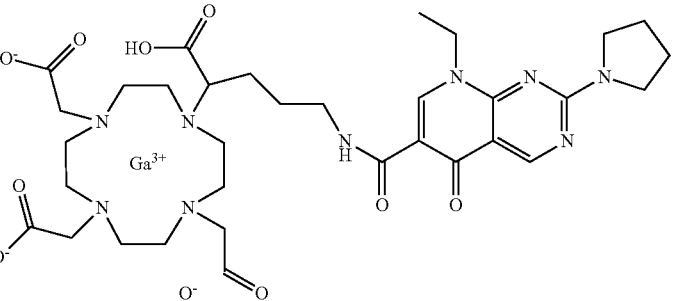 | 798.51 |
| 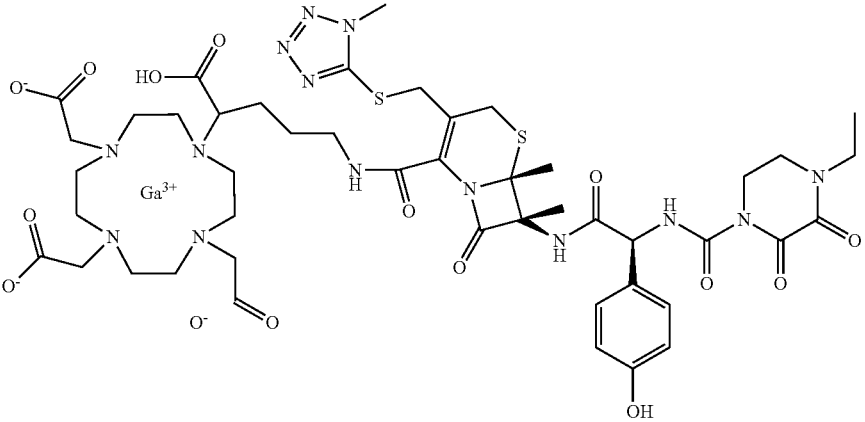 | 1183.93 |

-continued
| Structure | MW |
|---|---|
| 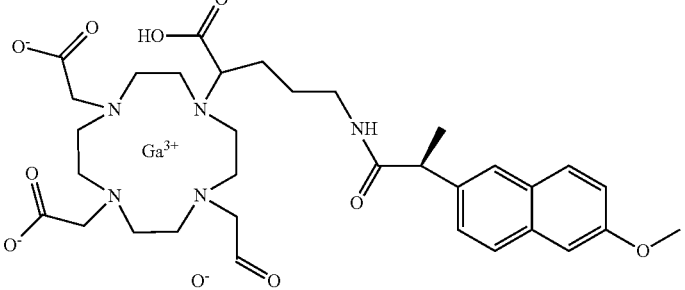 | 740.47 |
| 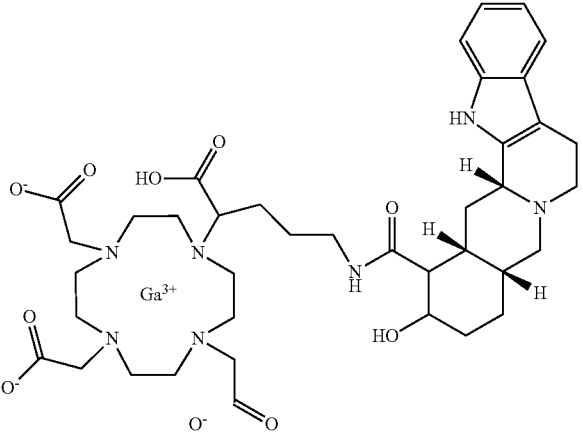 | 850.63 |
| 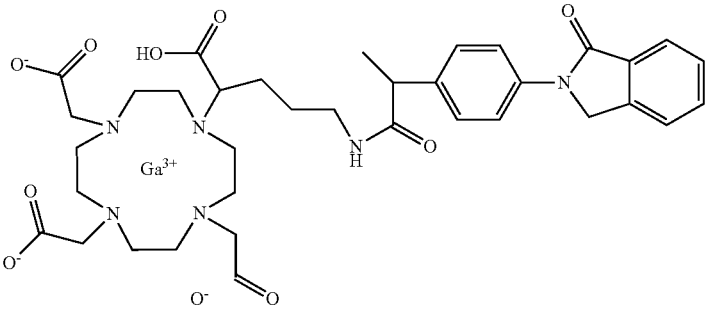 | 791.51 |
| 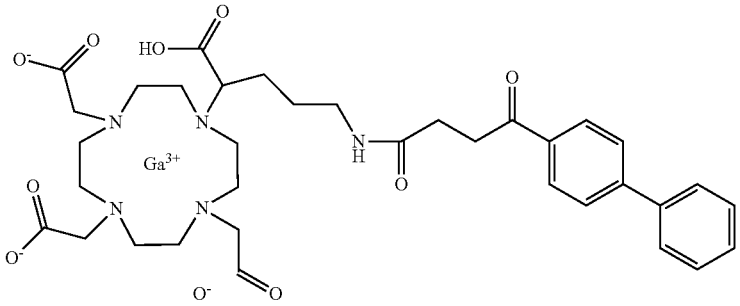 | 764.49 |

| Structure | MW |
|---|---|
| 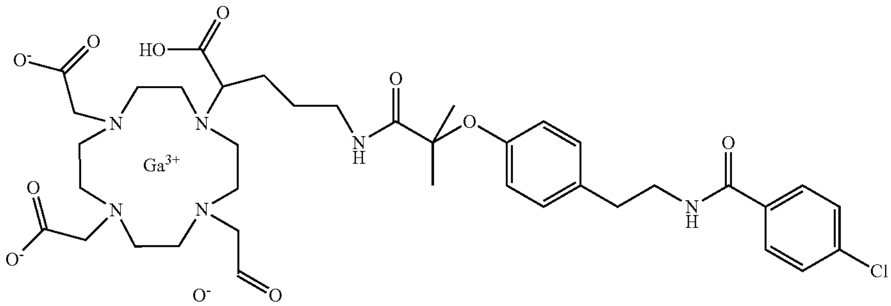 | 872.03 |
| 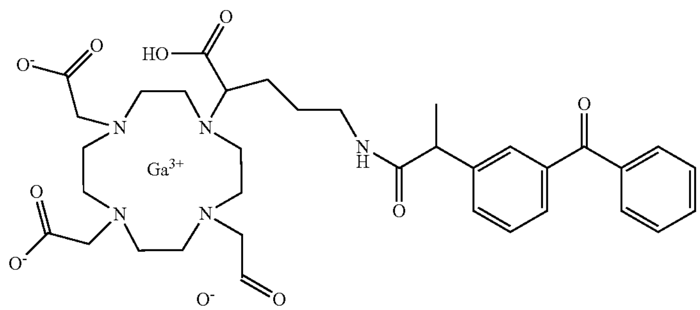 | 764.49 |
| 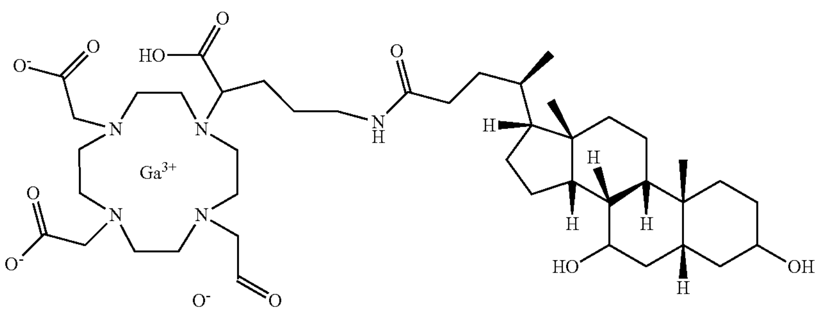 | 902.78 |
| 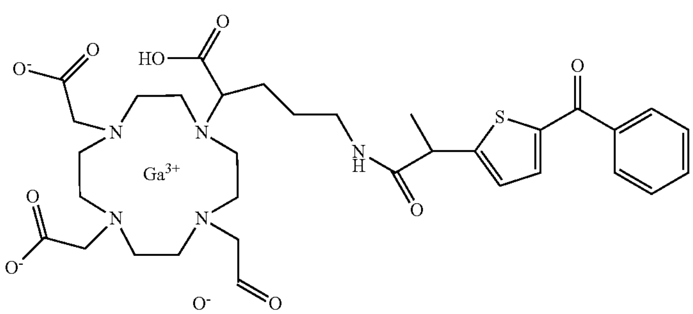 | 770.51 |
| 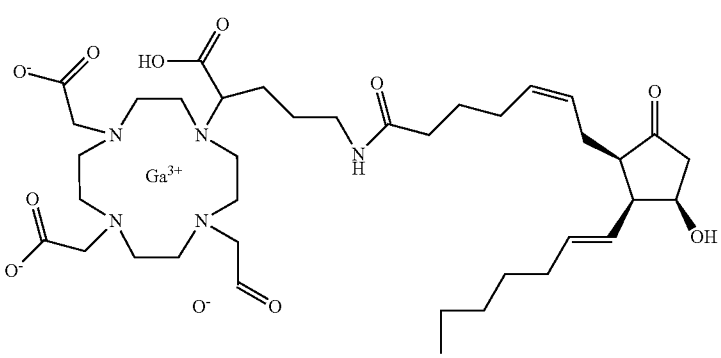 | 832.65 |

-continued

| Structure | MW |
|---|---|
| 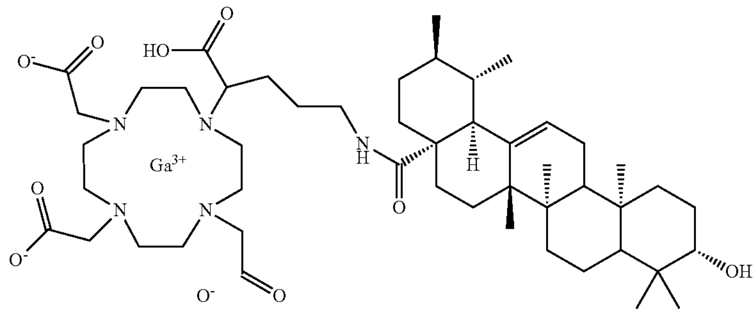 | 981.95 |
| 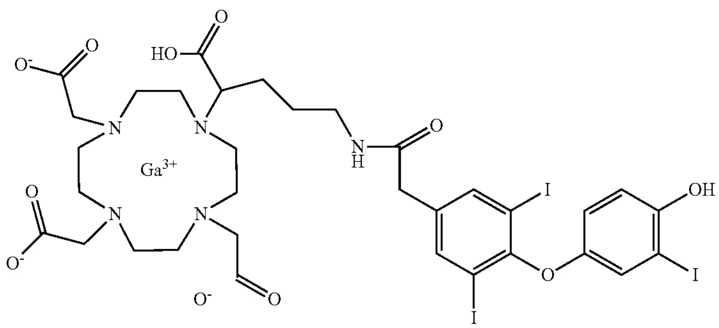 | 1132.14 |
| 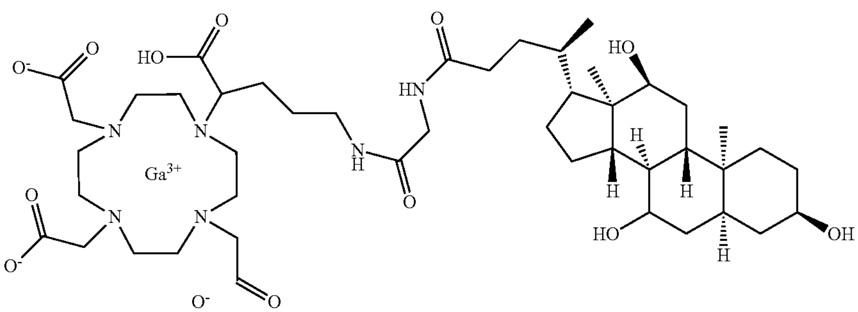 | 975.84 |
| 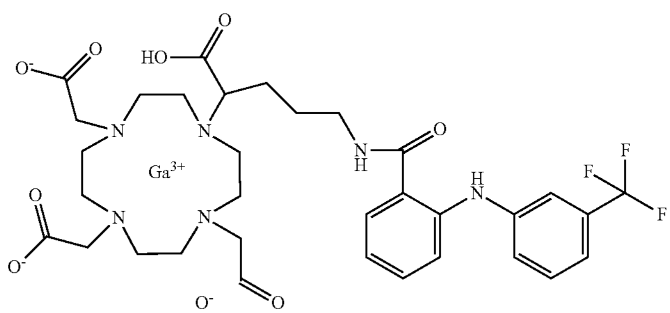 | 791.44 |
| 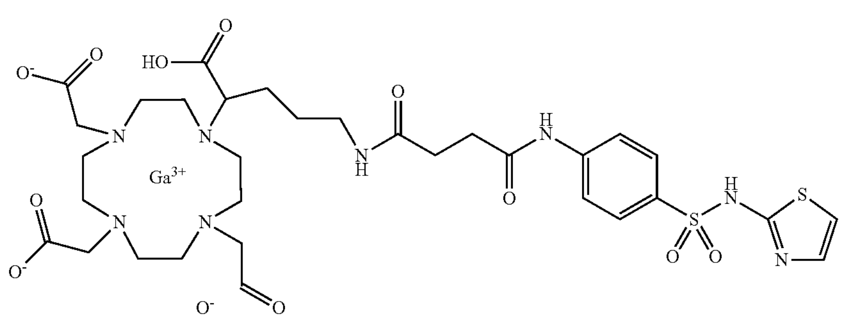 | 865.59 |

| Structure | MW |
|---|---|
| 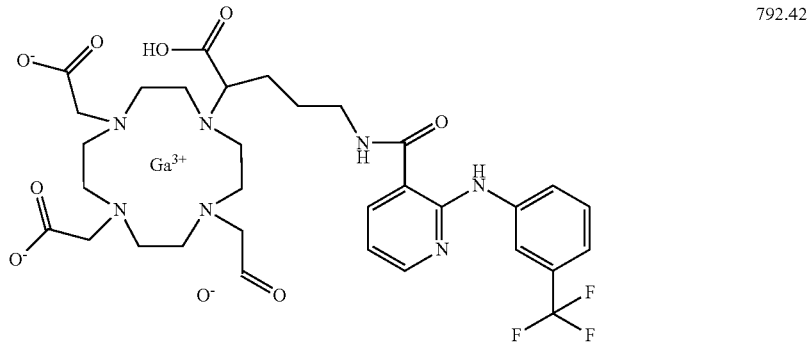 | 792.42 |
| 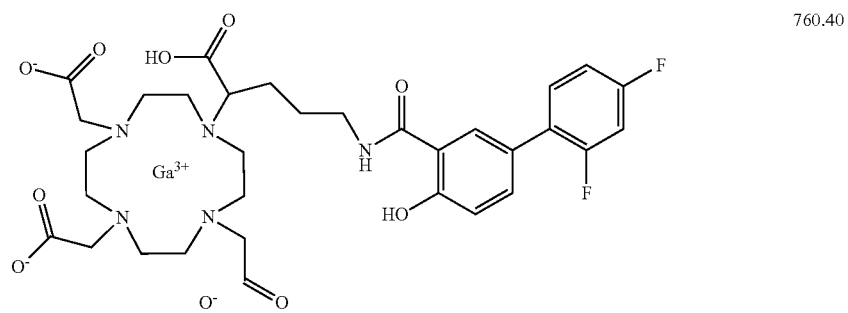 | 760.40 |
| 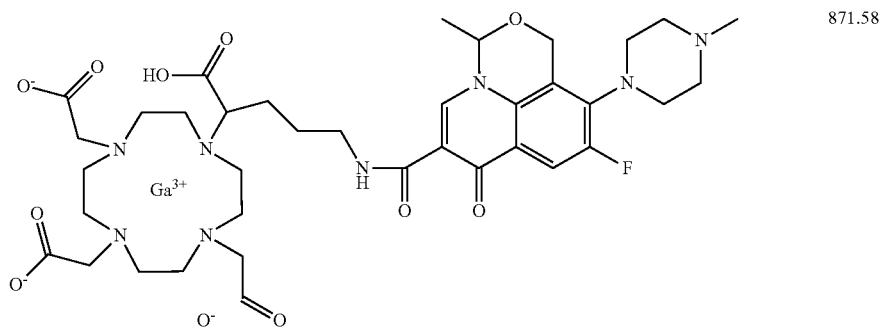 | 871.58 |
| 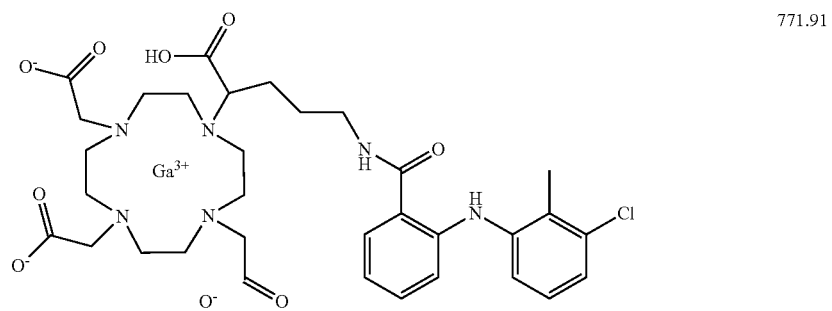 | 771.91 |

-continued

| Structure | MW |
|---|---|
| (structure) | 981.95 |
| (structure) | 853.97 |
| (structure) | 806.36 |

Example 30

The compound obtained in stage 3 of example 17 is coupled to a series of peptides, the sequences of which are given in example 2, according to the same protocol as that described in example 29.

| No. | Structure | MW |
|---|---|---|
| 1 | (structure) | 1172.86 |

-continued
| No. | Structure | MW |
|---|---|---|
| 2 | 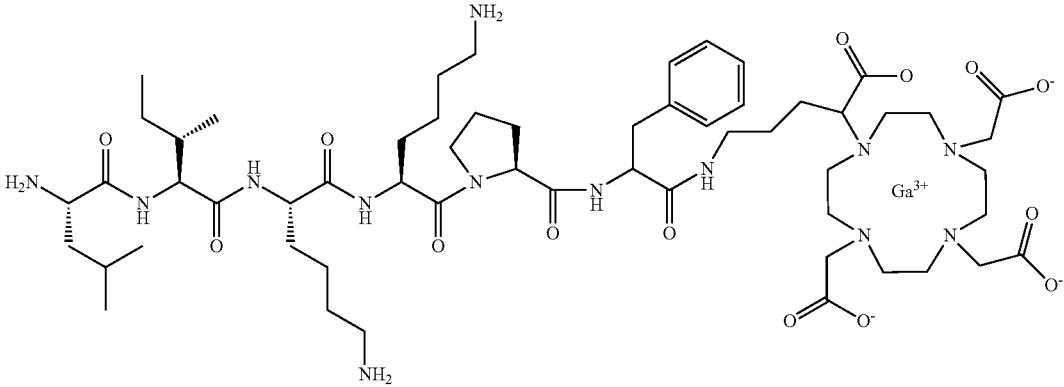 | 1255.18 |
| 3 | 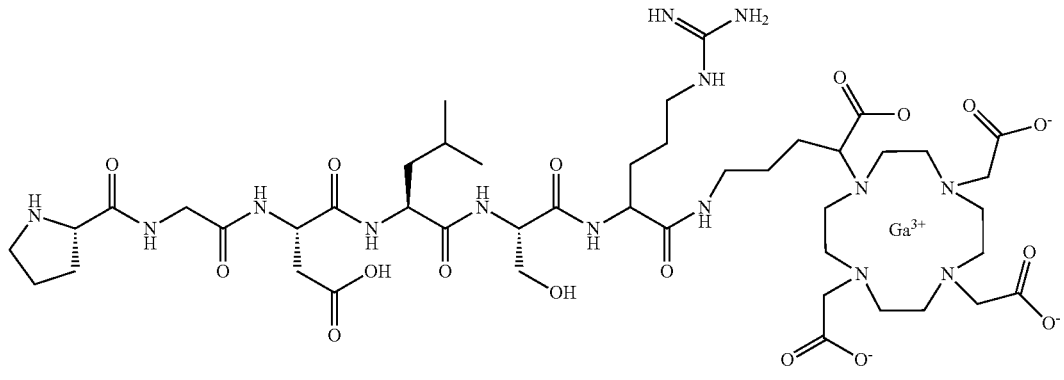 | 1153.90 |
| 4 | 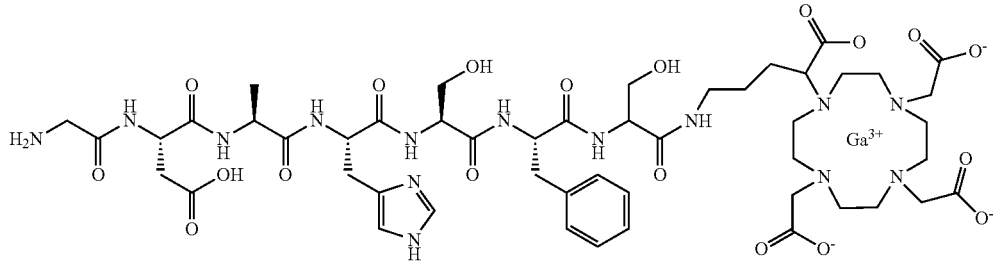 | 1229.91 |
| 5 | 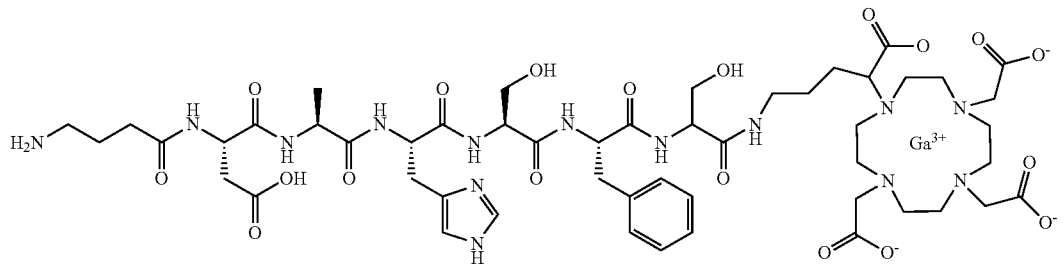 | 1257.97 |
| 6 | 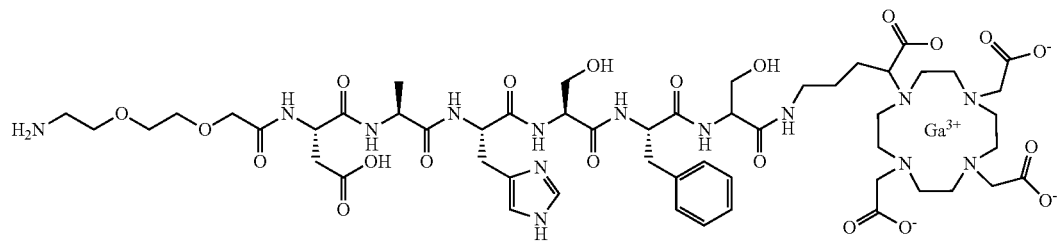 | 1318.02 |

Part II: Example of Coupling of the Chelates with Gallium

Example with 68Ga-radiolabeling of a chelate-biovector compound (5-100 nmol chelate-peptide), with microwave activation for 1 minute at 100 W as described in WO 2004089425.

Example

Addition of sodium acetate Ga68 to the Ga—Ge generator with the pH of the eluate being adjusted to 5.5.
Addition of the chelate-biovector compound.
Microwave activation.
Cooling to ambient temperature.

The invention claimed is:

1. A gallium Ga68 metal complex of the following general formula:

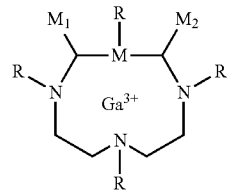

in which:
M1 and M2 each represent a hydrogen atom;
M is a pyridine ring;
R is independently selected from CH$_2$CO$_2$— or H or CHX—CO$_2$—, wherein at least one R is CHXCO$_2$— and X is L-B;
B is folate;
L is a linker selected from:
a) P1-l-P2, wherein P1 and P2, are identical or different, and are selected from O, S, NH, CO$_2$, —NHCO, CONH, NHCONH, NHCSNH, SO$_2$NH— and NHSO$_2$—, and P1 is also a —(CH$_2$)$_2$—CONH— group,
and l is an alkyl, alkoxyalkyl, polyalkoxyalkylene, alkyl interrupted with one or more squarate or with one or more aryl, or alkenyl, alkynyl, or alkyl interrupted with one or more groups selected from —NH—, —O—, —CO—, —NH(CO)—, —(CO)NH—, —O(CO)—, or —(OC)O—;
b) (CH$_2$)$_{n1}$, (CH$_2$)$_{n1}$—CO—, —(CH$_2$)$_{n1}$NH—CO— with n$_1$=2 to 10, (CH$_2$CH$_2$O)$_q$(CH$_2$)$_r$—CO—, (CH$_2$CH$_2$O)$_q$(CH$_2$)$_r$—NH—CO— with q=1-10 and r=2-10, (CH$_2$)$_n$—CONH—, (CH$_2$)$_n$—CONH-PEG, (CH$_2$)$_n$—NH—,

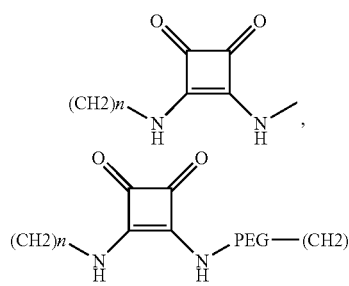

with n=1 to 5, HOOC—CH$_2$—O—(CH$_2$)$_2$—O—(CH$_2$)$_2$—O—CH$_2$—COOH; HOOC—(C$_2$)—CO$_2$—CO$_2$—(CH$_2$)$_2$—OCO—(CH$_2$)$_2$—COOH; HOOC—CH(OH)—CH(OH)—COOH; HOOC—(CH$_2$)$_{n2}$—COOH; NH$_2$—(CH$_2$)$_{n2}$—NH$_2$, with n$_2$=0-20; NH$_2$—(CH$_2$)$_{n3}$—CO$_2$H; NH$_2$—CH$_2$—(CH$_2$—O—CH$_2$)$_{n3}$—CO$_2$H with n$_3$=1 to 10.

2. A metal complex as claimed in claim 1, wherein the chelate comprises at least one portion for masking the chelate in vivo,
wherein the at least one portion of the chelate for masking the chelate is a hydrophilic group or a lipophilic group.

3. A metal complex as claimed in claim 1, wherein the chelate also comprises a portion for recognition of a biological target improving the biodistribution of the compound and/or the transport of the compound, said recognition portion being different than the folate,
wherein the portion for improving the biodistribution of the compound and/or transport of the compound is a COOH or COO— group.

4. A composition comprising a metal complex as claimed in claim 1 and a non-complexed linear or macrocyclic chelate, wherein the non-complexed linear or macrocyclic chelate is present at a concentration of between 0.01 and 100 mM.

5. A composition comprising a metal complex as claimed in claim 1 and calcium.

6. A composition comprising a metal complex as claimed in claim 1 and at least one stabilization agent against radiolysis.

7. A kit for administering a gallium Ga68-labeled product, comprising a metal complex as claimed in claim 1 and instructions.

8. A diagnostic composition for PET, MRI, and CT imaging comprising a metal complex as claimed in claim 1.

9. A metal complex according to claim 1, selected from:

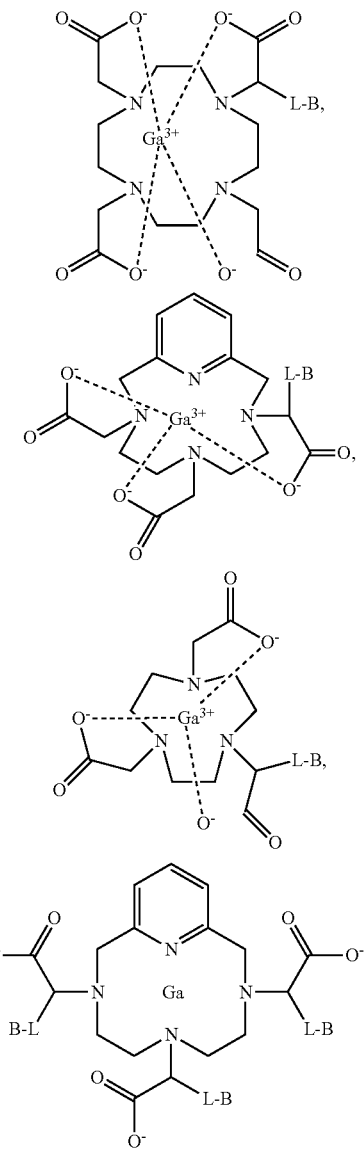

-continued

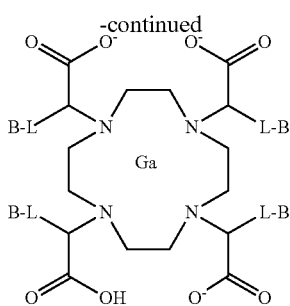

in which L and B are as defined in claim 1.

10. The metal complex as claimed in claim 2, wherein the portion for masking the chelate in vivo is a linker comprising at least one portion for masking the chelate in vivo,
 wherein the linker has a hydrophilic group.

11. The metal complex as claimed in claim 6, wherein the agent is selected from the group consisting of free-radical blockers, dithiocarbamates, PDTC, soluble compounds with selenium, selenomethionine, selenocysteine, and methionine.

12. A kit for administering a gallium Ga68-labeled product, comprising a composition as claimed in one of claims 4 to 6.

13. The metal complex of claim 1 selected from:

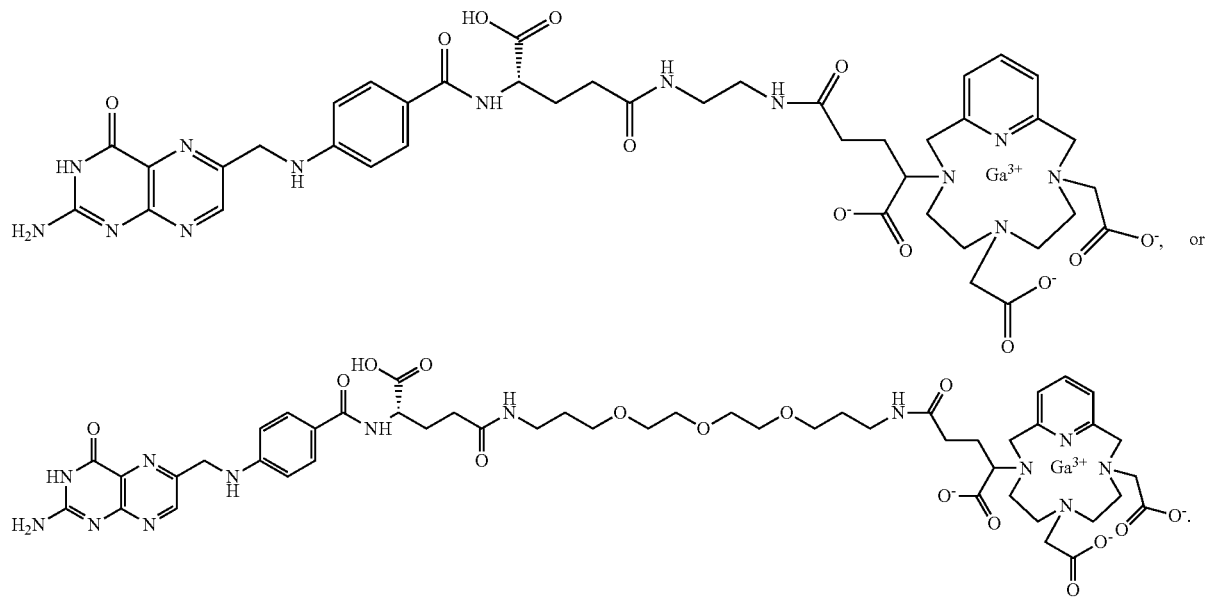

\* \* \* \* \*

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Cys Arg Arg Glu Thr Ala Trp Ala Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 2

Xaa Xaa Xaa Tyr Xaa Xaa Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Arg Pro Leu Pro Pro
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Ala Pro Pro Leu Pro Pro Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 5

Cys Ser Val Thr Cys Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Tyr Ile Gly Ser Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Asp Ala His Ser Phe Ser
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Leu Ile Lys Lys Pro Phe
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Pro Gly Asp Leu Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Gly Asp Ala His Ser Phe Ser
1               5
```